United States Patent
Baati et al.

(10) Patent No.: US 9,522,928 B2
(45) Date of Patent: Dec. 20, 2016

(54) MANNOSYLATED COMPOUNDS USEFUL FOR THE PREVENTION AND THE TREATMENT OF INFECTIOUS DISEASES

(71) Applicants: UNIVERSITE DE STRASBOURG, Strasbourg (FR); CENTRE NATIONAL DE LA RECHERCHE SCIENTIFIQUE, Paris (FR)

(72) Inventors: Rachid Baati, Souffelweyersheim (FR); Laure Dehuyser, Saint Andre de Corcy (FR); Christopher Mueller, Strasbourg (FR); Evelyne Schaeffer, Strasbourg (FR); Alain Wagner, Strasbourg (FR)

(73) Assignees: UNIVERSITE DE STRASBOURG, Strasbourg (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 14/358,157

(22) PCT Filed: Nov. 14, 2012

(86) PCT No.: PCT/EP2012/072592
§ 371 (c)(1),
(2) Date: May 14, 2014

(87) PCT Pub. No.: WO2013/072355
PCT Pub. Date: May 23, 2013

(65) Prior Publication Data
US 2014/0349952 A1 Nov. 27, 2014

(30) Foreign Application Priority Data
Nov. 15, 2011 (EP) .................................. 11306493

(51) Int. Cl.
C07H 15/08 (2006.01)
A61F 6/04 (2006.01)
A61K 47/48 (2006.01)
C07H 15/06 (2006.01)
C07H 15/10 (2006.01)

(52) U.S. Cl.
CPC ................. *C07H 15/08* (2013.01); *A61F 6/04* (2013.01); *A61K 47/48215* (2013.01); *C07H 15/06* (2013.01); *C07H 15/10* (2013.01)

(58) Field of Classification Search
None
See application file for complete search history.

(56) References Cited

FOREIGN PATENT DOCUMENTS

WO WO 2010/054406 * 5/2010

OTHER PUBLICATIONS

Supplementary Information for Wang et al (Langmiur, 1999).*
Sattin, S. "Inhibition of DC-SIGN-Mediated HIV Infection by a Linear Trimannoside Mimic in a Tetravalent Presentation" *ACS Chemical Biology*, Mar. 19, 2010, pp. 301-312, vol. 5, No. 3.
Tabarani, G. et al. "Mannose hyperbranched dendritic polymers interact with clustered organization of DC-SIGN and inhibit gp120 binding" *FEBS Letters*, May 1, 2006, pp. 2402-2408, vol. 580, No. 1.
Wang, S. et al. "Chemical and Photochemical Dual Polymerization in a Mixed Langmuir Monolayer of Diacetylene Derivatives and Octadecyltrimethoxysilane" *Journal of Colloid and Interface Science*, 1998, pp. 303-308, vol. 207.
Wang, S. et al. "Surface Chemistry, Topography, and Spectroscopy of a Mixed Monolayer of 10,12-Pentacosadiynoic Acid and Its Mannoside Derivative at the Air-Water Interface" *Langmuir*, Aug. 1, 1999, pp. 5623-5629, vol. 15, No. 17.

* cited by examiner

*Primary Examiner* — Leigh C Maier
(74) *Attorney, Agent, or Firm* — Saliwanchik, Lloyd & Eisenschenk

(57) ABSTRACT

The present invention relates to new anti-infectious compounds consisting of (i) a polar head having from one to three mannose, dimannose or trimannose moieties, which is coupled through an appropriate linker to (ii) a single lipid chain of at least 17 carbon atoms in length. Pharmaceutical compositions and therapeutic uses thereof are also provided.

20 Claims, 8 Drawing Sheets

MANNOSYLATED COMPOUNDS USEFUL FOR THE PREVENTION AND THE TREATMENT OF INFECTIOUS DISEASES

CROSS-REFERENCE TO RELATED APPLICATION

This application is the U.S. national stage application of International Patent Application No. PCT/EP2012/072592, filed Nov. 14, 2012.

FIELD OF THE INVENTION

The present invention relates to new compounds useful for preventing or treating infectious diseases, in particular, Dengue virus and HIV infections as well as related diseases.

BACKGROUND OF THE INVENTION

Dendritic cells (DCs) are essential antigen presenting cells (APC), which play a crucial role in the induction of specific immune response against pathogens. Immature DCs, localized in peripheral mucosal tissues throughout the body, are sentinels that monitor for the presence of pathogens. After detecting and internalizing a pathogen, DCs migrate from the site of infection to draining lymphoid organs. During this migration, DCs undergo a deep maturation that leads, among other things, to the processing of antigens from pathogen and their presentation by membrane major histocompatibility complex (MHC). Once in lymph nodes, DCs enable the selection of rare circulating antigen-specific lymphocytes and, subsequently, lymphocyte expansion and differentiation (for review, see Banchereau et al., 2000).

It clearly appears that recognition of pathogens by DCs is one of the crucial steps in the induction of protective immunity. DCs express a repertoire of receptors including Toll-like receptors and C-type lectins. C-type lectins recognize specific carbohydrate moieties that are present on the cell walls of pathogens. The binding of a pathogen by C-type lectin-carbohydrate interaction generally leads to the internalization of the pathogen.

Among C-type lectins, one may note DC-SIGN (DC-specific intercellular adhesion molecule 3 [ICAM-3]-grabbing nonintegrin), which is highly expressed at the surface of DCs. DC-SIGN is a type II membrane protein with a short amino-terminal cytoplasmic tail, a neck region and a single C-terminus carbohydrate recognition domain (CRD). The extracellular CRD is a tetramer stabilized by an alpha-helical stalk, which specifically recognizes glycosylated proteins and ligands bearing high-mannose oligosaccharides. In this respect, DC-SIGN was shown to bind the HIV-1 envelope glycoprotein gp120 that displays several high-mannose N-glycan structures, as well as to the mannose-capped cell wall component of *Mycobacterium tuberculosis* ManLAM (lipoarabinomannan). High binding affinity of Lewis-group antigens containing fucose residues in different anomeric linkages for DC-SIGN was also observed. Finally, it was shown that the interaction of DC-SIGN with high-mannose moieties present on glycoproteins is multivalent and calcium-dependent (Feinberg, et al., 2001; Mitchell, et al., 2001). (For review, see Kooyk and Geijtenbeek, *Nat Rev Immunol.*, 2003, 3, 697-709).

DC-SIGN binds to a broad range of pathogens including viruses, bacteria, fungi and parasites (Kooyk and Geijtenbeek, *supra*). Several studies showed that some pathogens subvert DC-SIGN functions in order to escape immune surveillance, promote their dissemination and/or modulate the immune response. Such mechanisms are observed for distinct viruses such as Ebola virus (Alvarez et al., 2002), avian H5N1 influenza virus (Wang, et al., 2008), cytomegalovirus (CMV), hepatitis C virus (Kooyk, and Geijtenbeek, 2004) and Dengue virus (Tassaneetrithep, 2003), for which DC-SIGN is involved in early transmission and, in some cases, in immune modulation. Bacteria such as *Mycobacterium tuberculosis* (Geijtenbeek et al., 2003) also take advantage of DC-SIGN for blocking maturation of infected DC and for inducing immunosuppression.

Concerning human immunodeficiency virus type 1 (HIV-1) infection, it is established that DCs are the first predominant cells to be infected (Gurney, et al., 2005; Hu, et al., 2000; Shen, et al., 2010; Wilkinson and Cunningham, 2006). They greatly contribute to early-stage HIV dissemination and transmission by their ability to capture and transport virions and infect new target cells (Geijtenbeek, et al., 2000; Piguet and Steinman, 2007; Wu and KewalRamani, 2006). Trans-infections mediated by DCs can occur by distinct pathways but the most important mechanism is mediated by DC-SIGN. Due to the high binding affinity of DC-SIGN for HIV-1 envelope glycoprotein gp120, HIV-1 virions are captured by DC-SIGN expressed on DC. Captured HIV-1 virions do not undergo lysosomal degradation and thus remain infectious. Subsequently, after their migration into lymph nodes, DCs induce trans-infection of target CD4+ cells by captured HIV-1 virions, through cell-cell junctions called infectious synapses (Wu and KewalRamani, 2006). According to recent data, the vast majority of virions transmitted in trans originate from the cell plasma membrane rather than from intracellular vesicles (Cavrois, et al., 2007).

Because of the crucial role that DC-SIGN may play in the early stage of viral infections, several studies were carried out to identify synthetic DC-SIGN ligands to be used in human therapy, in particular for preventing or treating viral infections such as HIV-1 infection.

Frison et al. (2003) described that glycoclusters made of oligolysine substituted by one to four mannobiose moieties failed to bind DC-SIGN and were not internalized by DC-SIGN-expressing HeLa cells, contrary to Man-BSA (i.e., bovine serum albumin bearing 25 ±3 mannose residues) and to oligoclusters substituted by Lewis oligosaccharides.

Since the interaction of DC-SIGN with pathogen glycoproteins displaying high-mannose structures is multivalent, it was suggested that a multivalent presentation of mannosyl oligosaccharides on an adequate scaffold mimicking natural mannose structures occurring in pathogen glycoproteins was required to bind DC-SIGN (Tabarani et al., 2006, FEBS Lett., 2006, 580, 2402-2408). Accordingly, several recent studies have reported the synthesis of multivalent mannose-containing molecules. Mannose hyperbranched dendritic polymers were found to interfere with the binding between recombinant DC-SIGN and gp120 proteins (Tabarani, et al., 2006; Wang, et al., 2008). Gold mannoglyco-nanoparticles inhibited HIV trans-infection mediated by Raji-DC-SIGN cells (Martinez-Avila, et al., 2009). However, their use as an anti-HIV agent in vivo cannot be contemplated because of their toxicity. Finally, mannosyl glycodendritic structures based on second and third generations of Boltorn hyperbranched dendritic polymers functionalized with mannose inhibited HIV trans-infection mediated by THP-1/DC-SIGN cells (Sattin, et al., 2010). However, despite a good activity, such compounds display several drawbacks: they are difficult and expensive to prepare and may display a low solubility in biological media.

There is still a need for new compounds displaying a high affinity for DC-SIGN, which may be used as anti-infectious agents for the prevention and treatment of infectious diseases such as HIV infection.

SUMMARY OF THE INVENTION

The invention relates to a compound of formula (I) or a pharmaceutically acceptable salt, solvate or ester thereof,

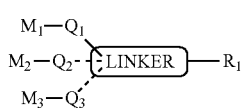

(I)

wherein:
- $R_1$ is a $C_{17}$-$C_{30}$ saturated or unsaturated linear alkyl, optionally substituted by one or more $C_1$-$C_3$ alkyl radicals,
- $M_2$-$Q_2$ and $M_3$-$Q_3$ are optionally present,
- $M_1$ is selected from the group consisting of mannosyl, dimannosyl and trimannosyl,
- $M_2$ and $M_3$ are independently selected from the group consisting of mannosyl, dimannosyl, trimannosyl and therapeutic agent moieties, preferably anti-infectious agent moieties, having a molecular weight of at most 800 g/mol$^{-1}$,
- $Q_1$, $Q_2$ and $Q_3$ are independently selected from the group of oligoether-based spacers comprising at least one —$(OR_8)_n$-moiety, wherein $R_8$ is a linear or branched $C_1$-$C_4$ alkyl and n is an integer from 2 to 10, and
- LINKER is selected among bifunctional, trifunctional and tetrafunctional linkers having a backbone of 1 to 20 carbon atoms and at least two heteroatoms independently selected from N, S and O.

In some embodiments of the invention, $R_1$ is selected from the group consisting of:
(i) —$(CH_2)_p CH_3$ wherein p is an integer from 16 to 29;
(ii) —$(CH_2)_p$-M-$(CH_2)_q$—$CH_3$, wherein M is CH=CH or C≡C and p and q are integers from 0 to 27, with the proviso that $14 \leq p+q \leq 27$;
(iii) —$(CH_2)_p$—K—$(CH_2)_q$-M-$(CH_2)_r$—$CH_3$, wherein K and M are independently selected from CH=CH and C≡C, and p, q and r are integers from 0 to 25, with the proviso that $12 \leq p+q+r \leq 25$;
(iv) —$(CH_2)_p$—K—$(CH_2)_q$-M-$(CH_2)_r$—P—$(CH_2)_s$—$CH_3$, wherein K, M and P are independently selected from CH=CH and C≡C, and p, q, r and s are integers from 0 to 23, with the proviso that $10 \leq p+q+r+s \leq 23$; and
(v) —$(CH_2)_p$—C≡C—C≡C—$(CH_2)_q$—$CH_3$, wherein p and q are integers from 0 to 26 with the proviso that $13 \leq p+q \leq 26$.

In some more specific embodiments, the invention relates to a compound of formula (I) wherein $R_1$ is —$(CH_2)_p$—K—$(CH_2)_q$-M-$(CH_2)_r$—$CH_3$, wherein K and M are C≡C and q is 0.

In some other embodiments, $M_1$, $M_2$ and $M_3$ are independently selected from the group consisting of Man α, Man α(1->2)Man α, Man α(1->3)Man α, Man α(1->4)Man α and Man α(1->6)Man α.

The invention further relates to a compound of formula (I) wherein $Q_1$, $Q_2$ and $Q_3$ are independently selected from the group of radicals of formula (II):

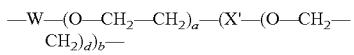

(II)

wherein:
W is selected from NH—$(CH_2)_f$, O—$(CH_2)_f$ and S—$(CH_2)_f$ wherein f is an integer from 1 to 5,
a is an integer from 2 to 10, preferably from 2 to 5,
b is 0 or 1,
d is an integer from 2 to 10, preferably 2 to 5, and
X' is —NH—C(O)—$(CH_2)_e$— or —O—C(O)—$(CH_2)_e$—, wherein e is an integer from 1 to 4.

In some embodiments, $M_2$-$Q_2$ and $M_3$-$Q_3$ are absent, and LINKER is —OC(O)—, —C(O)O—, —NHC(O)— or —C(O)NH—. In such an embodiment, b is preferably 1.

In some other embodiments $M_2Q_2$ and $M_3Q_3$ are present and are identical to $M_1$-$Q_1$ and LINKER is

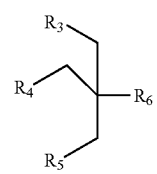

(VI)

wherein:
$R_6$ is —NHC(O)— or —OC(O)—, and
$R_3$, $R_4$ and $R_5$ are independently selected from —NHC(=O)$(CH_2)_n$O— and —OC(=O)$(CH_2)_n$O—, n being an integer from 1 to 10.

In some embodiments, the invention relates to a compound of the following formula (III):

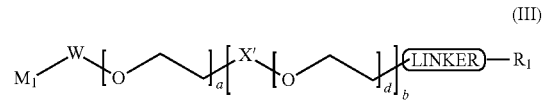

(III)

wherein:
LINKER is a bifunctional linker having a backbone of 1 to 20 carbon atoms and at least two heteroatoms independently selected from N, S and O,
$R_1$ is a $C_{17}$-$C_{30}$ saturated or unsaturated linear alkyl, optionally substituted by one or more $C_1$-$C_3$ alkyl radicals,
$M_1$ is mannosyl or dimannosyl,
W is selected from —NH—$(CH_2)_f$, —O—$(CH_2)_f$ — and —S—$(CH_2)_f$—, wherein f is an integer from 1 to 5, preferably 2,
X' is —NH—C(O)—$(CH_2)_e$— or —O—(O)—$(CH_2)_e$—, wherein e is an integer from 1 to 4,
a is an integer from 2 to 10, preferably from 2 to 5,
b=1, and
d is an integer from 2 to 10, preferably from 2 to 5, or a pharmaceutically acceptable salt or solvate thereof.

In some other embodiments, the invention relates to a compound of formula (V):

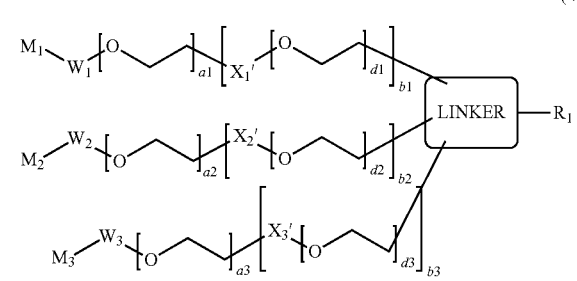

(V)

wherein:
LINKER is a tetrafunctional linker having a backbone of 1 to 20 carbon atoms and comprising at least two heteroatoms independently selected from N, S and O,
$R_1$ is a $C_{17}$-$C_{30}$ saturated or unsaturated linear alkyl, optionally substituted by one or more $C_1$-$C_3$ alkyl radicals,
$M_1$ is mannosyl or dimannosyl,
$M_2$ et $M_3$ are independently selected from the group consisting of mannosyl, dimannosyl and therapeutic agent moieties, preferably anti-infectious agent moieties, having a molecular weight of at most 800 g/mol$^{-1}$,
$W_1$, $W_2$ and $W_3$ are independently selected from —NH—$(CH_2)_f$, —O—$(CH_2)_f$— and —S—$(CH_2)_f$—, wherein f is an integer from 1 to 5, preferably 2,
$X'_1$, $X'_2$ and $X'_3$ are independently selected from X' as described above in formula (II), namely from the group consisting of —NH—C(O)—$(CH_2)_e$— and —O—C(O)—$(CH_2)_e$—, wherein e is an integer from 1 to 4,
a1, a2, a3, d1, d2 and d3 are integers independently selected from integers ranging from 2 to 10, preferably from 2 to 5, and
b1, b2 and b3 are independently selected from 0 and 1, or a pharmaceutically acceptable salt or solvate thereof.

In a more specific embodiment, the invention relates to a compound selected from the group consisting of compounds of formula (IIIa):

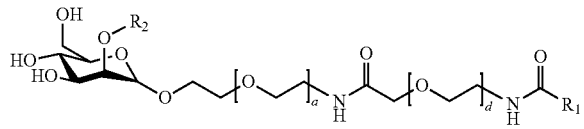

(IIIa)

wherein:
$R_2$ is H or α-mannosyl residue,
$R_1$ is as defined for a compound of formula (I),
a is an integer from 2 to 10, preferably from 2 to 5, and
d is an integer from 2 to 10, preferably from 2 to 5.

In another specific embodiment, the invention relates to a compound selected from the group consisting of compounds of formula (Va):

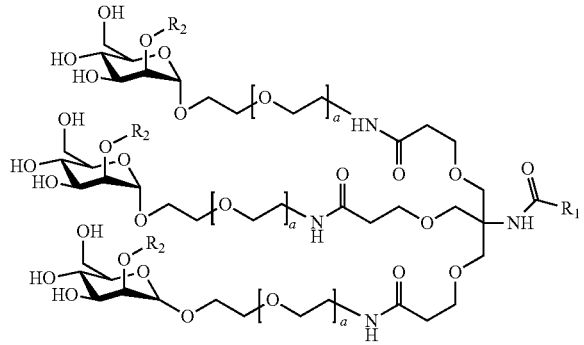

(Va)

wherein:
$R_2$ is H or α-mannosyl residue,
$R_1$ is as defined hereabove for a compound of formula (I), and
a is an integer from 1 to 10, preferably from 1 to 5.

More specifically, a compound of the invention may be selected from the group consisting of:
a compound of formula (IIIa), wherein $R_2$ is H, $R_1$ is —$(CH_2)_{16}CH_3$, a is 3 and b is 4;
a compound of formula (IIIa), wherein $R_2$ is H, $R_1$ is —$(CH_2)_{23}CH_3$, a is 3 and b is 4;
a compound of formula (IIIa), wherein $R_1$ is —$(CH_2)_8$—C≡C—C≡C—$(CH_2)_{11}$—$CH_3$, $R_2$ is H, a is 3, and b is 4;
a compound of formula (Va), wherein $R_1$ is —$(CH_2)_{23}CH_3$, $R_2$ is H, and a is 3;
a compound of formula (Va), wherein $R_1$ is —$(CH_2)_{23}CH_3$, $R_2$is α-mannosyl, and is H, a is 3 and b is 4;
a compound of formula (Va), wherein, $R_1$ is —$(CH_2)_8$—C≡C—C≡C—$(CH_2)_{11}$—$CH_3$, $R_2$ is H, and a is 3; and
a compound of formula (Va), wherein, $R_1$ is —$(CH_2)_8$—C≡C—C≡C—$CH_2)_{11}$—$CH_3$, $R_2$ is α-mannosyl and a is 3.

In a further aspect, the invention relates to any of the above-disclosed compounds for use as a drug, preferably for preventing or treating an infectious disease. Said infectious disease may be caused by a pathogen selecting from the group consisting of bacteria such as *Mycobacterium tuberculosis* and *Helicobacter pylori*, fungi such as *Candida albicans*, parasites such as Leishmania and viruses such as Ebola, Marburg, Human Immunodeficiency Virus (HIV), Hepatitis C Virus (HCV), Dengue, West Nile, Aura, Herpes simplex, severe acute respiratory syndrome (SARS) virus, measles, avian H5N1 influenza, and cytomegalovirus.

In some embodiments, the pathogen is selected from Immunodeficiency Virus (HIV), Hepatitis C Virus (HCV), Dengue Virus and Ebola virus.

Another object of the invention is a pharmaceutical composition comprising (i) a compound of the invention as an active ingredient, (ii) at least one pharmaceutically acceptable excipient and (iii) an optional therapeutic agent. Said pharmaceutical composition may be intended for mucosal delivery. The optional therapeutic agent may be an anti-HIV drug.

The invention also relates to a condom coated with a compound or with a pharmaceutical composition as defined above.

BRIEF DESCRIPTION OF THE DRAWINGS

FIG. 1A shows cell surface expression of DC-SIGN on monocytes and DCs, analyzed by flow cytometry. Black and grey histograms represent antigen staining and isotype controls, respectively. Values of mean fluorescence intensity (MFI) are indicated. Y -coordinate: counts, X-coordinate: fluorescence intensity.

FIG. 1B illustrates the interaction of gp120-FITC with monocytes and DCs, after incubation for 45 min at 37° C. (black histograms) by flow cytometry. Grey histograms represent untreated cells, in the presence of IgG1-FITC isotype control. Y-coordinate: counts, X-coordinate: fluorescence intensity.

FIG. 1C shows the binding competition of gp120-FITC with Mannan (middle chart) and with TriMan$_{C24}$ (right chart) on DCs by flow cytometry. Left chart shows control experiment wherein DCs are not exposed to TriMan$_{C24}$ or to Mannan. DCs were exposed to TriMan$_{C24}$ (100 μM) or mannan (100 μg/ml) for 30 min or left untreated, followed by incubation with gp120-FITC for 45 min at 37° C. In the middle and right charts, empty histograms correspond to cells binding gp120-FITC, in the absence of pretreatment (i.e., pretreatment with mannan or with TriMan$_{C24}$) and filled histograms show cells binding gp120-FITC, in the presence of pretreatment. Results are from one representative experiment repeated three times. Values of mean fluorescence intensity (MFI) are indicated. Y-coordinate: counts, X-coordinate: fluorescence intensity.

DCs were pretreated with the indicated compounds for 30 min at 37° C., and then infected with HIV-1 (R5 or X4 as indicated). After extensive washes, DCs were co-cultivated with MAGI-CCR5 cells for 2 days. Viral trans-infection was quantified by enumerating blue cells by light microscopy. Values were normalized relative to 100% infection obtained with medium alone. Values are means +/− SE from data obtained at least from three independent experiments.

Figure 2:
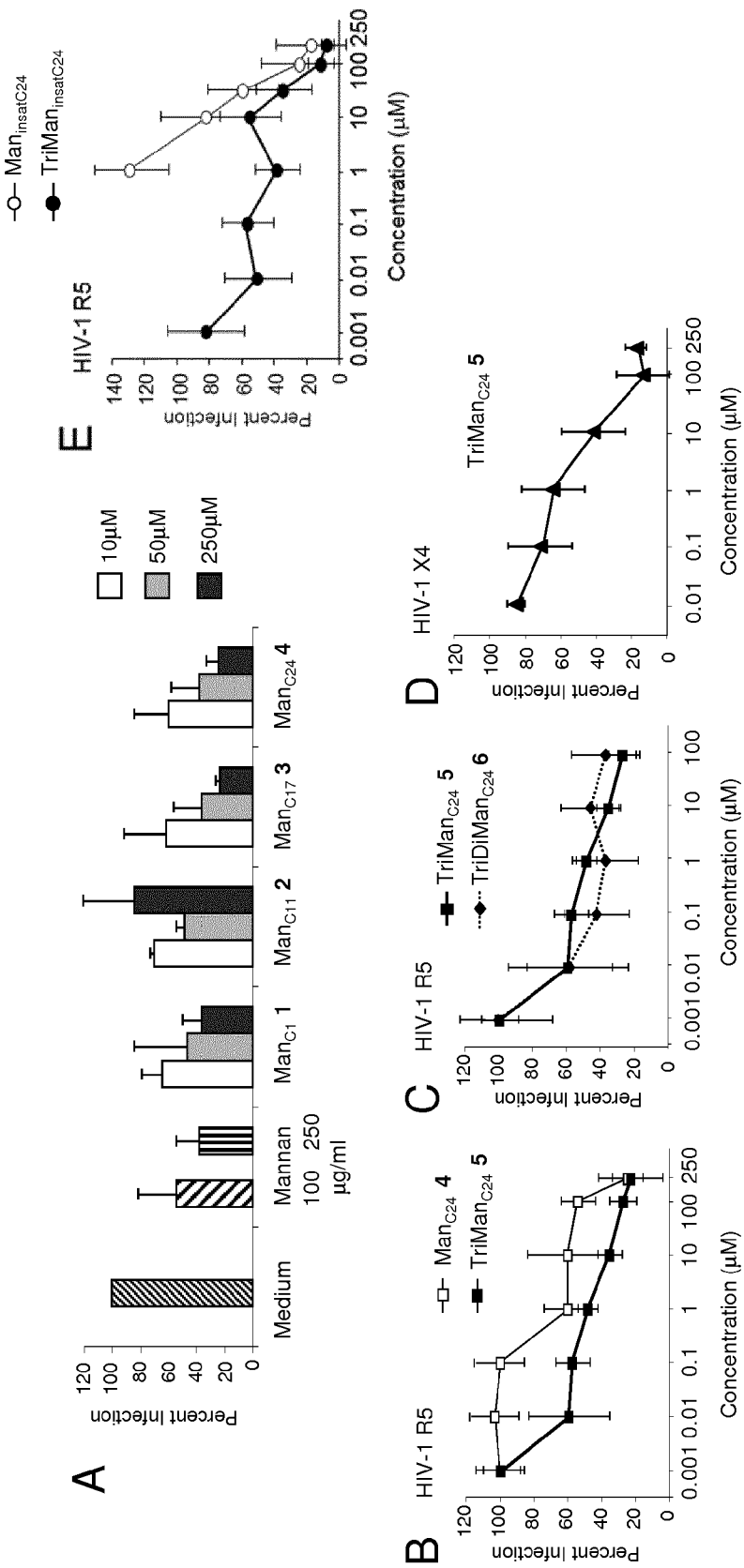
FIG. 2 Inhibition of HIV-1 Trans-Infection Mediated by DCs

FIG. 2A shows the relative percentage of trans-infection of MAGI-CCR5 cells incubated with DCs previously exposed to HIV-1 in the absence or presence of a compound of interest. From left to right: Medium (no compound added): negative control, Mannan at 100 µg/ml, Mannan at 250 µg/ml (positive control), $Man_{C1}$ (comparative) at 10 µM (white bar), at 50 µM (grey bar), at 250 µM (black bar), $Man_{C11}$ (comparative) at 10 µM (white bar), at 50 µM (grey bar), at 250 µM (black bar), $Man_{C17}$ (inventive) at 10 µM (white bar), at 50 µM (grey bar), at 250 µM (black bar) and $Man_{C24}$ (inventive) at 10 µM (white bar), at 50 µM (grey bar), and at 250 µM (black bar). Y-coordinate: relative percentage of trans-infection as compared to negative control.

FIG. 2B shows the dose-response curve concerning the relative percentage of trans-infection of MAGI-CCR5 by HIV-1 R5 when DCs were pre-incubated with $Man_{C24}$ (empty squares) or with $TriMan_{C24}$ (filled squares). Y-coordinate: relative percentage of trans-infection, X-coordinate: concentration of the compound in µM.

FIG. 2C shows the dose-response curve concerning the relative percentage of trans-infection of MAGI-CCR5 by HIV-1 R5 when DCs were pre-incubated with $TriMan_{C24}$ (filled squares) or with $TriDiMan_{C24}$ (filled rounds). Y-coordinate: relative percentage of trans-infection, X-coordinate: concentration of the compound in µM.

FIG. 2D shows the dose-response curve concerning the relative percentage of trans-infection of MAGI-CCR5 by HIV-1 X4 when DCs were pre-incubated with $TriMan_{C24}$. Y-coordinate: relative percentage of trans-infection, X-coordinate: concentration of the compound in µM.

FIG. 2E shows the dose-response curve concerning the relative percentage of trans infection of MAGI-CCR5 by HIV-1 R5 when DCs were pre-incubated with $TriMan_{insatC24}$ (filled rounds) or with $Man_{insatC24}$ (filled rounds). Y-coordinate: relative percentage of trans-infection, X-coordinate: concentration of the compound in µM.

Figure 3:
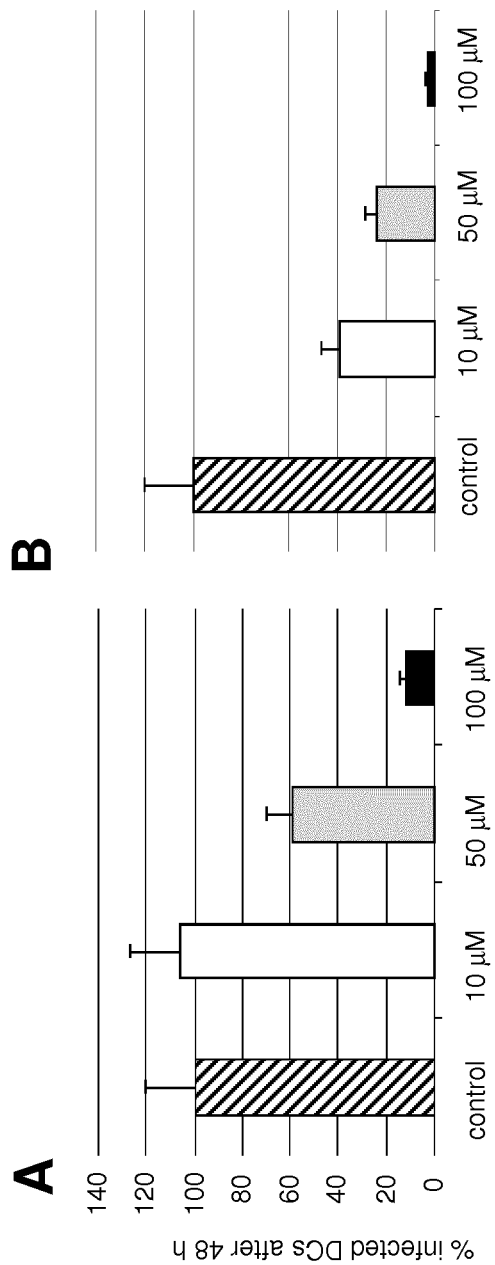

FIG. 3 Inhibition of Dengue Virus Cis-Infection of DCs by $TriMan_{insatC24}$

Human DCs were pre-treated with different concentrations of compounds or culture medium alone, for 30 min at 37° C. They were then exposed to Dengue virus 2 (DV2) for 2 hours at 37° C. Cells were washed to remove excess virions and compounds, and further cultured either in the absence (condition 1) or in the presence (condition 2) of $TriMan_{insatC24}$. After 48 hours, cells were subjected to intracellular detection of viral antigens.

FIG. 3A shows the relative percentage of infected DCs which were incubated in the absence or in the presence of $TriMan_{insatC24}$ in condition 1. From left to right: negative control (no compound added) (dashed bar), incubation with 10 µM $TriMan_{insatC24}$ (white bar), 50 µM $TriMan_{insatC24}$ (grey bar) and 100 µM $TriMan_{insatC24}$ (black bar). Y-coordinate: relative percentage of infected DCs as compared to negative control.

FIG. 3B shows the relative percentage of infected DCs which were incubated in the absence or in the presence of $TriMan_{insatC24}$ in condition 2. From left to right: negative control (no compound added) (dashed bar), incubation with 10 µM $TriMan_{insatC24}$ (white bar), 50 µM $TriMan_{insatC24}$ (grey bar) and 100 µM $TriMan_{insatC24}$ (black bar). Y-coordinate: relative percentage of infected DCs as compared to negative control.

FIG. 4 Synthesis Schemes

Figure 4A:
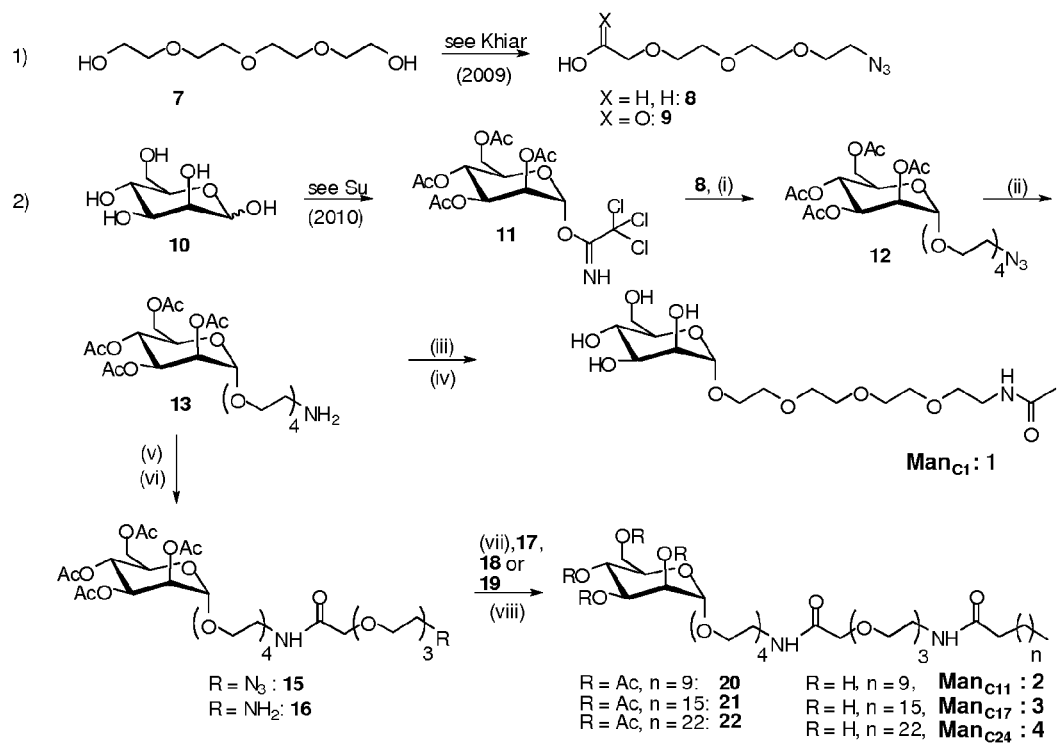

FIG. 4A Synthesis of $Man_{C1}$, $Man_{C11}$, $Man_{C17}$ and $Man_{C24}$. Conditions: (i) TMSOTf, DCM, 0° C. to RT, overnight, 47%; (ii) $PPh_3$, THF, $H_2O$, RT, overnight, 81%; (iii) CH3COCl, THF, 0° C., overnight, 25%; (iv) $NaOCH_3$, MeOH, RT, quantitative yield; (v) DCC, HOBT, THF, reflux, overnight, 9, (14%); (vi) $PPh_3$, THF, $H_2O$, RT, overnight, (49%); (vii) DCC, HOBT, THF, reflux, overnight; lauric acid 17 (98%); stearic acid 18 (78%), pentacosanoic acid 19 (88%); (viii) $NaOCH_3$, MeOH, RT, overnight, quantitative yield.

Figure 4B:
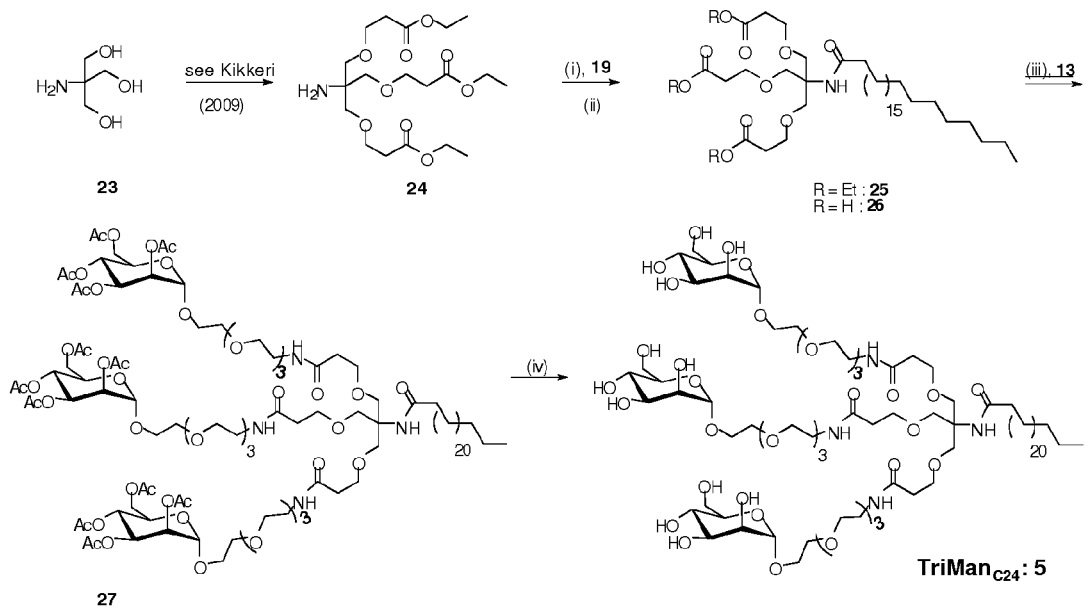

FIG. 4B Synthesis of trivalent mannoside $TriMan_{C24}$. Conditions: (i) Pentacosanoic acid 19, HOBt, DCC, THF, reflux, overnight, (77%); (ii) NaOH 4N, THF/EtOH, RT, overnight, (94%); (iii) HOBt, HBTU, THF, DIPEA, reflux, overnight, (63%); (iv) NaOCH3, MeOH, RT, overnight, quantitative yield.

Figure 4C:
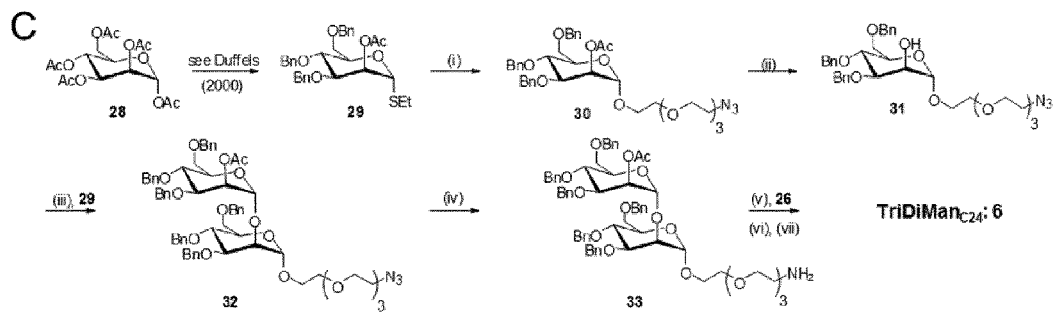

FIG. 4C Synthesis of trivalent dimannoside $TriDiMan_{C24}$. Conditions: (i) 8, TMSOTf, NIS, MS 4A, DCM, RT, overnight, (76%); (ii) $K_2CO_3$ (cat), MeOH, RT, overnight, 96%; (iii) 29, TMSOTf, NIS, MS 4A, DCM/Et20, RT, overnight, (58%); (iv) $PPh_3$, THF, $H_2O$, RT, overnight, (61%); (v) 26, HOBt, HBTU, DIPEA, THF, reflux, overnight, (27%); (vi) $K_2CO_3$ (cat), MeOH, RT, overnight, quantitative yield; (vii) $H_2$, $Pd(OH)_2/C$, MeOH, RT, overnight, (97%).

Figure 4D:
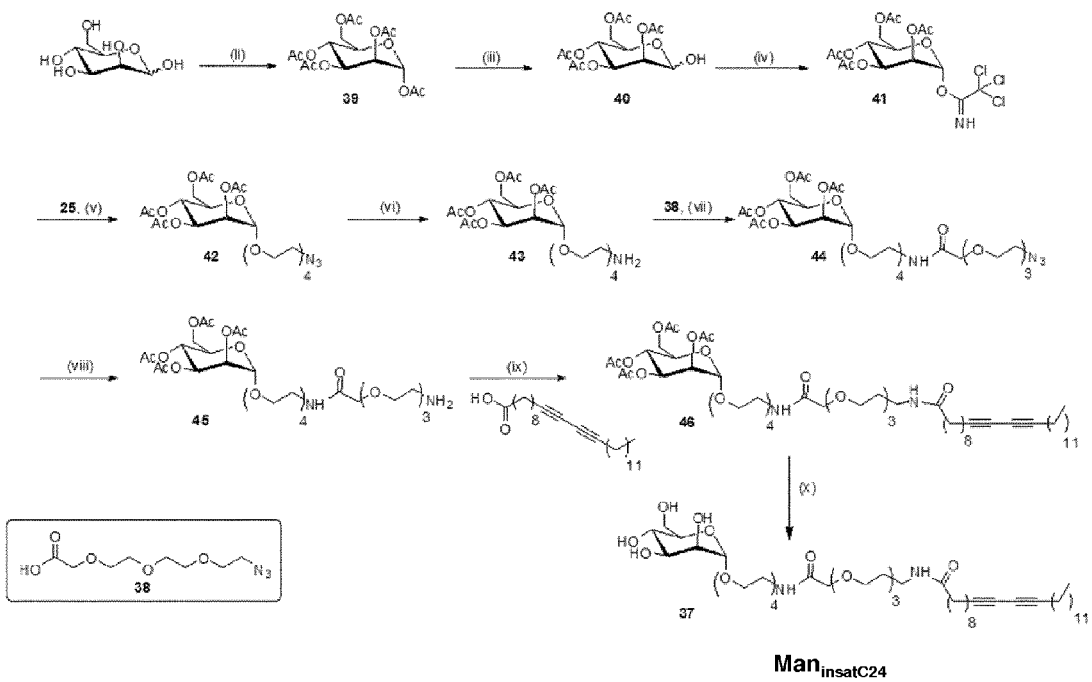

FIG. 4D Synthesis of $Man_{insatC24}$. Conditions: 60%; (i) $Ac_2O$, $NEt_3$, AcOEt, DMAP (cat), TA, 2 h, 93%; (ii) $BnNH_2$, THF, TA, 14 h, 66%; (iii) $Cl_3CCN$, DBU, DCM, TA, 14 h, 69%; (iv) TMSOTf, DCM, −50° C. to TA, 18 h, 47%; (v) $PPh_3$, THF, TA, 16 h, 81%; (vi) HOBt, DCC, THF, reflux, 16 h, 14%; (vii) $PPh_3$, THF, TA, 16 h, 49%; (viii) HOBt, DCC, THF, reflux, 18 h, 60%; (ix) $NaOCH_3$, MeOH, TA, 14 h, 91%.

Figure 4E:
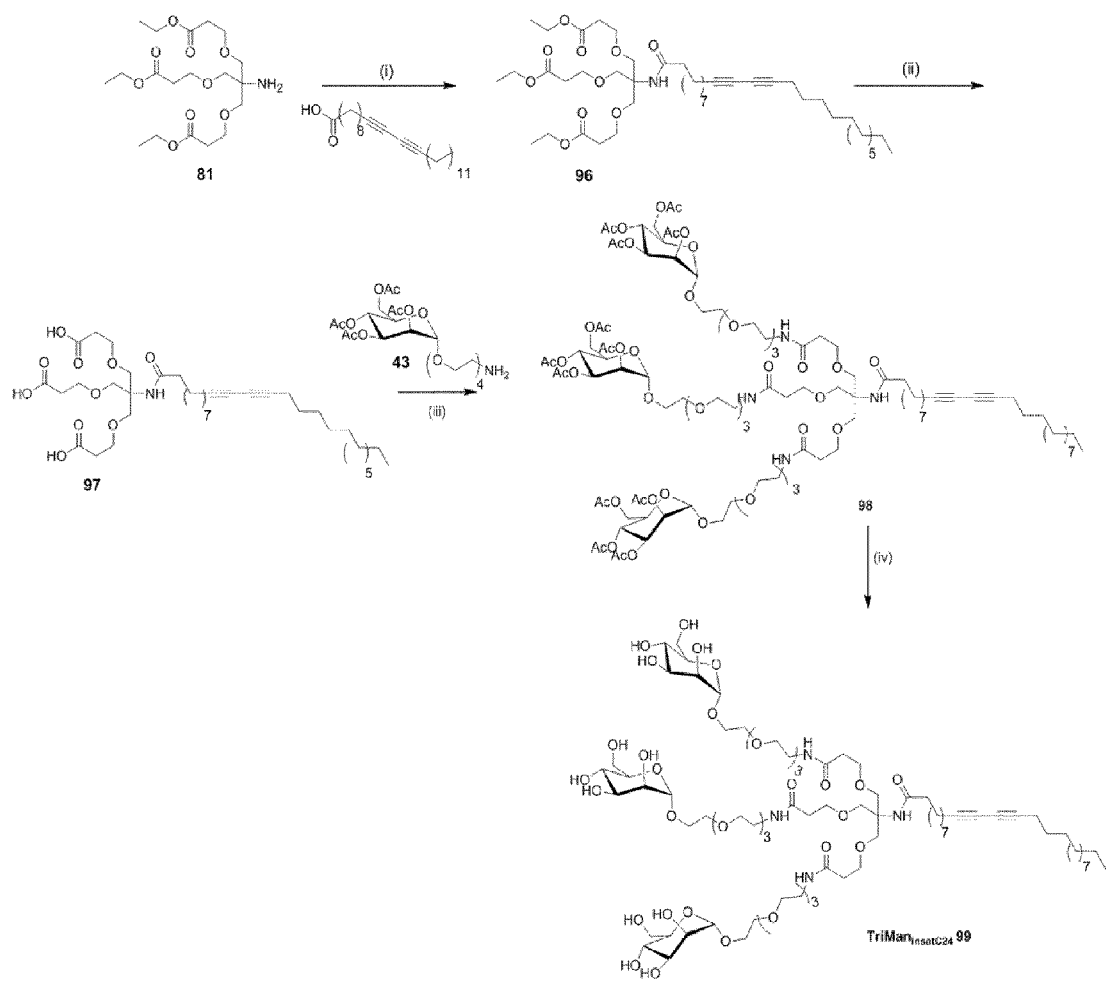

FIG. 4E Synthesis of $TriMan_{insatC24}$. Conditions: (i) HOBt, DCC, THF/MeCN, reflux, 16 h, 57%; (ii) NaOH 4N, THF/EtOH, TA, 14 h, 94%; (iii) HOBt, HBTU, THF, DIPEA, reflux, 16 h, 65%; (iv) $NaOCH_3$, MeOH, TA, 18 h, quantitative yield.

Figure 4F:
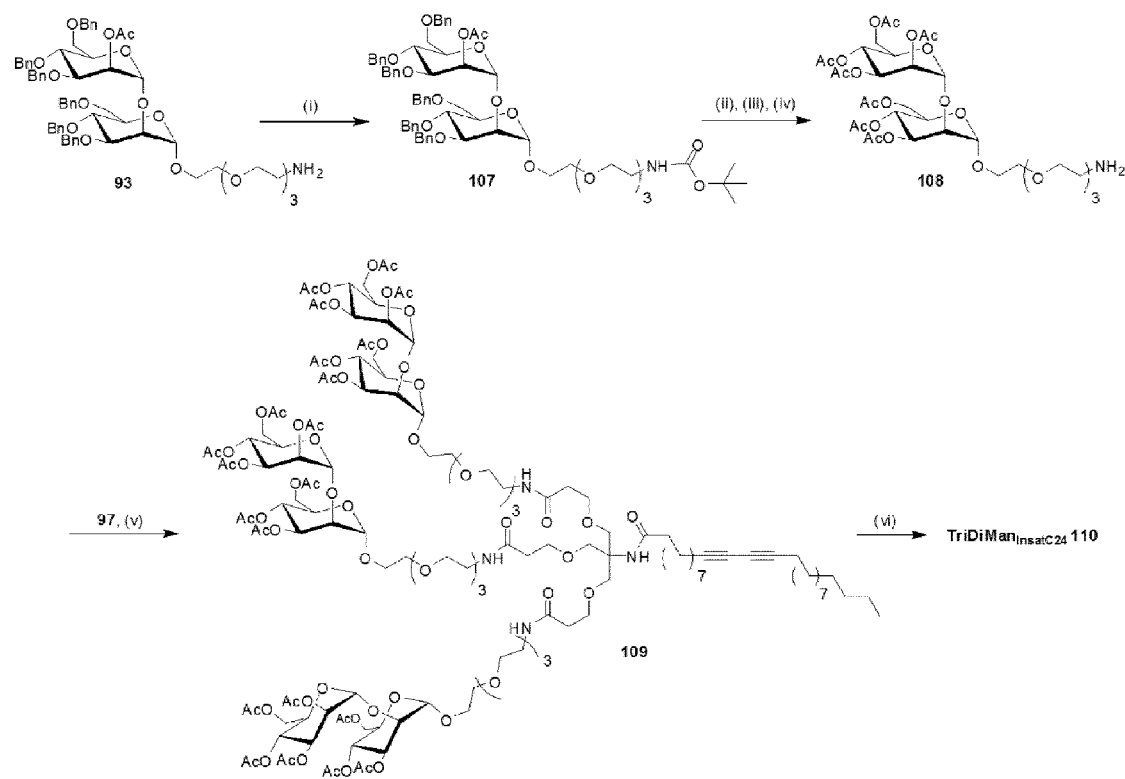

FIG. 4F Synthesis of $TriDiMan_{insatC24}$. Conditions: (i) $Boc_2O$, THF, TA, 14 h, 83%; (ii) $H_2$, $Pd(OH)_2/C$, MeOH, TA, 18 h; (iii) $Ac_2O$, NEt3, DMAP, TA, 14 h; (iv) TFA, DCM, 0° C. puis TA, 14 h; (v) HOBt, HBTU, THF, reflux, 16 h, 15%; (vi) $K_2CO_3$ (cat), MeOH, TA, 16 h, quantitative yield.

Figure 5:
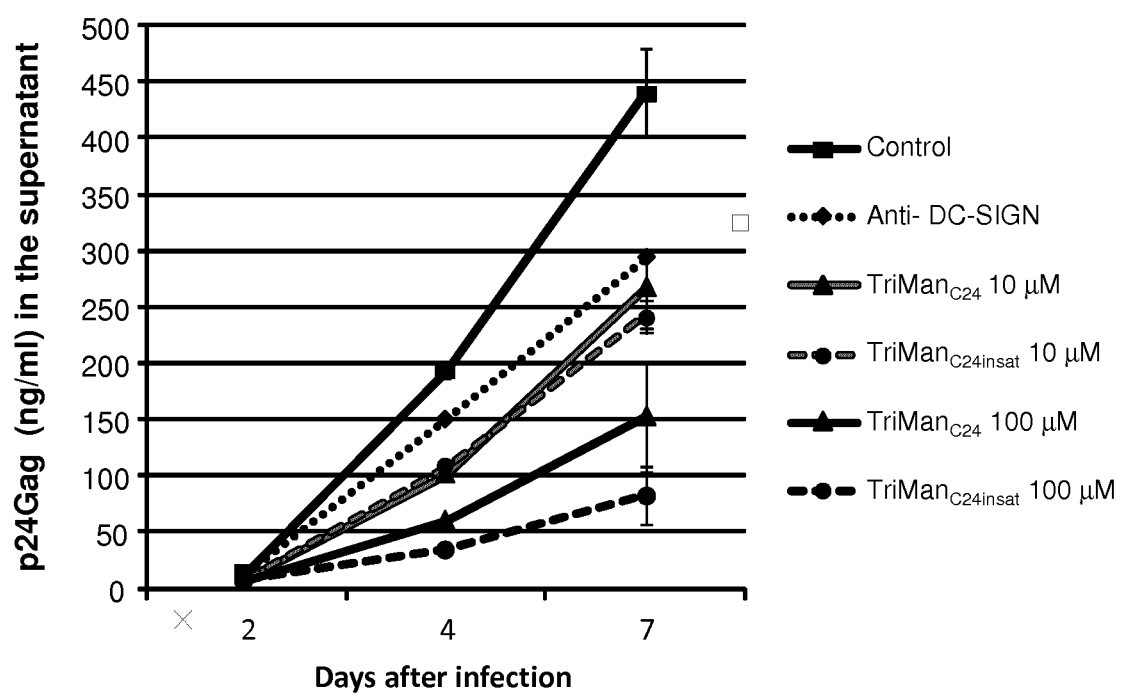

FIG. 5 Effect of Trimannoside Glycolipids on HIV-1 R5 Cis Infection in Dendritic Cells (DCs)

Values are means ± SE from data obtained from two independent experiments (two different human monocyte donors) performed in duplicate. From the bottom to the top: $TriMan_{C24insat}$ 100 µM, $TriMan_{C24}$ 100 µM, $TriMan_{C24insat}$ 10 µM, $TriMan_{C24}$ 10 µM, anti-DC -SIGN, Control. Y-coordinate: p24Gag levels (ng/ml) detected in the supernatant. X-coordinate: number of days after infection.

DETAILED DESCRIPTION OF THE INVENTION

The present invention provides new amphiphilic compounds displaying a high affinity for DC-SIGN, which may be used as anti-infectious agents for the prevention and the treatment of infectious diseases, including HIV infection. Said compounds comprise (i) a polar head having from one to three mannosyl or dimannosyl moieties, coupled to (ii) a single lipid chain of at least 17 carbons through (iii) an appropriate linker.

Surprisingly, the Applicant showed that a scaffold offering a multivalent mannose presentation so as to mimic the high-mannose structure occurring in glycoproteins was not required for obtaining compounds having a high binding affinity for DC-SIGN.

In this respect, the Applicant showed that the affinity of a mannose moiety for the extracellular domain of DC-SIGN can be drastically increased by coupling said mannose moiety to a lipid chain of at least 17 carbons. As illustrated in the experimental part, $Man_{C1}$ and $Man_{C11}$, which consist of a single alpha-D-mannose moiety linked to a $C_1$-chain and a $C_{11}$-chain respectively, failed to bind to the carbohydrate recognition domain (CRD) of DC-SIGN (see Table 1 of the experimental part below). On the contrary, $ManC_{17}$ and $ManC_{24}$, which consist of a single alpha-D-mannose moiety linked to a $C_{17}$-chain and $C_{24}$-chain respectively, were shown to have a dissociation constant (Kd) for DC-SIGN CRD of about $10^2$ µM and $10^{-1}$ µM, respectively.

Sub-micromolar Kds for DC-SIGN were also observed for compounds $TriMan_{C24}$ and $TriDiman_{C24}$, which correspond to compounds having (i) a branched polar head comprising three mannose moieties or three dimannose moieties, respectively, and (ii) a $C_{24}$ lipid chain. It was also shown that the $Triman_{C24}$ compound competed for the binding of soluble gp120 glycoprotein to DC-SIGN expressed on dendritic cells.

Such results underline a correlation between (i) the lipid chain length of the compounds and (ii) their ability to bind the CRD of DC-SIGN.

Noticeably, the high affinity of the compounds of the invention for DC-SIGN in vitro correlates with their antiviral activity in vitro.

In this respect, the Applicant showed that $Man_{C17}$ and $Man_{C24}$ inhibited in a dose-dependent manner the trans-infection of MAGI-CCR5 cells by human dendritic cells exposed to HIV-1 virions (in the presence of said compounds). Similar results were obtained for $Triman_{C24}$, $Triman_{insatC24}$, and $TriDiman_{C24}$. For these five compounds, the $IC_{50}$ ranged from $10^2$ µM to $10^{-2}$ µM. On the contrary, $Man_{C1}$ and $Man_{C11}$ exerted a very low inhibition on HIV trans-infection in vitro (see FIG. 2).

The Applicant also showed that $TriMan_{insatC24}$ and $TriMan_{C24}$ inhibit the cis-productive infection of DCs by Dengue virus and by HIV-1 virions.

The Applicant further showed that the compounds of the invention are soluble in water and display low (and even no) cellular toxicity.

Without to be bound by any theory, the Applicant believes that the biological activities of the compounds of the invention—namely their ability to bind the CRD of DC-SIGN and to inhibit HIV-1 trans-infection—mainly result from a cooperation between (i) their lipid chains and (ii) their mannose moieties.

Noticeably, all the compounds of the invention display biological activities at concentrations below their critical micelle concentration (CMC), which is in the range of $10^2$ µM. The Applicant strongly believes that the compounds of the invention interact directly with DC-SIGN as single molecules, without necessarily self-assembling into micelles so as to provide a multivalent mannose presentation.

In other words, the Applicant strongly believes that the compounds of the invention do not need to self-assemble into micelles to exert their biological activities.

I. Compounds of the Invention

The present invention relates to a compound consisting of:
(i) a polar head having from one to three mannose, dimannose or trimannose moieties, which is coupled through an appropriate linker to
(ii) a single lipid chain of at least 17 carbon atoms of length.

In a more specific aspect, the present invention relates to a compound of formula (I) or a pharmaceutically acceptable salt, solvate or derivative thereof,

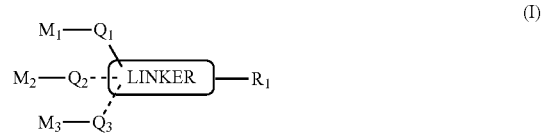

wherein:
$R_1$ is a $C_{17}$-$C_{30}$ saturated or unsaturated linear alkyl optionally substituted by one or more $C_1$-$C_3$ alkyl radicals,
$M_2$-$Q_2$ and $M_3$-$Q_3$ are optionally present,
$M_1$ is selected from the group consisting of mannosyl, dimannosyl and trimannosyl,
$M_2$ et $M_3$ are independently selected from the group consisting of mannosyl, dimannosyl, trimannosyl and therapeutic agent moieties, preferably anti-infectious agent moieties, having a molecular weight of at most 800 g/mol$^{-1}$,
$Q_1$, $Q_2$ and $Q_3$ are independently selected from the group of oligoether-based spacers comprising at least one —$(OR_8)_n$-moiety, wherein $R_8$ is a linear or branched $C_1$-$C_4$ alkyl and n is an integer from 2 to 10, and
LINKER is selected among bifunctional, trifunctional and tetrafunctional linkers having a backbone of 1 to 20 carbon atoms and at least two heteroatoms independently selected from N, S and O.

"$M_2$-$Q_2$ and $M_3$-$Q_3$ are optionally present" denotes that $M_2$-$Q_2$ and $M_3$-$Q_3$ are optional radicals, which means that compounds of formula (I) have one of the following formulae (Ia), (Ib) and (Ic):

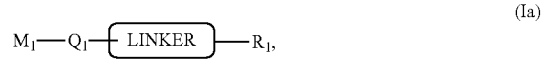

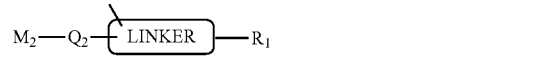

LINKER denotes any appropriate linker enabling to link $R_1$ with $M_1Q_1$ and, optionally with $M_2Q_2$ and/or $M_3Q_3$.

LINKER denotes a bifunctional linker in formula (Ia), a trifunctional linker in formula (IIa) and a tetrafunctional linker in formula (IIa).

Preferably, LINKER is not an organophosphate nor —(CH$_2$—CH$_2$—O)$_m$—, wherein m is an integer from 1 to 10.

As a bifunctional agent, LINKER may be selected from the group consisting of amino acid residues, peptides, —NH—C(=O)—, —C(=O)—NH—, —O—C(=O)—, —C(=O)—O—, —NH—(C=NH)—NH—, —NH—(C=O)—NH—, —(C=O)—O—(C=O)— and X$_1$—(CH$_2$)$_n$—Y$_1$, wherein (i) n is an integer from 1 to 10 and (ii) X$_1$ and Y$_1$ are independently selected from —NH—, —S—, —C(=O), —O—, —NH—C(=O)—, —C(=O)—NH—, —O—C(=O)—, —C(=O)—O—, —NH—(C=NH)—NH, —NH—(C=O)—NH— and —(C=O)—O—(C=O)—.

As used herein, "by an amino acid residue" is meant any one of the 20 naturally occurring amino acids as well as non-natural analogues. Amino acid residues encompass glycine, alanine, valine, leucine, isoleucine, methionine, phenylalanine, tryptophan, proline, serine, threonine, cysteine, tyrosine, asparagine, glutamine, aspartic acid, glutamic acid, lysine, arginine and histidine residues. In some embodiments, the amino acid residue is selected from alanine, valine and glycine.

As used herein, a peptide comprises from 2 to 10 amino acid residues, more preferably from 2 to 5 amino acid residues.

As a trifunctionnal linker, LINKER may be selected from compounds having a branched backbone having from 1 to 20 carbon atoms and at least three functional groups selected from —NH—, —S—, —C(=O)—, —O—, —NH—C(=O)—, —C(=O)—NH—, —O—C(=O)—, —C(=O)—O—, —NH—(C=NH)—NH—, —NH—(C=O)—NH— and (C=O)—O—(C=O).

For example, LINKER may be selected from the group consisting of amino acid residues such as arginine, lysine, aspartate, glutamate, glutamine, asparagine, serine and threonine, as well as peptides having from 2 to 10 amino acid residues, preferably from 2 to 5 amino acid residues.

As a tetrafunctional linker, LINKER may be selected from compounds having a branched backbone having from 1 to 20 carbon atoms and at least four functional groups selected from NH—, —S—, —C(=O)—, —O—, —NH—C(=O)—, —C(=O)—NH—, —O—C(=O)—, —C(=O)—0—, —NH—, —C(=NH)—NH—, —NH—C(=O)—NH— and —C(=O)—O—C(=O)—, preferably from —NH—, —NHC(O)—, —C(O)NH—, —OC(O)—, —C(O)O— and —O—.

For example, LINKER may be selected from peptides having from 2 to 10 amino acids, preferably from 2 to 5 amino acid residues. For example, LINKER may be selected from dipeptide radicals comprising amino acids selecting from lysine, arginine, aspartate, glutamate, glutamine, asparagine, serine and threonine. LINKER may be also selected from tromethamine, glycerol, and pentaerythritol radicals and derivatives thereof.

As used herein, the term "solvate" or "pharmaceutically acceptable solvate" refers to a solvate formed from the association of one or more molecule of compounds according to the instant invention with one or more molecules of solvent. The term "solvates" includes hydrates such as hemi-hydrate, monohydrate, dihydrate and the like.

As used herein, the term "derivative" or "pharmaceutical derivative" of compound of formula (I) refers to any compound derived from a compound of formula I by minor chemical modifications such as esterification and alkylation, e.g., methylation of one or several hydroxyl groups of mannosyl, and which displays similar biological activities in vivo as the said compound. As used herein, the term "derivative" encompasses esters, alkoxy derivatives and prodrugs of compounds of formula I.

In a preferred embodiment, the compound of the invention is selected from compounds of formula (I) and their pharmaceutically acceptable solvates, esters and salts.

As used herein, by "C$_{17}$-C$_{30}$ alkyl" is meant a linear hydrocarbon chain having from 17 to 30 carbons. A "C$_{17}$-C$_{30}$ alkyl" encompasses C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$ and C$_{30}$ alkyl.

By "C$_{17}$-C$_{30}$ saturated alkyl" is meant a linear hydrocarbon chain having from 17 to 30 carbons; said hydrocarbon chain does not comprise any unsaturation, i.e., any double or triple bonds.

By "C$_{17}$-C$_{30}$ unsaturated alkyl" is meant a linear hydrocarbon chain having from 17 to 30 carbons which comprises at least one unsaturation, i.e., at least one double bond and/or at least one triple bond. "At least one unsaturation" encompasses 1, 2, 3, 4, 5, 6, 7, 8, 9 and 10 unsaturations, preferably, 1, 2, 3 and 4 unsaturations In the case of a "C$_{17}$-C$_{30}$ unsaturated alkyl" comprising several unsaturations, each unsaturation may be a triple bond or a double bond; that is to say that a "C$_{17}$-C$_{30}$ unsaturated alkyl" encompasses (i) C$_{17}$-C$_{30}$ alkyls having at least one double bond and no triple bond, (ii) C$_{17}$-C$_{30}$ alkyls having at least one triple bond and no double bond and (iii) C$_{17}$-C$_{30}$ alkyls having at least one double bond and at least one triple bond. The double bonds present in a "C$_{17}$-C$_{30}$ alkyl" may have indifferently trans conformation (Z) or cis conformation (E).

As mentioned hereabove, the "C$_{17}$-C$_{30}$ saturated or unsaturated alkyl" may be substituted by one or more "C$_1$-C$_3$ alkyl radicals". By "C$_1$-C$_3$ alkyl radical" is meant methyl, ethyl, propyl or isopropyl. "One or more C$_1$-C$_3$ alkyl radicals" encompasses 1, 2, 3, 4, 5, 6, 7, 8, 9 and 10 C$_1$-C$_3$ alkyl radicals. Preferably, R$_1$ comprises at most three C$_1$-C$_3$ alkyl substituents, preferably selected from ethyl and methyl.

As used herein, by "mannosyl", "mannopyranosyl", or "Man" is meant the radical alpha-D-mannosyl. Accordingly, dimannosyl residue refers to dimers of alpha-D -mannosyl. Dimannosyl encompasses Man α(1−>2)Man α, Man α(1−>3)Man α, Man α(1−>4)Man α, Man α(1−>6)Man α. In the same way, trimannosyl refers to trimers of alpha-D-mannosyl and encompasses, without being limited to, Man α(1−>2)Man α(1−>2)Man α, Man α(1−>3)Man α(1−>3) Man α and Man α(1−>6)Man α(1−>6)Man α.

Preferably, dimannosyl is Man α(1−>2)Man radical and trimannosyl is Man α(1−>2)Man α(1−>2)Man α.

More precisely, as used herein, "mannosyl" refers to the following radical:

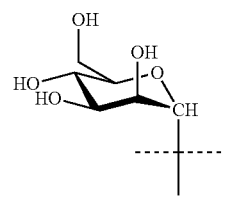

For example, Man α(1−>2)Man α radical refers to the following formula:

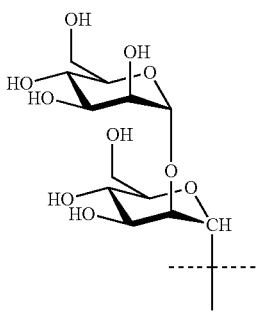

As used herein, by "therapeutic agent moiety" is meant a radical derived from a therapeutic agent molecule by minor chemical modifications that enable the introduction of an appropriate group for covalently binding said anti-infectious agent and the adjacent spacer $Q_2$ or $Q_3$ of the compound of formula (I).

As used herein, by "therapeutic agent" is meant any molecule that may be used for treating or preventing a disease, or for curing or diminishing symptoms associated with a disease as well as improving the general condition of a patient. Actually, "therapeutic agent" refers to any class of therapeutic molecules and thus encompasses, without being limited to, vitamins, anti-infectious agents, anti-tumoral agents, analgesic agents, anti-inflammatory agents, antidiabetic agents and the like.

A molecule having a molecular weight of at most 800 g.mol$^{-1}$ encompasses a molecule having a molecular weight of at most 200 g.mol$^{-1}$, of at most 300 g.mol$^{-1}$, of at most 400 g.mol$^{-1}$, of at most 500 g.mol$^{-1}$, of at most 600 g.mol$^{-1}$, or of at most 700 g.mol$^{-1}$.

As used herein, by "anti-infectious agent" is meant any compound which may be used for treating or preventing an infection caused by a pathogen such as a virus, a fungus, a bacterium or a parasite. The anti-infectious agents include, without being limited to, antibiotics and antiviral agents.

Antibiotics encompass, without being limited to, isoniazide, metronidazole, clarithromycin, fluoroquinolones such as ciprofloxacin, rifampicin, β-lactam antibiotics such as amoxicillin and carbapenems including imipenem.

Antiviral agents encompass, without being limited to, anti-hepatitis C agents such as boceprevir and ribavirin, and anti-HIV drugs. Anti-HIV drugs include (i) reverse transcriptase inhibitors such as tenofovir, zidovudine, didanosine, zalcitabine, stavudine, lamivudine, abacavir, amtricitabine, nevirapine, efavirenz, and delavirdine, (ii) protease inhibitors such as saquinavir, indinavir, ritonavir, nefinavir, amprenavir, lopinavir, atazanavir, fosamprenavir, darunavir and brecanavir, (iii) integrase inhibitors such as raltegravir and elvitegravir, (iv) antagonists of CCR5 chemokines such as maraviroc, vicriviroc, and aplaviroc, and (vi) maturation inhibitors such as bevirimat. For reviews concerning anti-HIV drugs see for example Flexner, *Nat. Rev. Drug Discov.* 2007, 6, 959-966, and de Clercq, E., *Nat. Rev. Drug Discov.* 2007, 6, 1001-1018.

As mentioned above, $Q_1$, $Q_2$ and $Q_3$ are independently selected from oligoether-based spacers, said spacers comprising at least one oligoether moiety of formula —(OR$_8$)$_n$—, wherein R$_8$ is a linear or branched $C_1$-$C_4$ alkyl and n is an integer from 2 to 10. "At least one oligoether" means that said spacer may comprise one or several radicals (OR$_8$)$_n$. In a preferred embodiment, $Q_1$, $Q_2$ and $Q_3$ are independently selected from oligoether-based spacers comprising from 1 to 5 (OR$_8$)$_n$ radicals, preferably from 1 to 5 —(O—CH$_2$—CH$_2$)$_n$— radicals.

Without being bound by any theory, the Applicant believes that the presence of oligo-ether based spacers enables the increase of the hydrophilic character of the compound of formula (I) while diminishing the steric effect on $M_1$, $M_2$ and/or $M_3$ moieties.

When $M_2Q_2$ and $M_3Q_3$ are absent, $Q_1$ contains from 1 to 5 —(O—CH$_2$—CH$_2$)$_n$—, preferably from 2 to 3 —(O—CH$_2$—CH$_2$)$_n$—, wherein n ranges from 2 to 10, preferably from 2 to 5.

When $M_2Q_2$ and/or $M_3Q_3$ are present, $Q_1$, $Q_2$ and $Q_3$ are independently selected from oligoether-based spacers containing from 1 to 5 —(O—CH$_2$—CH$_2$)$_n$—, preferably from 1 to 2 —(O—CH$_2$—CH$_2$)$_n$—, wherein n ranges from 2 to 10, preferably from 2 to 5.

In a first embodiment, the present invention relates to a compound of formula (I) wherein $R_1$ is selected from the group consisting of non-substituted, saturated and linear $C_{17}$-$C_{30}$ alkyls and non-substituted, unsaturated and linear $C_{17}$-$C_{30}$ alkyls. In other words, $R_1$ is selected from $C_{17}$-$C_{30}$ alkyls that comprise no substituent, in particular, no $C_1$-$C_3$ alkyl substituent. In some embodiments, the compound of the invention is selected from the compounds of formula (I) wherein $R_1$ is a linear and unsubstituted $C_{17}$-$C_{30}$ alkyl having from 0, 1 or 2 unsaturations.

In a more specific embodiment, the compound of the invention is selected from the compounds of formula (I) wherein $R_1$ is selected from the group consisting of:
(i) —(CH$_2$)$_p$CH$_3$, wherein p is an integer from 16 to 29;
(ii) —(CH$_2$)$_p$-M-(CH$_2$)$_q$—CH$_3$, wherein M is CH=CH or C≡C and p and q are integer from 0 to 27, with the proviso that 14≤p+q≤27;
(iii) —(CH$_2$)$_p$—K—(CH$_2$)$_q$-M-(CH$_2$)$_r$—CH$_3$, wherein K and M are independently selected from CH=CH and C≡C, and p, q and r are integers from 0 to 25, with the proviso that 12≤p+q+r≤25;
(iv) —(CH$_2$)$_p$—K—(CH$_2$)$_q$-M-(CH$_2$)$_r$—P—(CH$_2$)$_s$—CH$_3$, wherein K, M and P are independently selected from CH=CH and C≡C, and p, q, r and s are integers from 0 to 23, with the proviso that 10≤p+q+r+s≤23; and
(v) —(CH$_2$)$_p$—C≡C—C≡C—(CH$_2$)$_q$—CH$_3$, wherein p and q are integers from 0 to 26, with the proviso that 13≤p+q≤26.

As illustrated in the Examples, compounds of formula (I) having an $R_1$ radical comprising no unsaturation were particularly efficient at inhibiting HIV-1 trans infection in vitro. The Applicant also showed that compounds of formula (I) having an $R_1$ radical comprising two adjacent triple bonds (—C≡C—C≡C—) were able to inhibit HIV trans-infection in vitro with a very low IC$_{50}$ (half maximal inhibitory concentration). The same results are expected for compounds of formula (I) wherein $R_1$ comprises two adjacent double bonds (—C=C=C—).

Accordingly, in some specific embodiments, the compound of the invention is selected from compounds of formula (I) wherein $R_1$ is selected from the group consisting of:
a. —(CH$_2$)$_p$CH$_3$, wherein p is an integer from 16 to 29;
b. —(CH$_2$)$_p$—C≡C—C≡C—(CH$_2$)$_r$—CH$_3$, wherein p and r are integers from 0 to 25, with the proviso that 12≤p+r≤25; and
c. —CH$_2$)$_p$—C≡C=C—(CH$_2$)$_q$—CH$_3$, wherein p and q are integers from 0 to 26, with the proviso that 13≤p+q≤26.

In some other embodiments, $R_1$ is (CH$_2$)$_p$—C≡C—C≡C—(CH$_2$)$_r$—CH$_3$, wherein p and r are integers from 0 to 25, with the proviso that 12≤p+r≤25. Such $R_1$ correlates with radical as described above in item (iii) wherein q is equal to 0.

In some other embodiments, $R_1$ is selected from the group consisting of linear saturated or unsaturated $C_{20}$-$C_{30}$ alkyls. In such an embodiment, $R_1$ may be selected from the group consisting of:
  (i) —$(CH_2)_p CH_3$, wherein p is an integer from 19 to 29;
  (ii) —$(CH_2)_p$-M-$(CH_2)_q$—$CH_3$, wherein M is CH=CH or C≡C and p and q are integers from 0 to 27, with the proviso that 17≤p+q≤27;
  (iii) —$(CH_2)_p$—K—$(CH_2)_q$-M-$(CH_2)_r$—$CH_3$, wherein K and M are independently selected from CH=CH and C≡C, and p, q and r are integers from 0 to 25, with the proviso that 15≤p+q+r≤25;
  (iv) —$(CH_2)_p$—K—$(CH_2)_q$-M-$(CH_2)_r$—P—$(CH_2)_s$—$CH_3$, wherein K, M and P are independently selected from CH=CH and C≡C, and p, q, r and s are integers from 0 to 23, with the proviso that 13≤p+q+r+s≤23; and
  (v) —$(CH_2)_p$—C≡C—C—$(CH_2)_q$—$CH_3$, wherein p and q are integers from 0 to 26, with the proviso that 16≤p+q≤26.

In some further embodiments, $R_1$ is selected from the group consisting of linear saturated or unsaturated $C_{17}$-$C_{26}$ alkyls. In such an embodiment, $R_1$ may be selected from the group consisting of:
  (i) —$(CH_2)_p CH_3$, wherein p is an integer from 16 to 25;
  (ii) —$(CH_2)_p$-M-$(CH_2)_q$—$CH_3$, wherein M is CH=CH or C≡C and p and q are integers from 0 to 23, with the proviso that 14≤p+q≤23;
  (iii) —$(CH_2)_p$—K—$(CH_2)_q$-M-$(CH_2)_r$—$CH_3$, wherein K and M are independently selected from CH=CH and C≡C, and p, q and r are integers from 0 to 21, with the proviso that 12≤p+q+r≤21;
  (iv) —$(CH_2)_p$—K—$(CH_2)_q$-M-$(CH_2)_r$P—$(CH_2)_s$—$CH_3$, wherein K, M and P are independently selected from CH=CH and C≡C, and p, q, r and s are integers from 0 to 19, with the proviso that 10≤p+q+r+s≤19; and
  (v) —$(CH_2)_p$—C≡C—C—$(CH_2)_q$—$CH_3$, wherein p and q are integers from 0 to 22, with the proviso that 13≤p+q≤22.

As explained above, due to the lipophilic tail $R_1$, the presence of a high-mannose structure is not required for obtaining compounds with a high affinity for DC-SIGN and able to inhibit or prevent HIV trans-infection or dengue virus cis-infection.

Accordingly, in an additional embodiment, the present invention relates to a compound of formula (I) wherein:
$M_1$ is selected from the group consisting of Man α, Man α(1->2)Man α, Man α(1->3)Man α, Man α(1->4)Man α and Man α(1->6)Man α, and
When $M_2$ and/or $M_3$ are present, said radical(s) are selected from the group consisting of Man α, Man α(1->2)Man α, Man α(1->3)Man α, Man α(1->4)Man α, Man α(1->6) Man α and anti-infectious agent moieties, preferably anti-viral agent moieties, having a molecular weight of at most 800 g.mol$^{-1}$.

In an another embodiment, the compound of the invention is a compound of formula (I) wherein $M_1$ and the optional $M_2$ and $M_3$ are independently selected from the group consisting of Man α, Man α(1->2)Man α, Man α(1->3) Man α, Man α(1->4)Man α and Man α(1->6)Man α.

In a further embodiment, the compound of the invention is a compound of formula (I) wherein $M_1$ and the optional $M_2$ and $M_3$ are independently selected from Man α and Man α(1->2)Man α.

In some specific embodiments, the compound of formula (I) has all the following features:
  (i) $M_1$ is selected from the group consisting of Man α, Man α(1->2)Man α, Man α(1->3)Man α, Man α(1->4)Man α and Man α(1->6)Man α;
  (ii) When $M_2$ and/or $M_3$ are present, said $M_2$ and/or $M_3$ are selected from the group consisting of Man α, Man α(1->2)Man α, Man α(1->3)Man α, Man α(1->4) Man α, and Man α(1->6)Man α; and
  (iii) $R_1$ is selected from the group consisting of:
    —$(CH_2)_p CH_3$, wherein p is an integer from 16 to 29;
    —$(CH_2)_p$-M-$(CH_2)_q$—$CH_3$, wherein M is —CH=CH— or —C≡C— and p and q are integers from 0 to 27, with the proviso that 14≤p+q≤27;
    —$(CH_2)_p$—K—$(CH_2)_q$-M-$(CH_2)_r$—$CH_3$, wherein K and M are independently selected from —CH=CH— and —C≡C—, and p, q and r are integers from 0 to 25, with the proviso that 12≤p+q+r≤25;
    —$(CH_2)_p$—K—$(CH_2)_q$-M-$(CH_2)_r$—P—$(CH_2)_s$—$CH_3$, wherein K, M and P are independently selected from —CH=CH— and —C≡C—, and p, q, r and s are integers from 0 to 23, with the proviso that 10≤p+q+r+s≤23; and
    —$(CH_2)_p$—C≡C—C—$(CH_2)_q$—$CH_3$, wherein p and q are integers from 0 to 26, with the proviso that 13≤p+q<26.

In some other embodiments, the invention relates to a compound of formula (I) wherein $Q_1$ and, when present, $Q_2$ and $Q_3$ are independently selected from the group consisting of radicals of formula (II):

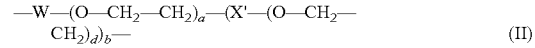

wherein:
W is selected from —NH—$(CH_2)_f$, —O—$(CH_2)_f$— and —S—$(CH_2)_f$—, wherein f is an integer from 1 to 5,
a is an integer from 2 to 10, preferably from 2 to 5,
b is 0 or 1,
d is an integer from 1 to 10, and
X' is —NH—C(O)—$(CH_2)_e$— or —O—C(O)—$(CH_2)_e$—, wherein e is an integer from 1 to 4.

In some other embodiments, the invention relates to a compound of formula (I) wherein $Q_1$ and, when present, $Q_2$ and $Q_3$ are independently selected from the group consisting of radicals of formula (II):

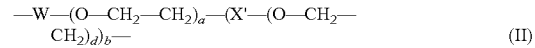

wherein:
W is selected from —NH—$(CH_2)_f$, —O—$(CH_2)_f$— and —S—$(CH_2)_f$—, wherein f is an integer from 1 to 5,
a is an integer from 2 to 10, preferably from 2 to 5,
b is 0 or 1,
d is an integer from 1 to 10, and
X' is —NH—C(O)—$(CH_2)_e$— or —O—C(O)—$(CH_2)_e$—, wherein e is an integer from 1 to 4, with the proviso that b is not 0 when $M_2 Q_2$ and $M_3 Q_3$ are absent.

An integer from 2 to 10 encompasses an integer equal to 2, 3, 4, 5, 6, 7, 8, 9 or 10. "b is 0" means that —(X'—O—$CH_2$—$CH_2$)$_d$— is absent.

In some specific embodiments, the compound of formula (I) has all the following features:
  (i) $M_1$ is selected from the group consisting of Man α, Man α(1->2)Man α, Man α(1->3)Man α, Man α(1->4)Man α and Man α(1->6)Man α;
  (ii) When $M_2$ and/or $M_3$ are present, said $M_2$ and/or $M_3$ are selected from the group consisting of Man α, Man α(1->2)Man α, Man α(1->3)Man α, Man α(1->4) Man α, and Man α(1->6)Man α;

(iii) $Q_1$ and, when present, $Q_2$ and $Q_3$ are independently selected from the group consisting of radicals of formula (II): —W—(O—CH$_2$—CH$_2$)$_a$—(X'(O—CH$_2$—CH$_2$)$_d$)$_b$—, wherein W, a, X', d and b are as previously described; and (iv) $R_1$ is selected from the group consisting of:
—(CH$_2$)$_p$CH$_3$, wherein p is an integer from 16 to 29;
—(CH$_2$)$_p$-M-(CH$_2$)$_q$—CH$_3$, wherein M is —CH=CH— or —C≡C— and p and q are integers from 0 to 27, with the proviso that 14≤p+q≤27;
—(CH$_2$)$_p$—K—(CH$_2$)$_q$-M-(CH$_2$)$_r$—CH$_3$, wherein K and M are independently selected from —CH=CH— and —C≡C—, and p, q and r are integers from 0 to 25, with the proviso that 12≤p+q+r≤25;
—(CH$_2$)$_p$—K—(CH$_2$)$_q$-M-(CH$_2$)$_r$—P—(CH$_2$)$_s$—CH$_3$, wherein K, M and P are independently selected from —CH=CH— and —C≡C—, and p, q, r and s are integers from 0 to 23, with the proviso that 10≤p+q+r+s≤23; and
—(CH$_2$)$_p$—C≡C—C≡C—(CH$_2$)$_q$—CH$_3$, wherein p and q are integers from 0 to 26, with the proviso that 13≤p+q≤26.

In a specific aspect, the present invention relates to a compound of formula (Ia), namely a compound of formula (I) wherein $M_2$-$Q_2$ and $M_3$-$Q_3$ are absent.

In some embodiments, the present invention relates to a compound of formula (III):

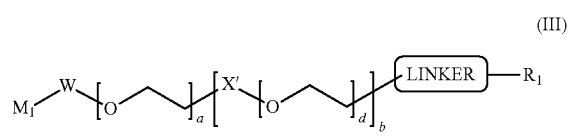

(III)

wherein $M_1$, W, a, X', d, b, LINKER and $R_1$ are as fully described hereabove.

Preferably, W is —O—CH$_2$—CH$_2$—. Preferably, b is 1.

As previously described, in such an embodiment, LINKER is a bifunctional linker which may be selected from the group consisting of:
(i) Amino acid residues such as glycine, alanine, valine, isoleucine, and leucine,
(ii) Peptides having from 2 to 10 amino acid residues, preferably from 2 to 5 amino acid residues,
(iii) $X_1$—(CH$_2$)$_n$—$Y_1$, wherein (i) n is an integer from 1 to 10 and (ii) $X_1$ and $Y_1$ are independently selected from —NH—, —S—, —C(=O)—, —O—, —NH—C(=O)—, —C(=O)—NH—, —O—C(=O)—, —C(=O)—O—, —NH—(C=NH)—NH—, —NH—(C=O)—NH— and (C=O)—O—(C=O); and
(iv) —NH—, —S—, —O—, —C(=O)—, —NH—C(=O)—, —C(=O)—NH—, —O—C(=O)—, —C(=O)—O—, NH—(C=NH)—NH—, —NH—(C=O)—NH— and —(C=O)—O—(C=O)—.

In some specific embodiments of the invention, LINKER is —O—C(=O)—, —C(=O)—O—, —NHC(=O)— or —C(=O)NH—, preferably —NHC(=O)— or —C(=O)NH— and, more preferably, —NHC(50 O)—.

In some more specific embodiments, the compound of the invention is selecting from compounds of formula (IIIa):

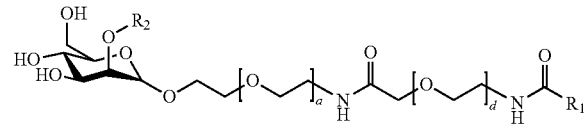

(IIIa)

wherein:
$R_2$ is H or α-mannosyl residue, preferably connected through (1->2) linkage,
$R_1$ is as fully-defined hereabove,
a is an integer from 2 to 10, preferably from 2 to 5, and
d is an integer from 2 to 10, preferably from 2 to 5

In some specific embodiments, the compound of the invention is selected from compounds of formula (IV):

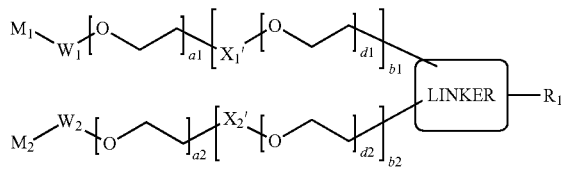

(IV)

wherein $M_1$, $M_2$, LINKER and $R_1$ are as described previously,
a1, a2, d1 and d2 are integers independently selected from integers ranging from 2 to 10, preferably from 2 to 5,
b1 and b2 are independently selected from 0 and 1,
$X'_1$ and $X'_2$ are independently selected from X' as described above in formula (II), namely from the group consisting of —NH—C(O)—(CH$_2$)$_e$— and —O—C(O)—(CH$_2$)$_e$—, wherein e is an integer from 1 to 4, and
$W_1$ and $W_2$ are independently selected from W as described above in formula (II), namely from —NH—(CH$_2$)$_f$, —O—(CH$_2$)$_f$— and —S—(CH$_2$)$_f$—, wherein f is an integer from 1 to 5.

As previously described, in such an embodiment, LINKER is a trifunctional linker which may be selected from compounds having a branched backbone having from 1 to 20 carbon atoms and at least three functional groups selected from —NH—, S, —C(=O)—, —O—, —NH—C(=O)—, —C(=O)—NH—, —O—C(=O)—, —C(=O)—O—, —NH—(C=NH)—NH—, —NH—(C=O)—NH— and —(C=O)—O—(C=O)—.

For example, LINKER may be selected from the group consisting of amino acid residues such as arginine, lysine, aspartate, glutamate, glutamine, asparagine, serine and threonine, as well as peptides having from 2 to 10 amino acid residues, preferably from 2 to 5 amino acid residues.

In some embodiments, the present invention relates to a compound of formula (I) wherein $M_2$-$Q_2$ is present, $M_3$-$Q_3$ is absent and $M_2$-$Q_2$ is identical to $M_1$-$Q_1$ In a more specific embodiment, the present invention relates to a compound of formula (IV) wherein:
a1=a2 and preferably ranging from 2 to 5,
d1=d2 and preferably ranging from 2 to 5,
b1=b2,
$M_1$ and $M_2$ are identical and preferably selected from mannosyl and dimmanosyl,
W1 and W2 are identical and preferably are —O—CH$_2$—CH$_2$—, and $X_1'$ and $X_2'$ are identical and preferably are —NH—C(O)—(CH$_2$)—.

In some other specific embodiments, the compound of the invention is selected from compounds of formula (V):

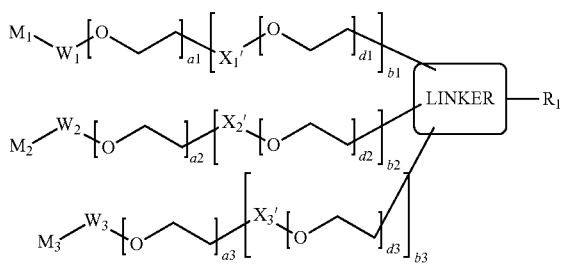

(V)

wherein $M_1$, $M_2$, LINKER and $R_1$ are as described previously, a1, a2, a3, d1, d2 and d3 are integers independently selected from integers ranging from 2 to 10, preferably from 2 to 5, b1, b2 and b3 are independently selected from 0 and 1, $X'_1$, $X'_2$ and $X'_3$ are independently selected from X' as described above in formula (II), namely from the group consisting of —NH—C(O)—(CH$_2$)$_e$— and —O—C(O)—(CH$_2$)$_e$—, wherein e is an integer from 1 to 4, and $W_1$, $W_2$ and $W_3$ are independently selected from W as described above in formula (II), namely from —NH—(CH$_2$)$_f$—O—(CH$_2$)$_f$— and —S—(CH$_2$)$_f$—, wherein f is an integer from 1 to 5.

As previously described, in such an embodiment, LINKER is a tetrafunctional linker which may be selected from compounds having a branched backbone having from 1 to 20 carbon atoms and at least four functional groups selected from —NH—, —S—, —C(=O)—, —O—, —NH—C(=O)—, —C(=O)—NH—, —O—C(=O)—, —C(=O)—O—, —NH—, —(C=NH)—NH—, —NH—(C=O)—NH— and —(C=O)—O—(C=O)—.

For example, LINKER may be selected from peptides having from 2 to 10 amino acids, preferably from 2 to 5 amino acid residues. For example, LINKER may be selected from dipeptide radicals comprising amino acids selecting from lysine, arginine, aspartate, glutamate, glutamine, asparagine, serine and threonine. LINKER may be also selected from tromethamine, glycerol, and pentaerythritol radicals and derivatives thereof.

Preferably, LINKER is a radical of formula (VI):

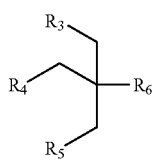

(VI)

wherein:

$R_6$ is —NHC(O)— or —OC(O)—, preferably —NH(C=O)—, and $R_3$, $R_4$ and $R_5$ are independently selected from —NHC(=O)—(CH$_2$)$_n$O— and —OC(=O)—(CH$_2$)$_n$O—, n being an integer from 1 to 10, preferably —NH—C(=O)—(CH$_2$)$_2$O—.

In some embodiments, the present invention relates to a compound of formula (I) wherein $M_2$-$Q_2$ and $M_3$-$Q_3$ are present and identical to $M_1$-$Q_1$. In a more specific embodiment, the present invention relates to a compound of formula (V) wherein:

a1=a2=a3 and preferably ranging from 2 to 5, d1=d2=d3 and preferably ranging from 2 to 5, b1=b2=b3, $M_1$, $M_2$ and $M_3$ are identical and preferably selected from mannosyl and dimannosyl, $W_1$, $W_2$ and $W_3$ are identical and preferably are —O—CH$_2$—CH$_2$—, and $X'_1$, $X'_2$ and $X'_3$ are identical and preferably are —NH—C(O)—(CH$_2$)—.

In some further specific embodiments, the compound of the invention is selected from compounds of formula (Va):

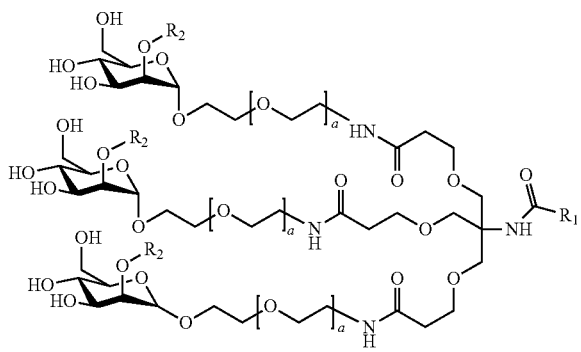

(Va)

wherein:

$R_2$ is H or α-mannosyl residue, preferably connected through (1->2) linkage, $R_1$ is as fully defined hereabove, and a is an integer from 2 to 10, preferably from 2 to 5.

In a particular embodiment, the invention relates to one or several following compounds:

a compound of formula (IIIa), wherein $R_2$ is H, $R_1$ is —(CH$_2$)$_{16}$CH$_3$, a is 3 and b is 4;

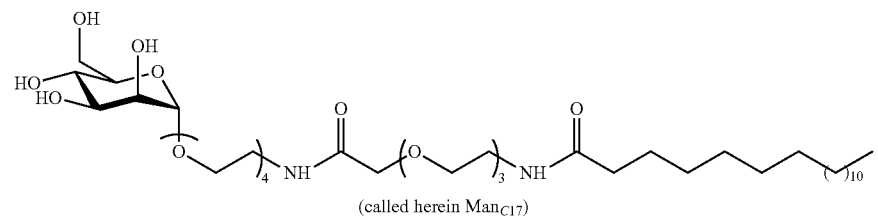

(called herein Man$_{C17}$)

a compound of formula (IIIa), wherein $R_2$ is H, $R_1$ is —$(CH_2)_{23}CH_3$, a is 3 and b is 4;
(called herein $ManC_{24}$)

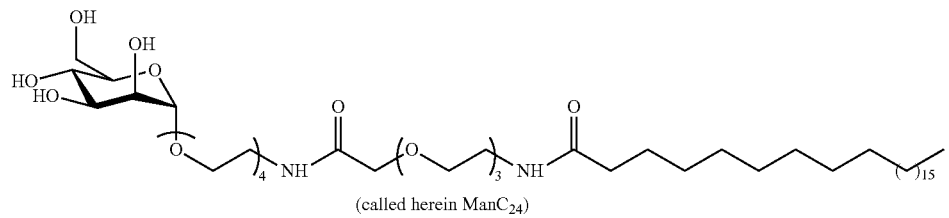

(called herein $ManC_{24}$)

a compound of formula (IIIa), wherein $R_1$ is —$(CH_2)_8$—C≡C—C≡C—$(CH_2)_{11}$—$CH_3$, $R_2$ is H, a is 3, and b is 4;

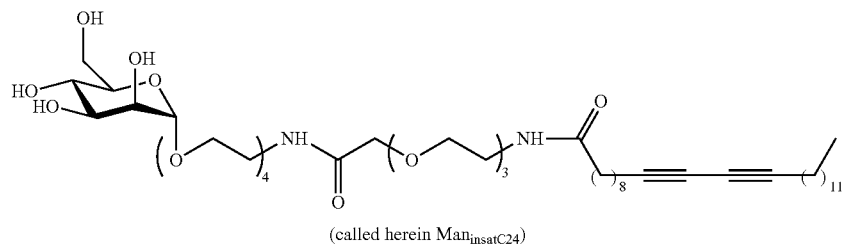

(called herein $Man_{insatC24}$)

a compound of formula (Va), wherein, $R_1$ is —$(CH_2)_{23}CH_3$, $R_2$ is H, and a is 3;

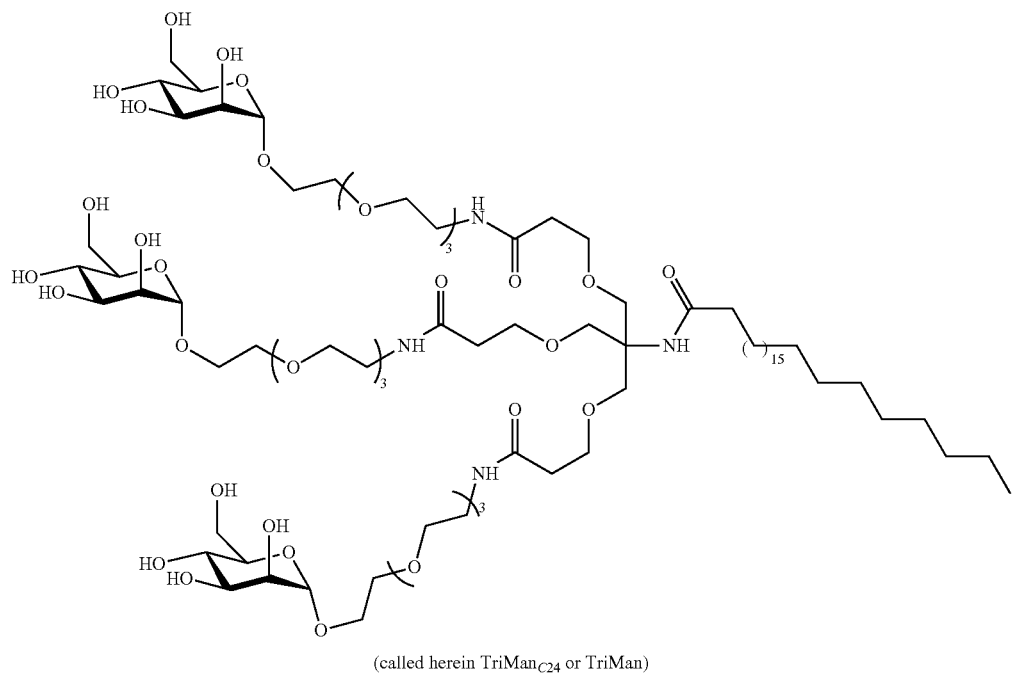

(called herein $TriMan_{C24}$ or TriMan)

a compound of formula (Va), wherein, $R_1$ is —$(CH_2)_{23}CH_3$, $R_2$ is α-mannosyl, and a is 3;

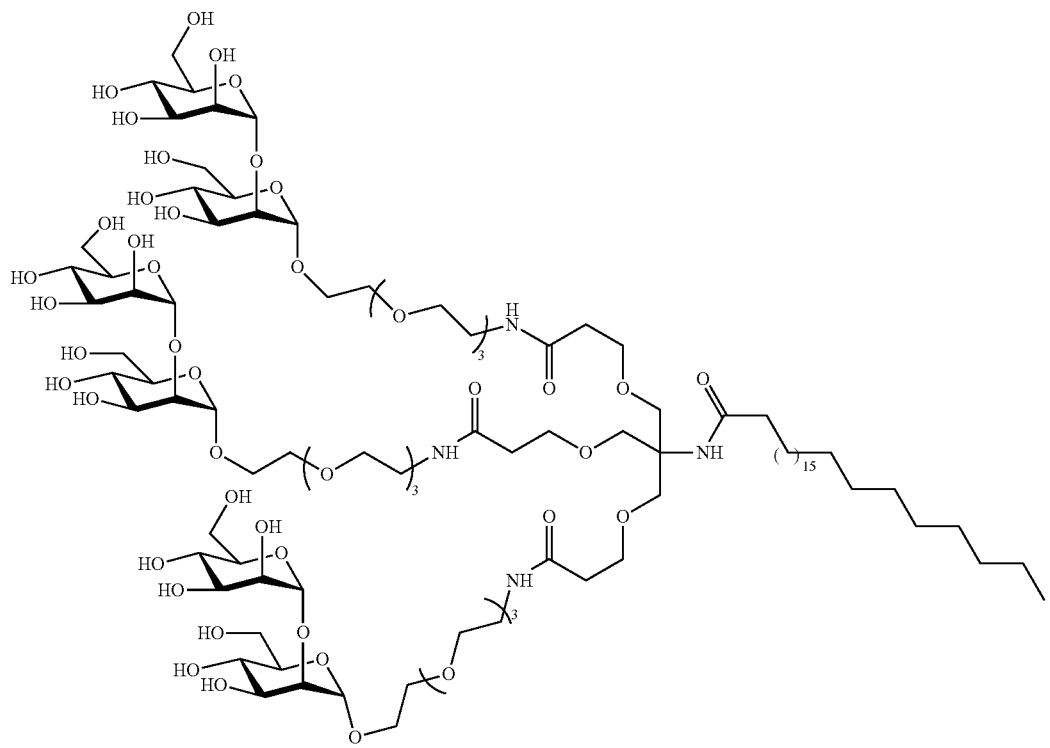
(called herein DiTriMan$_{C24}$ or DiTriMan)
a compound of formula (Va), wherein, $R_1$ is —$(CH_2)_8$—C≡C—C≡C—$(CH_2)_{11}$—$CH_3$, $R_2$ is H, and a is 3;
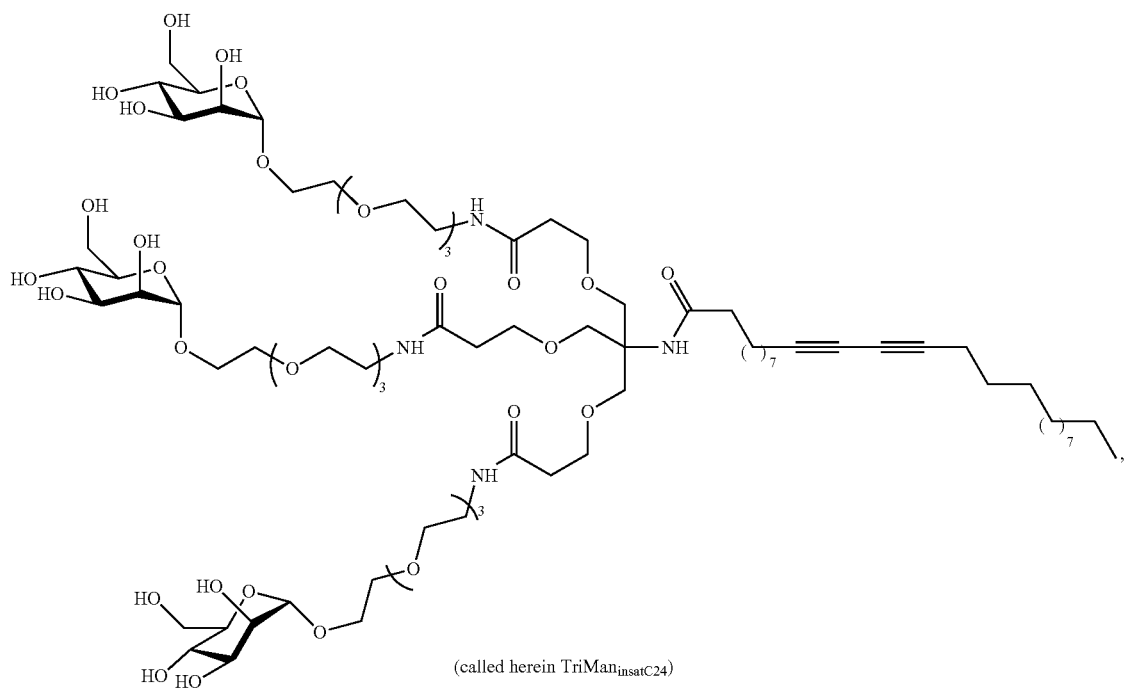
(called herein TriMan$_{insatC24}$)

and compound of formula (Va), wherein, $R_1$ is —$CH_2)_8$—C≡C—C≡C—$(CH_2)_{11}$—$CH_3$, $R_2$ is α-mannosyl and a is 3.

a compound of formula (Va), wherein, $R_1$ is —$(CH_2)_{23}CH_3$, $R_2$ is α-mannosyl, and a is 3 (called herein DiTriMan$_{C24}$);

a compound of formula (Va), wherein, $R_1$ is —$(CH_2)_8$—C≡C—C≡C—$(CH_2)_{11}$—$CH_3$, $R_2$ is H, and a is 3; (called herein TriMan$_{insatC24}$); and

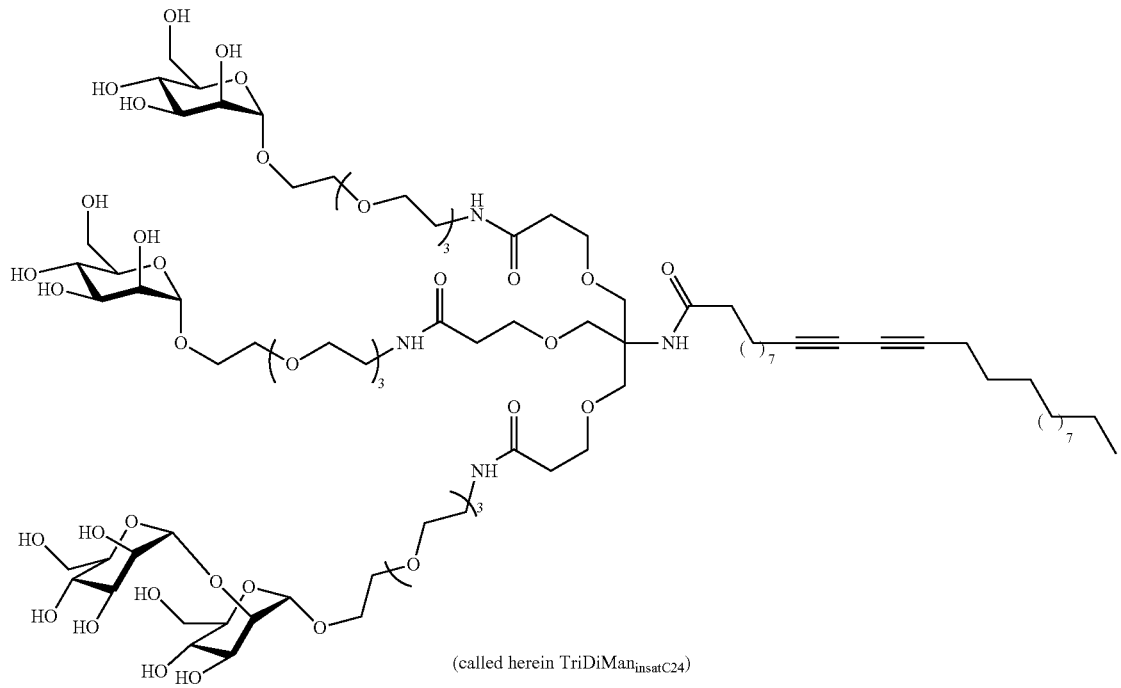

(called herein TriDiMan$_{insatC24}$)

II. Therapeutic Uses of the Compounds and Pharmaceutical Compositions Thereof The present invention also relates to a compound of any one of formulae (I), (III), (IIIa), (IV), (V) or (Va) or any particular compound disclosed herein for use as a drug, in particular for use in the treatment or the prevention of an infectious disease.

The present invention also relates to the use of a compound of the invention for the manufacture of a medicament, more specifically, to be used for the treatment and the prevention of an infectious disease.

A further object of the present invention is a method for treating a patient comprising administering an effective amount of a compound as defined in the present specification to the said patient. More precisely, the present invention relates to a method for treating or preventing an infectious disease in a patient comprising administering a therapeutically effective amount of a compound as defined herein to said patient.

In a very specific embodiment, said compound is selected from the group consisting of:

a compound of formula (IIIa), wherein $R_2$ is H, $R_1$ is —$(CH_2)_{16}CH_3$, a is 3 and b is 4 (called herein Man$_{C17}$);

a compound of formula (IIIa), wherein $R_2$ is H, $R_1$ is —$(CH_2)_{23}CH_3$, a is 3 and b is 4 (called herein Man$_{C24}$);

a compound of formula (IIIa), wherein $R_1$ is —$(CH_2)_8$C≡C—C≡C—$(CH_2)_{11}$—$CH_3$, $R_2$ is H, a is 3, and b is 4 (called herein Man$_{insatC24}$);

a compound of formula (Va), wherein $R_1$ is —$(CH_2)_{23}CH_3$, $R_2$ is H, and a is 3 (called herein TriMan$_{C24}$);

a compound of formula (Va), wherein, $R_1$ is —$(CH_2)_8$—C≡C—C≡C—$(CH_2)_{11}$—$CH_3$, $R_2$ is α-mannosyl and a is 3 (called herein TriDiMan$_{insatC24}$).

"An infectious disease" encompasses any disease or any disorder caused by a pathogen in a subject. A pathogen includes bacteria, viruses, fungi and parasites. An infectious disease includes, without being limited to, bacterial diseases and viral diseases.

As used herein, by "a therapeutically effective amount" is meant an amount of the compound of the invention which prevents, removes, or slows down the infectious disease or reduces or delays one or several symptoms or disorders caused by or associated with said infectious disease in mammals, including humans. The effective amount, and more generally the dosage regimen, of the compound of the invention and pharmaceutical compositions thereof may be easily determined and adapted by one skilled in the art.

An effective dose can be determined by the use of conventional techniques and by observing results obtained under analogous circumstances. The therapeutically effective dose of the compound of the invention will vary depending on such factors as the pathological condition to be treated (including prevention), the method of administration, any co-therapy involved, the patient's age, weight, general medical condition, medical history, etc. Typically, the amount of the compound to be administrated to a patient may range from about 0.01 mg/day/kg to 50 mg/day/kg of body weight, preferably from 0.1 mg/day/kg to 25 mg/day/kg of body weight.

For example, for a patient having a body weight of 60 kg, the daily dosage for the compound of the invention ranges from 0.6 mg to 3 g, preferably from 6 mg to 1.5 g.

In particular, the compound of the invention may be used for treating or preventing an infectious disease caused by a pathogen wherein the in vivo dissemination and/or cell transmission of the pathogen involves interaction with DC-SIGN. The pathogen may be a bacterium, a virus, a fungus or a parasite.

Such an infectious disease encompasses, without being limited to, infectious diseases caused by a pathogen selected from the group consisting of *Tuberculosis mycobacterium, Helicobacter pylori, Candida albicans, Leishmania species,* hepatitis C virus (HCV), Ebola virus, human immunodeficiency virus (HIV) including HIV-1, Dengue virus, Marburg virus, West Nile virus, Aura virus, Herpes simplex virus, severe acute respiratory syndrome (SARS) virus, measles, avian H5N1 Influenza and cytomegalovirus.

In some embodiments, the pathogen is selected from the group consisting of hepatitis C virus (HCV), Ebola virus, human immunodeficiency virus (HIV) including HIV-1, Dengue virus, Marburg virus, West Nile virus, Aura virus, Herpes simplex virus, severe acute respiratory syndrome (SARS) virus, measles, avian H5N1 Influenza and cytomegalovirus.

More specifically, the compound of the invention may be used for inhibiting and/or reducing cis-infection or trans-infection in the treatment or the prevention of a viral disease, including a disease caused by hepatitis C virus (HCV), Ebola virus, human immunodeficiency virus (HIV) including HIV-1, Dengue virus, Marburg virus, West Nile virus, Aura virus, Herpes simplex virus, severe acute respiratory syndrome (SARS) virus, measles, avian H5N1 Influenza and cytomegalovirus.

By "trans-infection" is intended the infection of a target cell mediated by transmission from cells (mainly dendritic cells) that have captured the pathogen, By "cis-transfection" is intended the direct infection of a cell by a pathogen The assessment of the inhibition of cis-infection and trans-infection may be performed by routine experiments well-known by one skilled in the art. The method to be used depends on the virus to be tested.

For example, in the case of HIV-1, the inhibition of trans-infection may be assessed as described herein in the Examples, briefly, by:
incubating human dendritic cells (DCs) with the compound to be tested and then infecting said dendritic cells with HIV-1 virions,
after extensive washing, co-culturing DCs with MAGI-CCR5 cells (or T lymphocytes), and
quantifying viral trans-infection of MAGI-CCR5 cells (or T lymphocytes).

In this respect, one may cite two studies that have described protocols for measuring HIV-1 trans-infection from a DC-SIGN-expressing cell line to T lymphocytes: Martinez-Avila et al., 2009, and Sattin et al., 2010.

In a particular embodiment, the compound according to the invention may be used as a drug for inhibiting HIV trans-infection of CD4+lymphocytes mediated by DCs.

In another embodiment, the compound according to the invention may be used as a drug for inhibiting cis-infection of DCs by Dengue virus.

A further object of the invention is a pharmaceutical composition comprising (i) a compound of the invention as an active principle and (ii) at least one pharmaceutically acceptable excipient.

The pharmaceutical composition of the invention may be formulated according to standard methods such as those described in Remington: *The Science and Practice of Pharmacy* (Lippincott Williams & Wilkins; Twenty first Edition, 2005). Pharmaceutically acceptable excipients that may be used, depending on the desired galenic form and the route of administration, are described, for example, in the *Handbook of Pharmaceuticals Excipients, American Pharmaceutical Association* (Pharmaceutical Press; 6th revised edition, 2009).

The pharmaceutical composition of the invention may be obtained by admixing a compound of the invention with an appropriate degree of purity with at least one customary excipient (or carrier) such as (a) fillers such as starch, lactose, sucrose, glucose, mannitol, and silicic acid; (b) binders such as carboxymethylcellulose, gelatin, polyvinylpyrrolidone, and sucrose; (c) humectants such as glycerol; (d) disintegrating agents such as agar-agar, calcium carbonate, potato or tapioca starch, alginic acid, certain complex silicates, and sodium carbonate; (e) solution retarders such as paraffin; (f) absorption accelerators such as quaternary ammonium compounds; (g) wetting agents such as glycerol monostearate; (h) adsorbents such as kaolin and bentonite; (i) lubricants such as talc, calcium stearate, magnesium stearate, solid polyethylene glycols, and sodium lauryl sulfate; (j) antioxidant agents; (k) buffering agents such as sodium citrate or sodium phosphate; (l) preservatives; and (m) flavours and perfumes, etc.

It goes without saying that (i) the excipient(s) to be combined with (ii) the active ingredient may vary upon (i) the physico-chemical properties including the stability of the said active ingredient, (ii) the pharmacokinetic profile desired for said active ingredient, (iii) the galenic form and (iv) the route of administration.

Solid dosage forms such as tablets, capsules, pills, and granules can be prepared with coatings and shells, such as enteric coatings or other suitable coatings or shells. Several such coatings and/or shells are well-known in the art, and can contain opacifying agents, and can also be of such composition that they release the active compound or compounds in a certain part of the intestinal tract and/or in a delayed manner. Examples of embedding compositions which can be used are polymeric substances and waxes. The active compounds can also be used in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propyleneglycol, 1,3-butyleneglycol, dimethylformamide, oils, polyethyleneglycol and fatty acid esters of sorbitan and the like or mixtures of these substances. If desired, the composition can also include adjuvants, such as wetting agents, emulsifying and suspending agents, and sweetening, flavoring and/or perfuming agents.

Suspensions, in addition to the compound of the invention, can contain suspending agents, such as ethoxylated isostearyl alcohols, polyoxyethylene sorbitol and sorbitan esters, microcrystalline cellulose, aluminum metahydroxide, bentonite, agar-agar, and the like.

Vaginal or rectal suppositories may be prepared by mixing the compounds of the present invention with suitable non-irritating excipients or carriers such as cocoa butter, polyethyleneglycol, or a suppository wax which is solid at ordinary temperatures but liquid at body temperature and therefore melts in the rectum or vaginal cavity and release the active component.

For example, a vaginal gel composition may be prepared by mixing in purified water a compound of the invention together with edetate sodium, citric acid, glycerin, methylparaben, propylparaben, and hydroxycellulose.

The ointments, pastes, creams and gels may contain, in addition to an active compound of this invention, excipients such as animal and vegetable fats, oils, waxes, paraffins, starch, tragacanth, cellulose derivatives, polyethyleneglycols, silicones, bentonites, silicic acid, talc and zinc oxide, or mixtures thereof.

The pharmaceutical composition may comprise:
from 0.01% to 50% by weight of a compound of the invention, and
from 50% to 99.99% by weight of excipients,
the percentage being expressed as compared to the total weight of the composition.

Preferably, the pharmaceutical composition may comprise:
from 0.1% to 25% by weight of a compound of the invention, and
from 75% to 99.9% by weight of excipients.

The amount of the compound of the invention in the pharmaceutical composition may depend on the galenic form of the said composition.

For example, in the case of an oral tablet, the compound of the invention may account for 5% to 25% by weight of the total weight of said oral tablet.

In the case of a gel, the compound of the invention may account for 1% to 20% of the total weight of the gel.

The compounds and the pharmaceutical compositions of the invention may be administered by any conventional route, including by enteral route (i.e., oral), e.g., in the form of tablets, capsules, by parenteral route, e.g., in the form of injectable solutions or suspensions and by topical route, e.g., in the form of gels, ointments, lotions, patches, suppositories and the like.

As used herein, "topical route" encompasses, without being limited to, dermal routes and mucosal routes, e.g., vaginal, rectal, sublingual and ocular routes.

In some specific embodiments, the compound and the composition of the invention are administrated by mucosal route, and in particular by vaginal or rectal route. In such an embodiment, the pharmaceutical composition may be formulated as a gel, a vaginal tablet, a vaginal capsule, a cream, an ointment, a suppository or a mucoadhesive patch or be incorporated in a delivery system such as a vaginal ring, a pessary or in a condom (e.g., female or male condom).

For example, the composition of the invention may be a lubricant gel for condoms. Another object of the invention is a condom coated with the compound or the composition according to the invention. In some embodiment, the condom is lubricated with a composition according to the invention.

The pharmaceutical composition of the invention may comprise an additional active ingredient (i.e., an additional therapeutic agent). As used herein, a "therapeutic agent" or "an active ingredient" refers to any class of therapeutic molecules and thus encompasses, without being limited to, vitamins, anti-infectious agents, anti-tumoral agents, analgesic agents, anti-inflammatory agents, anti-diabetic agents and the like.

In other words, the invention relates to a pharmaceutical composition comprising (i) a compound of the invention as active ingredient, (ii) at least one pharmaceutically acceptable excipient and optionally (iii) an additional therapeutic agent.

Such a pharmaceutical composition may comprise:
from 0.01% to 50% by weight of a compound of the invention,
from 0% to 50% by weight of the additional therapeutic ingredient, and
from 50% to 99.99% by weight of excipients,
the percentage being expressed as compared to the total weight of the pharmaceutical composition.

In a preferred embodiment, said additional therapeutic agent is selected from anti-infectious agents, e.g., anti-viral agents and antibiotic agents.

When the composition is intended for the treatment or the prevention of disease caused by a bacterium such as *Mycobacterium tuberculosis* or *Helicobacter pylori*, the additional active ingredient may be selected from antibiotics, preferably from antibiotics such as isoniazide, metronidazole, clarithromycin, fluoroquinolones including ciprofloxacin, rifampicin, β-lactam antibiotics such as amoxicillin, and carbapenems including imipenem.

When the composition is intended for the treatment or the prevention of hepatitis C, said additional active ingredient may be selected from anti-hepatitis C virus (anti-HCV) agents. Anti-HCV agents include, without being limited to, pegylated interferon-alpha, ribavirin and boceprevir.

When the composition is intended for the treatment or the prevention of HIV infection and related diseases, said additional active ingredient may be selected from anti-HIV agents, preferably from anti-HIV agents able to inhibit cis-infection.

In some specific embodiments, when the composition is intended for the treatment or the prevention of HIV infection and related diseases, said additional active therapeutic agent may be selected from the group consisting of (i) anti-HIV agents able to prevent cell infection (i.e., the entry of virions into cells) and (ii) anti-viral agents able to inhibit viral replication.

Anti-viral agents able to prevent cell infection (i.e., the entry of virions into cells) include, without being limited to, CCR5 antagonists such as maraviroc, vicriviroc, aplaviroc and fusion inhibitors such as enfuvirtide.

Anti-viral agents able to inhibit viral replication include, without being limited to,
(i) reverse transcriptase inhibitors such as tenofovir, zidovudine, didanosine, zalcitabine, stavudine, lamivudine, abacavir, amtricitabine, nevirapine, efavirenz, and delavirdine,
(ii) protease inhibitors such as saquinavir, indinavir, ritonavir, nelfinavir, amprenavir, lopinavir, atazanavir, fosamprenavir, darunavir and brecanavir,
(iii) maturation inhibitors such as bevirimat and
(iv) integrase inhibitors such as raltegravir and elvitegravir.

For reviews concerning anti-HIV drugs see for example Flexner, *Nat. Rev. Drug Discov.* 2007, 6, 959-966, Oversteegen et al., *Nat. Rev. Drug Discov.* 2007, 951-952 and Tilton and Doms, *Antiviral Res.* 2010, 85, 91-100.

In a more general aspect, the additional therapeutic agent may be an anti-viral agent able to inhibit HIV cis-transfection.

A further object of the invention is a therapeutic combination for preventing or treating an infectious disease comprising (i) a compound of the invention and (ii) a therapeutic agent for simultaneous, separate or successive administration to a patient in need thereof.

The therapeutic combination and the compound of the invention may be administered to the patient by the same route or by distinct routes. For example, the compound of the invention may be administered to the patient by mucosal route whereas the therapeutic agent may be administered orally.

Said therapeutic agent may be of any kind and preferably selected from the group consisting of anti-viral agents, antibiotics and anti-inflammatory agents.

In a specific embodiments, the therapeutic combination is intended to prevent or treat an infectious disease, preferably caused by a pathogen selected from the group consisting of *Tuberculosis mycobacterium, Helicobacter pylori, Candida albicans, Leishmania* species, Ebola virus, Marburg virus, human immunodeficiency virus, hepatitis C virus, Dengue virus, West Nile virus, Aura virus, Herpes simplex virus, severe acute respiratory syndrome (SARS) virus, measles, avian H5N1 Influenza, and cytomegalovirus.

When the combination is intended for the treatment or the prevention of hepatitis C, said therapeutic agent may be selected from anti-hepatitis C virus (anti-HCV) agents. Anti-HCV agents include, without being limited to, pegylated interferon-alpha, ribavirin and boceprevir.

When the combination is intended for the treatment or the prevention of HIV infection and related diseases, the therapeutic agent may be selected from anti-HIV agents, preferably from anti-HIV agents able to inhibit cis-infection.

In some specific embodiments, when the composition is intended for the treatment or the prevention of HIV infection and related diseases, said therapeutic agent may be selected from the group consisting of (i) anti-HIV agents able to prevent cell infection (i.e., the entry of virions into cells) and (ii) anti-viral agents able to inhibit viral replication.

Examples of anti-HIV agents able to prevent cell infection and examples of anti-HIV agents able to inhibit viral replication are provided hereabove.

III. Methods for Preparing the Compounds of the Invention

A further object of the invention is a method for preparing a compound of formula (I).

In a specific embodiment, the present invention relates to a method for preparing a compound of formula (IIIa):

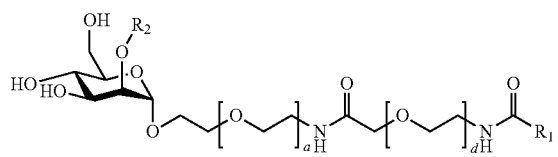

(IIIa)

wherein:
$R_2$ is H or alpha-mannosyl,
a is an integer from 2 to 10, preferably from 2 to 5,
d is an integer from 2 to 10, preferably from 2 to 5, and
$R_1$ is an unsaturated or saturated $C_{17}$-$C_{30}$ alkyl as fully described hereabove,
or a pharmaceutically acceptable salt, ester or solvate thereof, comprising:
(i) reacting a compound of formula (VII) : H—(O—CH$_2$—CH$_2$)$_{(a+1)}$N$_3$ with a compound of formula (VIa) or a compound of formula (VIb):

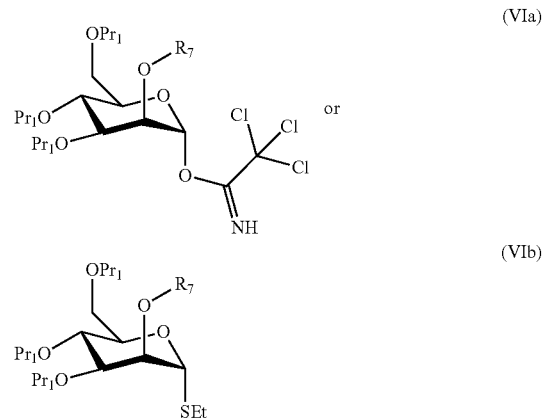

wherein $R_7$ is $Pr_1$ or protected alpha-mannosyl and each $Pr_1$ is independently selected from protective groups for hydroxyl,
so as to form a compound of formula (VIII):

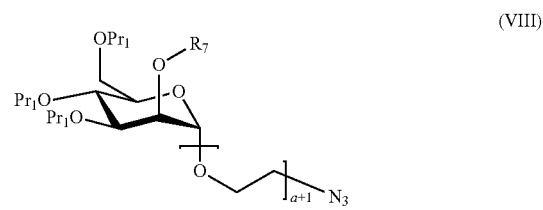

(ii) reducing the azido group of a compound of formula (VIII) into the NH$_2$ group;
(iii) reacting the compound obtained at step (ii) with the compound of formula (IX):

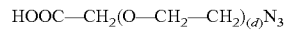

HOOC—CH$_2$(O—CH$_2$—CH$_2$)$_{(d)}$N$_3$ so as to form the compound of formula (X):

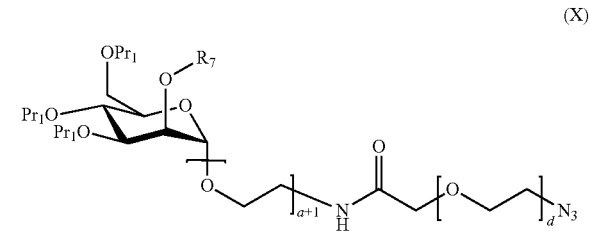

(iv) reducing the azido group of a compound of formula (X) into NH$_2$;
(v) reacting the compound obtained at step (iv) with $R_1$COOH; and
(vi) deprotecting the mannosyl hydroxyl groups of the compound obtained in step (v) so as to obtain the compound of formula (IIIa).

As used herein, "a protected alpha-mannosyl" means an alpha mannosyl radical wherein the hydroxyl groups are protected by any appropriate protective group such as benzyl (Bn) or acetate (Ac). Similarly, each Pr1 is independently selected from protective groups for hydroxyl, in particular benzyl and acetyl.

The compound (VIa) may be obtained as described in Su, 2010 from mannose by protecting hydroxyl groups, reacting mannose with Ac$_2$O in the presence of Et$_3$N and DMAP and then replacing the acetyl group introduced on anomeric position by a trichloroacetimidate moiety.

For example, the compound (VIb) may be obtained according to the procedure described in Duffels, 2000. Briefly, the corresponding fully acetylated glycosyl bromide (see Banoub, 1986) Is reacted with 2,6-lutidine in dichloromethane/methanol so as to stereoselectively obtain peracytylated 1,2-exo-orthoacetate. The resulting compound is then treated with ethanethiol in the presence of HgBr$_2$ and a molecular sieve.

The compound of formula (VII) may be obtained as described in Khiar, 2009 by reacting an appropriate oligoethylene glycol with NaN$_3$ after activation of the hydroxyl group with methanesulfonyl chloride.

In the case of reaction of compound (Via) with compound (VII), step (i) is typically performed in the presence of a Lewis acid such as trimethylsilyl trifluoromethanesulfonate (TMSOTf) as described in Su, 2010.

hydrogenation catalyzed by palladium on carbon (Pd/C) whereas acetyl may be removed by reaction with MeONa in methanol.

Concerning standard procedures relative to protecting groups in organic chemistry, one may refer to Greene, "Greene's Protective Groups in Organic Synthesis", 2006, John Wiley & Sons Inc; 4th revised edition.

Said method for preparing a compound of formula (IIIa) may comprise one or more additional steps, for example steps enabling the removal and/or the introduction of appropriate protecting groups.

For example, if R$_1$ contains an insaturation such as a double bond and/or a triple bond, it goes without saying that step (vi) does not comprise a reaction such as hydrogenation which may reduce the insaturation(s) of R$_1$. Accordingly, if the compound of formula (VIa) or (VIb) contains a hydroxyl group protected by benzyl, said benzyl may be removed and eventually replaced by another protecting group before step (v).

In another embodiment, the present invention relates to a method for preparing a compound of formula (Va):

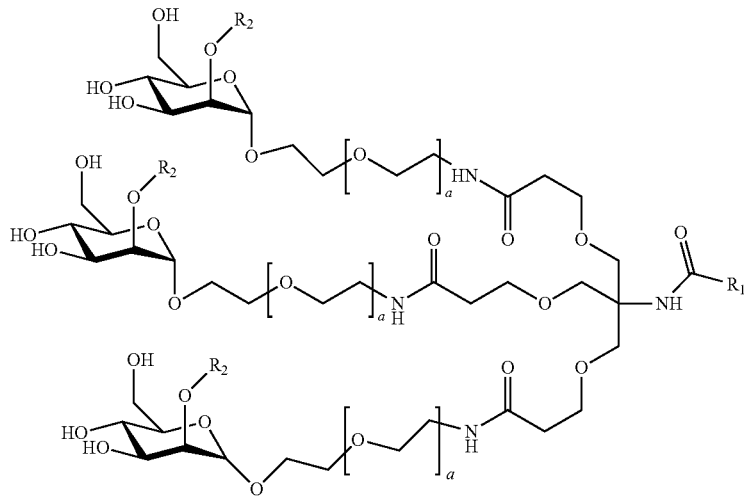

The reduction of azido group is generally performed using classical Staudinger's condition, i.e., by reacting the compound comprising azido group with triphenylphosphine at room temperature and overnight.

The compound (IX) may be obtained from compound (VII) by oxidation reaction, for example using Jones reagent (which is a mixture of chromic trioxide or sodium dichromate in diluted sulfuric acid, which forms chromic acid in situ).

The formation of the amide bond (peptide bond) in steps (iii) and (v) may be performed by any conventional procedure described in the prior art, for example by activating the carboxylic acid function:
by reaction with a carbodiimide and optionally with 2-hydroxy-benzotriazole (HOBt) or 1-hydroxy-7-aza-benzotriazol (HOAt), or
by reaction with a phosphonium or uranium salt such as (benzotriazol-1-yloxy)tris(dimethylamino)phosphonium hexafluorophosphate (BOP) or O—(7-azabenzotriazol-1-yl)-N,N,N',N'-tetramethyluronium hexafluorophosphate (HATU).

The deprotection of hydroxyl groups may be performed by routine procedures. Benzyl groups may be removed by wherein:

R$_2$ is H or alpha-mannosyl, a is an integer from 2 to 10, preferably from 2 to 5, and R$_1$ is an unsaturated or saturated C$_{17}$-C$_{30}$ alkyl, or a pharmaceutically acceptable salt, ester or solvate thereof, comprising:

(i) Reacting R$_f$COOH with a compound of formula (XI):

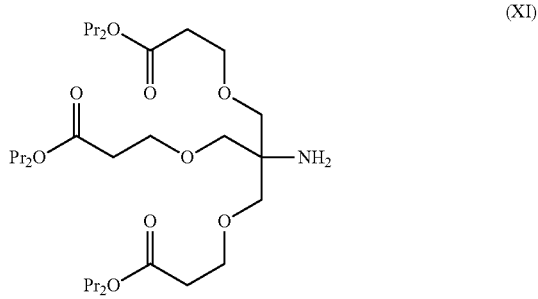

(XI)

wherein Pr$_2$ is a protective group for a carboxyl group, preferably an ethyl group, so as to provide the compound of formula (XII):

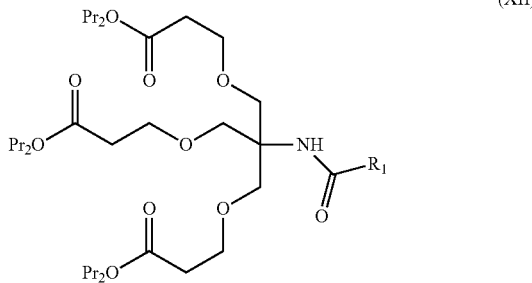

(ii) Deprotecting the carboxylic groups by saponification of ester groups,
(iii) Reacting the compound obtained in step (ii) with the compound of formula (XIII):

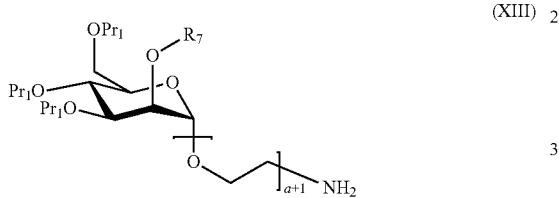

wherein each Pr$_1$ is a protective group for hydroxyl, preferably acetyl, so as to form a compound of formula (XIV):

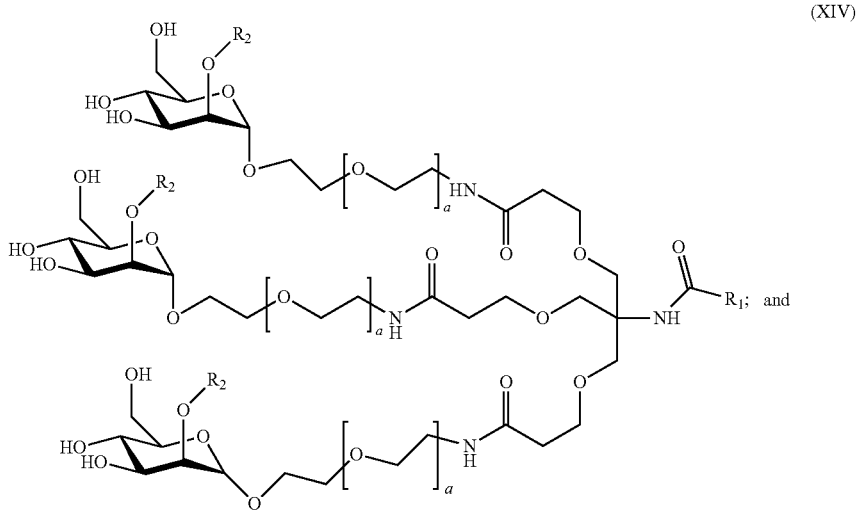

and
(iv) Deprotecting the mannosyl hydroxyl groups so as to obtain the compound of formula (Va).

The compound of formula (XII) may be obtained according to Kikkeri, 2009. Briefly, Tris(hydroxymethyl)aminomethane is first reacted with acrylonitrile in 1,4-dioxane to afford the corresponding tricyanide by Michael addition of the hydroxyl group. Hydrolysis of the cyano groups in HCl (37%) followed by esterification so as to provide the desired triester. Amide bond formation was then achieved by coupling the amine with the desired carboxylic acid under HOBt/DCC conditions in THF to give compound (XII).

The remarks provided previously for the synthesis of the compound of formula (IIIa) concerning protective groups and the formation of amide bonds are also relevant for the synthesis of the compound of formula (Va).

Noticeably, compound (XIII) may be obtained by reduction of the compound of formula (VIII) described hereabove.

The present invention is further illustrated by, without being limited to, the above examples.

IV. Examples
a. Material and Methods

Chemical synthesis: General Experimental Conditions for the Synthesis of the Compounds Described in the Present Specification All chemicals and solvents were of reagent grade and were used without further purification. Unless indicated, reactions were carried out under an atmosphere of argon in flame-dried glassware with magnetic stirring. Molecular sieves were stored in an oven (T=130° C.) and cooled in vacuo. The acidic-ion exchange resin used was an Amberlite IR 120 (hydrogen form). NHS-Alexa 633 was provided from Invitrogen. The progress of all reactions and column chromatography was monitored by thin-layer chromatography (TLC). TLC was performed using Merck silica gel 60 F$_{254}$ precoated plates and visualized by UV absorption and/or stained with a solution of vanillin or phosphomolybdic acid. $^1$H and $^{13}$C NMR spectra were recorded on a Bruker Avance DPX 300 Spectrometer (operated at 300 and 75 MHz,respectively) or ultrashield plus 400 Spectrometer (operated at 400 and 100 MHz, respectively) or ultrashield plus 500 Spectrometer (operated at 500 and 125 MHz, respectively). The $^1$H NMR chemical shifts are reported in parts per million, using the signal for residual solvent protons (7.24 for CDCl$_3$, 3.31 for MeOD, 7.22 for C$_5$D$_5$N) as reference. The $^{13}$C NMR chemical shifts are reported in parts per million, using the signal for residual solvent protons as reference (77.23 for CDCl$_3$, 48.95 and for MeOD, 123.87 for C$_5$D$_5$N). Data were represented as follows: chemical shift, multiplicity (s=singlet, bs=broad singlet, d=doublet, dd=doublet of doublets, t=triplet, q=quadruplet and m=multiplet), integration and coupling (J in Hz). LC- MS data were obtained using an LC/MSD/SL, Agilent Technologies; ionising source is APCl/ESI, Agilent Technologies 1200 autosampler; pump, Agilent 1200 binary system; column, ThermoScientific (58282): 30×1 mm, 19 μ, hypersil gold C18, Agilent Technologies 1200 DAD detector; Agilent Technologies MS quadrupole mass spectrometer operating in APCl/ESI mode. High-resolution mass spectra (HRMS) were obtained using an Agilent Q-TOF (time of flight) 6520. Infrared spectra were obtained from solution in CHCl₃ or MeOH using a recorder on a Nicolet 380 FT-IR from Thermo Electron Corporation.

The synthesis schemes for the different compounds described herein are shown in FIG. 4. The numbering of compounds refers to the numbering used in FIGS. 4A-4F.

Preparation of Peracylated Azide (Compound 12)

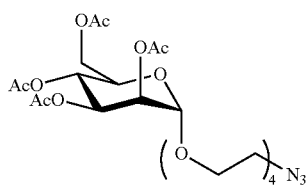

12

Compound 12 was prepared according to procedures described by Su Y. et al., (2010).

Preparation of Compound 13.

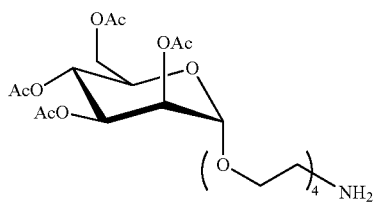

13

Peracetylated mannose azide 12 (1.71 g, 2.63 mmol, 1 equiv.) was dissolved in 15 mL of tetrahydrofuran. Triphenylphosphine (898 mg, 2.90 mmol, 1.1 equiv.) and water (85 μL, 3.88 mmol, 1.5 equiv.) were added. The reaction mixture was stirred overnight at room temperature. Solvents were removed under reduced pressure and the crude residue was directly purified by flash chromatography over a silica gel column eluted first with DCM/MeOH (9/1, v/v) to eliminate impurities and then with a mixture DCM/MeOH/NEt₃ (80/19/1, v/v/v) to afford product 13 (1.32 g, 81%) as a yellow oil. $R_f$: 0.15 (DCM/MeOH/NEt₃: 80/19/1, v/v/v). ¹H NMR δ (ppm) (CDCl₃, 300 MHz) 5.07-4.95 (m, 3H), 4.60 (s, 1H), 3.98 (dd, 1H, J=5.4 Hz, J=12.9 Hz), 3.83-3.79 (m, 2H), 3.57-3.37 (m, 12H), 3.27-3.22 (m, 2H), 2.59-2.56 (m, 2H), 2.29-2.24 (m, 2H, NH2), 1.87 (s, 3H), 1.78 (s, 3H), 1.74 (s, 3H), 1.70 (s, 3H). ¹³C NMR δ (ppm) (CDCl₃, 75 MHz) 170.6, 170.0, 169.9, 169.8, 97.7, 70.8, 70.7, 70.3, 70.1, 69.6, 69.2, 68.5, 67.4, 66.2, 62.5, 41.8, 21.0, 20.8. IR (neat film, cm⁻¹): 2872, 1742, 1669, 1437, 1368, 1218, 1133, 1081, 1043, 977, 916, 729, 600. LC-MS (ESI) m/z [M+H]⁺: 524.

Preparation of Compound Man$_{C1}$ 1 (Comparative)

The amine-based O-mannose 13 (15 mg, 0.28 mmol, 1 equiv.) was dissolved in 1 mL of anhydrous tetrahydrofuran. The reaction mixture was cooled down to 0° C. and acetyl chloride (30 μL, 0.42 mmol, 1.5 equiv.) was added dropwise.

The solution was allowed to warm at room temperature and to stir overnight. Solvent was removed under reduced pressure and the crude residue was purified by flash chromatography over a silica gel column eluted with DCM/Acetone (8/2, v/v) to afford peracetylated acetamide 14 (39 mg, 25%) as a colorless oil. $R_f$: 0.36 (DCM/Acetone: 80/20, v/v). ¹H NMR δ (ppm) (CDCl₃, 300 MHz) 5.36-5.23 (m, 3H), 4.85 (s, 1H), 4.28 (dd, 1H, J=4.8 Hz, J=13.0 Hz), 4.10-4.02 (m, 2H), 3.83-3.55 (m, 16H), 2.42 (s, 3H), 2.13 (s, 3H), 2.08 (s, 3H), 2.02 (s, 3H), 1.97 (s, 3H). ¹³C NMR δ (ppm) (CDCl₃, 75 MHz) 170.4, 170.1, 98.0, 71.1, 71.0, 70.9, 70.8, 70.4, 69.4, 68.8, 67.7, 66.5, 62.8, 45.5, 26.9, 21.1. IR (neat film, cm⁻¹): 2922, 1744, 1694, 1428, 1368, 1213, 1133, 1082, 1043, 1012, 978, 800. LC-MS (ESI) m/z [M+H]⁺: 566.

The intermediate 14 (38 mg, 67 μmol, 1 equiv.) was dissolved in 0.5 mL of anhydrous methanol. Sodium methoxide (3 mg, 50 μmol, 0.75 equiv.) was added and the reaction mixture was stirred at room temperature until all the reactant was hydrolyzed as monitored by TLC analysis (DCM/MeOH, 80/20, v/v). The solution was then quenched with a resin Amberlite IR 120 hydrogen form (H⁺) until an acidic pH (about ≃4-5) was reached. The resin was filtered with methanol and the filtrate was concentrated under reduced pressure. The residue was purified over a Sephadex G25 column eluted with methanol to afford the compound Man$_{C1}$ 1 (26 mg, 97%) as a yellow oil. ¹H NMR δ (ppm) (MeOD, 400 MHz) 4.70 (d, 1H, J=1.2 Hz), 3.74-3.71 (m, 3H), 3.63-3.44 (m, 16H), 3.29 (t, 3H, J=5.2 Hz), 1.91 (s, 3H). ¹³C NMR δ (ppm) (MeOD, 100 MHz) 174.0, 101.8, 74.7, 72.6, 72.1, 71.6, 71.4, 71.3, 70.3, 68.7, 67.8, 63.0, 40.9, 22.2. IR (neat film, cm⁻¹): 3362, 2924, 1647, 1220, 1129, 1090, 1034, 1009. LC-MS (ESI) m/z [M+H]⁺: 398.

Preparation of Compound 16.

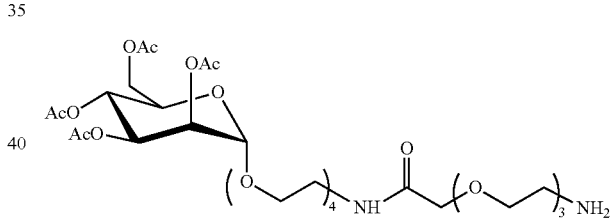

The compound 13 (613 mg, 1.07 mmol, 1.2 equiv.), carboxylic acid 9 (200 mg, 0.86 mmol, 1 equiv.) and HOBt (164 mg, 1.21 mmol, 1.5 equiv.) were dissolved in a mixture of 10 mL of anhydrous tetrahydrofuran and 10 mL of anhydrous acetonitrile. DCC (249 mg, 1.21 mmol, 1.5 equiv.) was added and the mixture was stirred at reflux overnight; TLC analysis (DCM/Acetone, 6/4, v/v) revealed complete conversion of the starting materials into one product. The precipitate was filtered off and filtrate was removed under reduced pressure. The resulting oil was diluted into 150 mL of DCM and the organic phase was washed first with a saturated aqueous solution of sodium hydrogenocarbonate and then with a saturated aqueous solution of ammonium chloride. The organic layer was dried over Na₂SO₄, filtered and evaporated under vacuum. The crude mixture was purified by flash chromatography over a silica gel column eluted first with AcOEt/Cyclohexane (8/2, v/v) to eliminate the impurities and then with DCM/Acetone (6/4, v/v) to afford azide 15 (95 mg, 14%) as a colorless oil. $R_f$: 0.67 (DCM/Acetone: 6/4, v/v). ¹H NMR δ (ppm) (CDCl₃, 300 MHz) 6.33 (s, 1H, NH), 5.33-5.24 (m, 3H), 4.84 (s, 1H), 4.26 (dd, 1H, J=5.1 Hz, J=13.6 Hz), 4.08-3.98 (m, 4H), 3.81-3.35 (m, 28H), 2.13 (s, 3H), 2.07 (s, 3H), 2.01 (s, 3H), 1.96 (s, 3H). $^{13}$C NMR δ (ppm) (CDCl$_3$, 75 MHz) 171.2, 170.7, 170.5, 170.1, 98.1, 71.3, 71.1, 71.0, 70.9, 70.6, 70.3, 69.9, 69.4, 68.8, 67.7, 66.5, 62.8, 51.0, 39.0, 21.0. IR (neat film, cm$^{-1}$): 2873, 2106, 1746, 1671, 1540, 1437, 1369, 1224, 1133, 1085, 1047, 979. LC-MS (ESI) m/z [M+H]$^+$: 739.

Azide 15 (95 mg, 0.11 mmol, 1 equiv.) was then dissolved in 1 mL of tetrahydrofuran. Triphenylphosphine (37 mg, 0.14 mmol, 1.1 equiv.) and water (4 μL, 0.17 mmol, 1.5 equiv.) were then added. The reaction mixture was stirred overnight at room temperature. Solvents were removed under reduced pressure and the crude residue was directly purified by flash chromatography over a silica gel column eluted first with DCM/MeOH (9/1, v/v) to eliminate impurities and then with a mixture of DCM/MeOH/NEt$_3$ (80/19/1, v/v/v) to afford the product 16 (45 mg, 49%) as a colorless oil. R$_f$: 0.26 (DCM/MeOH/NEt$_3$: 80/19/1, v/v). $^1$H NMR δ (ppm) (CDCl$_3$, 300 MHz) 5.30-5.22 (m, 3H), 4.84 (s, 1H), 4.25 (dd, 1H, J =4.8 Hz, J =12.0 Hz), 4.09-3.96 (m, 4H), 3.81-3.45 (m, 26H), 2.95 (t, 2H, J=4.5 Hz), 2.12 (s, 3H), 2.07 (s, 3H), 2.00 (s, 3H), 1.95 (s, 3H). $^{13}$C NMR δ (ppm) (CDCl$_3$, 75 MHz) 170.5, 170.1, 169.9, 169.8, 169.7, 97.7, 72.3, 70.9, 70.7, 70.6, 70.3, 70.1, 69.7, 69.5, 69.2, 68.5, 67.3, 66.2, 62.5, 41.4, 38.7, 20.9, 20.8. IR (neat film, cm$^{-1}$): 3368, 2873, 1742, 1661, 1540, 1440, 1369, 1225, 1085, 1045, 978. LC-MS (ESI) m/z [M+H]$^+$: 713.

Preparation of Compound 20 (Acetylated Man$_{C11}$)

Substrate 16 (15 mg, 18 μmol, 1.2 equiv.), lauric acid 17 (4 mg, 16 μmol, 1 equiv.) and HOBt (4 mg, 24 μmol, 1.5 equiv.) were dissolved in 0.5 mL of anhydrous tetrahydrofuran. DCC (5 mg, 24 μmol, 1.5 equiv.) was added and the mixture was stirred overnight at reflux. After completion of the reaction, the solvent was removed under reduced pressure and the crude residue was purified by flash chromatography over a silica gel column eluted first with AcOEt/Cyclohexane (8/2, v/v) to eliminate the impurities and then with DCM/MeOH (9/1, v/v) to afford the compound 20 (16 mg, 98%) as a colorless oil. R$_f$: 0.37 (DCM/MeOH: 90/10, v/v).$^1$H NMR δ (ppm) (CDCl$_3$, 400 MHz) 6.39 (s, 1H, NH), 6.30 (s, 1H, NH), 5.33-5.24 (m, 3H), 4.86 (d, 1H, J=0.8 Hz), 4.27 (dd, 1H, J=5.2 Hz, J=12.2 Hz), 4.11-3.96 (m, 4H), 3.82-3.42 (m, 28H), 2.15-2.03 (m, 14H), 1.60 (bs, 2H), 1.26-1.24 (m, 16H), 0.87 (t, 3H, J=6.4 Hz). $^{13}$C NMR δ (ppm) (CDCl$_3$, 100 MHz) 173.5, 170.7, 170.2, 170.1, 169.9, 169.7, 97.7, 70.9, 70.7, 70.6, 70.5, 70.4, 70.3, 70.2, 70.1, 70.0, 69.9, 69.8, 69.6, 69.1, 68.5, 67.4, 66.2, 62.4, 39.2, 38.7, 36.6, 33.9, 31.9, 29.7, 29.6, 29.5, 29.4, 29.3, 25.8, 24.9, 22.6, 20.9, 20.8, 20.7, 20.6, 14.7. IR (neat film, cm$^{-1}$): 2926, 2857, 1747, 1656, 1537, 1369, 1228, 1136, 1081, 1048. LC-MS ESI m/z [M+H]$^+$: 896.

Preparation of Compounds 21 (Acetylated Man$_{C17}$) and 22 (Acetylated Man$_{C24}$)

Compounds 21 and 22 were synthesized using the same procedure described for product 20 except that lauric acid was respectively replaced by stearic acid 18 or pentacosanoic acid 19.

Data for compound 21:

R$_f$: 0.35 (DCM/MeOH: 90/10, v/v). $^1$H NMR δ (ppm) (CDCl$_3$, 400 MHz) 5.33-5.26 (m, 3H), 4.86 (d, 1H, J=0.8 Hz), 4.27 (dd, 1H, J=5.2 Hz, J=12.2 Hz), 4.10-3.96 (m, 4H), 3.68- 3.44 (m, 28H), 2.15-1.98 (m, 14H), 1.60 (bs, 2H), 1.26-1.24 (m, 28H), 0.87 (t, 3H, J =6.4 Hz). $^{13}$C NMR δ (ppm) (CDCl$_3$, 100 MHz) 172.5, 169.7, 169.1, 169.0, 168.9, 168.7, 96.7, 69.9, 69.7, 69.6, 69.5, 69.4, 69.3, 69.2, 69.1, 69.0, 68.8, 68.6, 68.1, 67.5, 66.4, 65.2, 61.4, 38.2, 37.6, 35.6, 30.9, 28.7, 28.6, 28.5, 28.4, 28.3, 24.8, 21.7, 19.9, 19.8, 19.7, 19.6, 13.1. IR (neat film, cm$^{-1}$): 2923, 2854, 1748, 1664, 1369, 1226, 1086, 1047. LC-MS ESI m/z [M+H]$^+$: 980.

Data for compound 22:

R$_f$: 0.43 (DCM/MeOH: 90/10, v/v). $^1$H NMR δ (ppm) (CDCl$_3$, 400 MHz) 5.36-5.23 (m, 3H), 4.87 (s, 1H), 4.28 (dd, 1H, J=2.8 Hz, J=11.8 Hz), 4.11-3.96 (m, 4H), 3.83-3.43 (m, 28H), 2.16-1.98 (m, 14H), 1.59 (bs, 2H), 1.26 (bs, 42H), 0.87 (t, 3H, J=6.8 Hz). $^{13}$C NMR δ (ppm) (CDCl$_3$, 100 MHz) 173.5, 170.7, 170.3, 170.0, 169.7, 97.7, 70.9, 70.8, 70.7, 70.6, 70.5, 70.4, 70.3, 70.2, 70.1, 70.0, 69.8, 69.6, 69.1, 68.5, 67.4, 66.2, 62.4, 39.4, 39.2, 38.7, 36.7, 33.9, 31.9, 29.7, 29.6, 29.5, 29.4, 29.3, 29.2, 25.8, 25.6, 22.7, 20.9, 20.8, 20.7, 14.1. IR (neat film, cm$^{-1}$): 2916, 2849, 1744, 1655, 1541, 1369, 1228, 1085, 1046, 910, 729. LC -MS ESI m/z [M+Na]$^+$: 1100.

Preparation of Compounds Man$_{C11}$ 2 (Comparative), Man$_{C17}$ 3 (Invention) and Man$_{C24}$ (Invention).

Compound 20 (17 mg, 14 μmol, 1 equiv.) was dissolved in 0.5 mL of anhydrous methanol. Sodium methoxide (1 mg, 11 μmol, 0.75 equiv.) was added and the reaction mixture was stirred at room temperature until all the reactant was hydrolyzed. The solution was then quenched with a resin Amberlite IR 120 hydrogen form (H$^+$) until an acidic pH (about ≃4-5) was reached. The resin was filtered with methanol and the filtrate was concentrated under reduced pressure. The residue was purified over a Sephadex G25 eluted with methanol to afford the compound Man$_{C11}$ 2(14 mg, 97%) as a yellow oil.

The same procedure was used to synthesize quantitatively compounds Man$_{C17}$ 3 and Man$_{C24}$ 4 starting from 21 and 22 respectively.

Data for compound Man$_{C11}$ 2 (comparative):

$^1$H NMR δ (ppm) (MeOD, 400 MHz) 4.70 (d, 1H, J=1.6 Hz), 3.91 (s, 2H), 3.75-3.71 (m, 3H), 3.63-3.44 (m, 24H), 3.35 (t, 2H, J =5.6 Hz), 3.29-3.25 (m, 2H), 2.09 (t, 2H, J =7.6 Hz), 1.50 (bs, 2H), 1.22-1.19 (m, 18H), 0.80 (t, 3H, J=6.8 Hz). $^{13}$C NMR δ (ppm) (MeOD, 100 MHz) 176.4, 172.9, 101.8, 74.7, 72.6, 72.2, 72.1, 72.0, 71.9, 71.7, 71.6, 71.5, 71.4, 71.3, 71.2, 71.1, 70.7, 70.6, 70.5, 68.7, 67.8, 62.9, 40.4, 39.9, 37.1, 34.7, 33.1, 30.8, 30.7, 30.5, 30.3, 27.1, 23.7, 14.5. IR (neat film, cm$^{-1}$): 3337, 2924, 2854, 1653, 1541, 1458, 1105, 1035. LC-MS ESI m/z [M+H]$^+$: 728.

Data for compound Man$_{C17}$ 3:

$^{31}$H NMR δ (ppm) (MeOD, 400 MHz) 4.76 (s, 1H), 3.91 (d, 2H, J=2.0 Hz), 3.76-3.72 (m, 3H), 3.63-3.42 (m, 24H), 3.35 (t, 2H, J=5.2 Hz), 3.30-3.25 (m, 2H), 2.09 (t, 2H, J=7.6 Hz), 1.50 (bs, 2H), 1.22-1.19 (m, 28H), 0.80 (t, 3H, J =6.4 Hz). 13C NMR δ (ppm) (MeOD, 100 MHz) 176.6, 172.9, 101.8, 74.6, 72.6, 72.2, 72.0, 71.9, 71.7, 71.6, 71.5, 71.4, 71.3, 71.2, 70.7, 70.6, 68.7, 67.8, 63.0, 40.5, 39.9, 37.0, 33.1, 30.8, 30.7, 30.6, 30.5, 30.3, 27.1, 23.8, 14.5. IR (neat film, cm$^1$): 3342, 2922, 2853, 1651, 1552, 1464, 1350, 1222, 1127, 1036, 1010. LC-MS ESI m/z [M+H]$^+$: 812.

Data for compound Man$_{C24}$ 4:

$^1$H NMR δ (ppm) (MeOD, 400 MHz) 4.72 (d, 1H, J=1.2 Hz), 3.94 (s, 2H), 3.79-3.74 (m, 3H), 3.65-3.44 (m, 24H), 3.36 (t, 2H, J =4.0 Hz), 3.30-3.24 (m, 2H), 2.09 (t, 2H, J =7.6 Hz), 1.52 (bs, 2H), 1.21(bs, 42H), 0.82 (t, 3H, J=6.8 Hz). $^{13}$C NMR δ (ppm) (MeOD, 100 MHz) 172.9, 169.5, 101.8, 74.6, 72.6, 72.1, 72.0, 71.9, 71.7, 71.6, 71.4, 71.3, 71.2, 70.6, 70.5, 67.8, 62.9, 40.4, 39.9, 37.1, 34.7, 33.1, 30.8, 30.7, 30.6, 30.5, 30.3, 27.1, 23.8, 14.5. IR (neat film, cm$^{-1}$): 3342, 2922, 2853, 1651, 1552, 1464, 1350, 1222, 1127, 1036, 1010. LC-MS ESI m/z [M+H]$^+$: 910.

Preparation of Compound 24

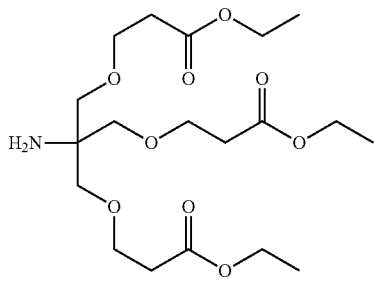

Compound 24 was prepared according to the procedure described by Kikkeri et al. (2009). Briefly, Tris(hydroxymethyl)aminomethane is first reacted with acrylonitrile in 1,4-dioxane for 24 h at room temperature to afford the corresponding tricyanide by Michael addition of the hydroxyl group. Hydrolysis of the cyano groups in HCl (37%) for 4 h followed by esterification under the influence of ethanol (reflux, 36 h) yielded the desired ethyl trimester 24.

Preparation of Compound 25.

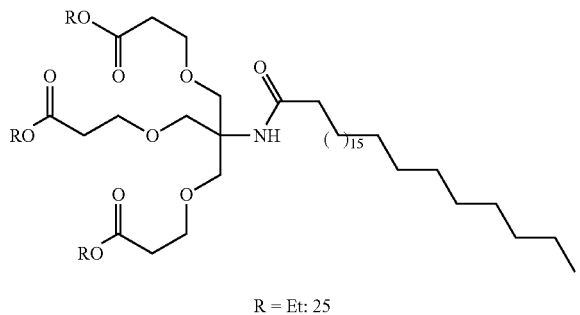

R = Et: 25

Tris (carboxyethoxyethyl) aminomethane 24 (302 mg, 0.72 mmol, 1.2 equiv.), pentacosanoic acid 19 (229 mg, 0.60 mmol, 1 equiv.) and HOBt (121 mg, 0.90 mmol, 1.5 equiv.) were dissolved in 10 mL of anhydrous acetonitrile. DCC (186 mg, 0.90 mmol, 1.5 equiv.) was added and the mixture was stirred overnight at reflux. The mixture was then cooled to room temperature and filtered. The filtrate was concentrated under reduced pressure and taken up in 200 mL of dichloromethane. The organic layer was washed first with a saturated aqueous solution of $NaHCO_3$, then with a saturated aqueous solution of ammonium chloride. The organic phase was dried over $Na_2SO_4$, filtered and evaporated under vacuum. The crude residue was purified by flash chromatography over a silica gel column eluted with Cyclohexane/AcOEt (7/3, v/v) to afford 25 (364 mg, 77%) as a white solid. $R_f$: 0.31 (Cyclohexane/AcOEt: 7/3, v/v). $^1H$ NMR δ (ppm) ($CDCl_3$, 300 MHz) 5.88 (s, 1H, NH), 4.04 (q, 6H, J=7.2 Hz), 3.65-3.57 (m, 12H), 2.42 (t, 6H, J=6.3 Hz), 2.04 (t, 2H, J=7.5 Hz), 1.50-1.41 (m, 53H), 0.78 (t, 3H, J=3.6 Hz). $^{13}C$ NMR δ (ppm) ($CDCl_3$, 75 MHz) 173.7, 171.8, 69.5, 67.1, 60.6, 59.9, 37.5, 35.3, 32.2, 30.0, 29.9, 29.8, 29.7, 29.5, 26.0, 23.0, 14.5, 14.3. IR (neat film, $cm^{-1}$): 2918, 2850, 1734, 1676, 1466, 1372, 1258, 1182, 1107, 1070, 1031. LC-MS (ESI) m/z $[M+H]^+$: 788.

Preparation of Compound 26 (Deprotection of Compound 25).

Triester 25 (176 mg, 0.23 mmol, 1 equiv.) was dissolved in a mixture of tetrahydrofuran (2 mL) and absolute ethanol (2 mL). To this solution was added an aqueous solution of sodium hydroxide (2 mL, 4 N). The mixture was stirred overnight and TLC analysis (Cyclohexane/AcOEt, 7/3, v/v) showed complete disappearance of the starting material. Solvents were evaporated under reduced pressure and the mixture was acidified by the addition of an aqueous solution of HCl, 1 N. Water was added (50 mL) and the resulting mixture was extracted three times with 50 mL of AcOEt. The combined organic extracts were dried over $Na_2SO_4$, filtered and concentrated under vacuum to afford 26 as a white solid (145 mg, 94%). The crude material was clean enough and used without further purification for the next step. $^1H$ NMR δ (ppm) ($C_5D_5N$, 300 MHz) 12.53 (s, 3H, 3 COOH), 4.15 (s, 6H), 3.95-3.86 (m, 6H), 2.80-2.74 (m, 6H), 2.30 (t, 2H, J=7.5 Hz), 1.71-1.19 (m, 44H), 0.86 (t, 3H, J=6.9 Hz). $^{13}C$ NMR δ (ppm) ($C_5D_5N$, 75 MHz) 176.3, 174.9, 77.9, 77.8, 69.8, 67.0, 60.1, 38.0, 35.2, 32.3, 30.0, 29.9, 29.7, 29.6, 29.4, 29.3, 29.2, 28.7, 26.0, 23.0, 19.5, 14.5. IR (neat film, $cm^{-1}$): 2917, 2850, 1718, 1554, 1467, 1308, 1194, 1109, 1069, 973, 829, 534. LC-MS (ESI) m/z $[M-H]^-$: 701.

Preparation of Compound 27.

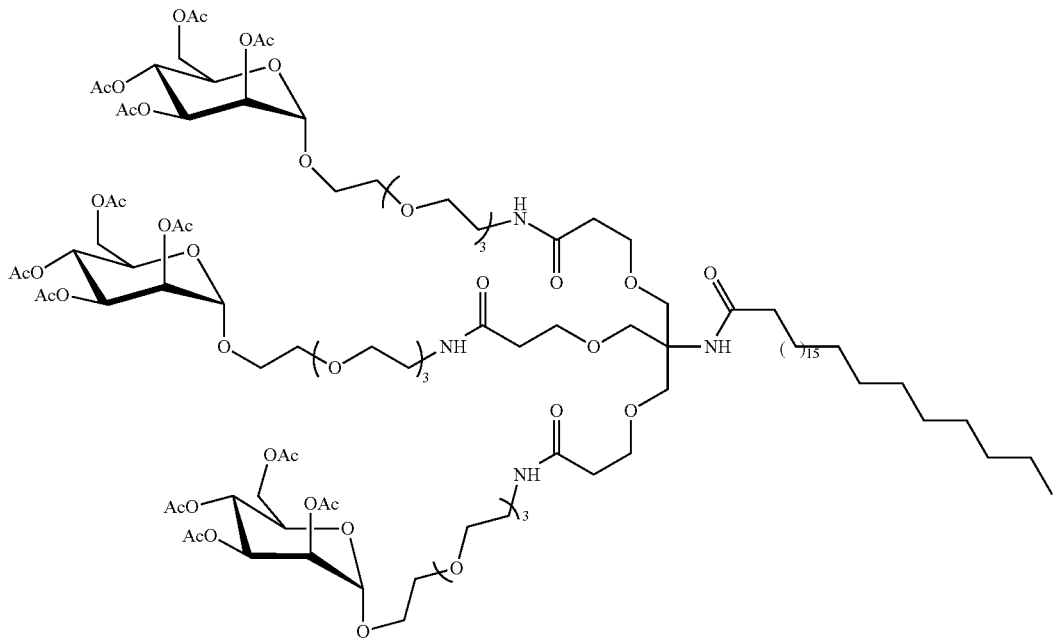

Compound 26 (87 mg, 0.12 mmol, 1 equiv.), amine mannose 13 (477 mg, 0.76 mmol, 6 equiv.), DIPEA (0.23 mL, 1.31 mmol, 10 equiv.) and HOBt (61 mg, 0.45 mmol, 3.5 equiv.) were dissolved in 8.5 mL of anhydrous tetrahydrofuran. To this solution was added HBTU (169 mg, 0.45 mmol, 3.5 equiv.). The reaction was left under stirring overnight at reflux. According to TLC analysis (DCM/MeOH, 9/1, v/v), the reaction was complete. The mixture was cooled to room temperature and concentrated under reduced pressure. The mixture was taken up in 100 mL of dichloromethane, washed first with a saturated aqueous solution of NaHCO3 and then with a saturated aqueous solution of ammonium chloride. The organic phase was dried over $Na_2SO_4$, filtered and evaporated under vacuum. The resulting oil was applied to a silica gel column, using first DCM/Acetone (5/5, v/v) as an eluent to eliminate impurities and then DCM/MeOH (9/1, v/v) to afford 27 (173 mg, 63%) as a yellow oil. $R_f$: 0.47 (DCM/MeOH: 90/10, v/v). $^1H$ NMR δ (ppm) (CDCl$_3$, 400 MHz) 6.47 (t, 3H, J=6.0 Hz, 3NH), 6.25 (s, 1H, NH), 5.32-5.14 (m, 9H), 4.84-4.77 (m, 3H), 4.23 (dd, 3H, J=4.8 Hz, J=14.6 Hz), 4.05-3.94 (m, 6H), 3.77-3.55 (m, 48H), 3.51-3.47 (m, 6H), 3.39-3.35 (m, 6H), 2.11-1.92 (m, 44H), 1.45-1.06 (m, 44H), 0.81 (t, 3H, J=6.4 Hz). $^{13}C$ NMR δ (ppm) (CDCl$_3$, 100 MHz) 171.2, 170.8, 170.7, 170.6, 170.5, 170.4, 170.3, 170.2, 170.0, 169.9, 169.8, 169.7, 169.6, 97.7, 97.5, 97.4, 72.3, 71.6, 71.5, 70.7, 70.6, 70.5, 70.4, 70.3, 70.1, 70.0, 69.9, 69.8, 69.7, 69.5, 69.0, 68.4, 67.3, 66.1, 62.4, 61.5, 59.6, 39.3, 39.2, 31.9, 29.6, 29.5, 29.3, 20.8, 20.7, 20.6, 14.1. IR (neat film, cm$^{-1}$): 2922, 1740, 1652, 1545, 1435, 1369, 1226, 1133, 1073, 1040, 977, 919. LC-MS (ESI) m/z [M-2Mannose+K]$^+$: 1591.

Preparation of Compound TriMan$_{C24}$ 5 (Invention)

Compound 27 (50 mg, 23 μmol, 1 equiv.) was dissolved in 1 mL of anhydrous methanol. Sodium methoxide (3 mg, 45 μmol, 2 equiv.) was added and the reaction mixture was stirred at room temperature until all the reactant was hydrolyzed. TLC analysis (DCM/MeOH, 9/1, v/v) revealed the appearance of a new product and the disappearance of the starting material into one product. The solution was then quenched with a resin Amberlite IR 120 hydrogen form (H$^+$) until an acidic pH (about ≃4-5) was reached. The resin was filtered with methanol and the filtrate was concentrated under reduced pressure. The residue was purified over a Sephadex G25 column eluted with methanol to afford compound TriMan$_{C24}$ 5 (37 mg, 96%) as a yellow oil. $^1H$ NMR δ (ppm) (MeOD, 400 MHz) 4.71 (d, 3H, J=1.2 Hz), 3.77-3.72 (m, 12H), 3.60-3.49 (m, 54H), 3.46 (t, 6H, J =5.6 Hz), 3.29 (t, 6H, J =5.6 Hz), 2.36 (t, 6H, J=6.4 Hz), 2.09 (t, 2H, J =8.0 Hz), 1.27-1.14 (m, 44H), 0.80 (t, 3H, J =6.8 Hz). $^{13}C$ NMR δ (ppm) (MeOD, 100 MHz) 176.5, 174.1, 101.8, 74.6, 72.6, 72.1, 71.6, 71.4, 71.3, 70.7, 70.2, 68.7, 68.6, 67.8, 62.9, 61.5, 40.5, 37.8, 37.5, 33.1, 30.9, 30.8, 30.7, 30.6, 30.5, 30.4, 27.1, 23.8, 14.5. IR (neat film, cm$^{-1}$): 3324, 2922, 2853, 1649, 1462, 1349, 1204, 1179, 1123, 1100, 974, 801, 722, 680. HRMS ESI m/z: Calculated for $C_{80}H_{152}N_4O_{34}$ [M+2H]$^{2+}$: 1713.0288. Found: 1713.0331.

Preparation of compound 29

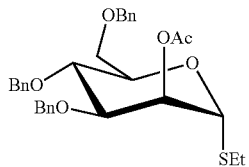

Compound 29 was prepared as described in Duffels et al., 2000. Briefly, the known fully acetylated glycosyl bromide (in Banoub, 1986) treated with 2,6-lutidine in dichloromethane/methanol (1/1, v/v) for 14 h at room temperature afforded stereoselectively peracytylated 1,2-exo-orthoacetate in 88% yield. Further deacetylation upon treatment with catalytic $K_2CO_3$ in methanol (14 h, room temperature, 90%) and subsequent benzylation (BnBr, NaH, TBAI, 0° C., 14 h, 60%) in DMF afforded perbenzylated 1,2-exo-orthoacetate. Treatment of the later compound with HgBr2 and EtSH (MS 4 angstrom, 60° C., 16 h) in MeCN gave the compound 29 hereabove.

Preparation of Compound 30.

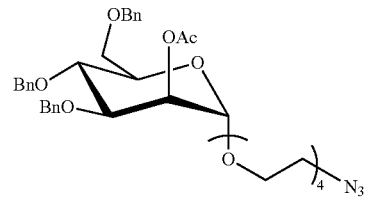

Compound 29 (111 mg, 0.21 mmol, 1 equiv.) and oligoethylene glycol 8 (83 mg, 0.38 mmol, 1.8 equiv.) were dissolved in 4 mL of anhydrous dichloromethane and molecular sieves (3 Å, 0.9 g) were added. The suspension was stirred at room temperature during thirty minutes and NIS (61 mg, 0.27 mmol, 1.3 equiv.) was added in one portion, followed immediately by TMSOTf (3 μL, 16 μmol, 0.07 equiv.). The reaction mixture was stirred at room temperature overnight and then filtered through Celite with Et$_2$O. The filtrate was concentrated under reduced pressure and diluted in 50 mL of Et$_2$O. The organic layer was washed twice with a saturated solution of sodium thiosulfate, dried over Na$_2$SO$_4$, filtered and evaporated under vacuum. The crude was purified by flash chromatography over a silica gel column eluted with Cyclohexane/AcOEt (6/4, v/v) to afford 30 (109 mg, 76%) as a colorless oil. $R_f$: 0.26 (Cyclohexane/AcOEt: 6/4, v/v). $^1H$ NMR δ (ppm) (CDCl$_3$, 300 MHz) 7.40-7.18 (m, 15H), 5.46-5.44 (m, 1H), 4.92-4.87 (m, 2H), 4.76-4.70 (m, 2H), 4.58-4.50 (m, 2H), 4.04 (dd, 1H, J=3.0 Hz, J=8.6 Hz), 3.96-3.63 (m, 19H), 3.36 (t, 2H, J=5.1 Hz), 2.17 (s, 3H). $^{13}C$ NMR δ (ppm) (CDCl$_3$, 75 MHz) 170.8, 138.8, 138.7, 138.5, 128.8, 128.7, 128.4, 128.3, 128.2, 128.1, 128.0, 98.3, 78.6, 75.6, 74.7, 73.9, 72.2, 71.8, 71.1, 70.5, 69.3, 69.1, 51.0, 21.6. IR (neat film, cm$^{-1}$): 2866, 2101, 1742, 1453, 1367, 1285, 1234, 1077, 1027, 978, 736, 697. MS (ESI) m/z [M+NH$_4$]$^+$: 712.

Preparation of Compound 31 (cleavage of acetyl group).

Acetylated mannose 30 (150 mg, 0.22 mmol, 1 equiv.) was dissolved in 1 mL of anhydrous methanol and catalytic potassium carbonate K$_2$CO$_3$ (2 mg, 0.01 mmol, 0.05 equiv.) was added. The reaction mixture was stirred at room temperature until all the reactant was hydrolyzed (Cyclohexane/AcOEt, 5/5, v/v). The solution was then quenched with a resin Amberlite IR 120 hydrogen form (H$^+$) until an acidic pH (about ≃4-5) was reached. The resin was filtered with methanol and the filtrate was concentrated under reduced pressure. The residue was purified over a Sephadex G25 column eluted with methanol to afford the compound 31 (135 mg, 96%) as a yellow oil. $R_f$: 0.43 (Cyclohexane/AcOEt: 5/5, v/v). $^1H$ NMR δ (ppm) (CDCl$_3$, 300 MHz) 7.37-7.27 (m, 13H), 7.21-7.18 (m, 2H), 4.98 (d, 1H, J=1.5 Hz), 4.85 (d, 1H, J=10.8 Hz), 4.76-4.66 (m, 3H), 4.57-4.51 (m, 2H), 4.12-4.11 (m, 1H), 3.91-3.63 (m, 19H), 3.37 (t, 2H, J=5.1 Hz), 2.66 (s, 1H, OH). $^{13}C$ NMR δ (ppm) (CDCl$_3$, 75 MHz) 138.8, 138.7, 138.4, 128.9, 128.7, 128.4, 128.3, 128.2, 128.1, 128.0, 99.8, 80.6, 75.5, 74.8, 73.9, 72.3, 71.5, 71.1, 71.0, 70.5, 70.4, 69.4, 68.7, 67.0, 51.1. IR (neat film, cm$^{-1}$): 2867, 2101, 1453, 1362, 1284, 1210, 1096, 1059, 1027, 842, 735, 697. HRMS (ESI) m/z: Calculated for $C_{35}H_{45}N_3O_9$ [M+Na]$^+$: 674.3053. Found: 674.3080.

Preparation of Compound 32

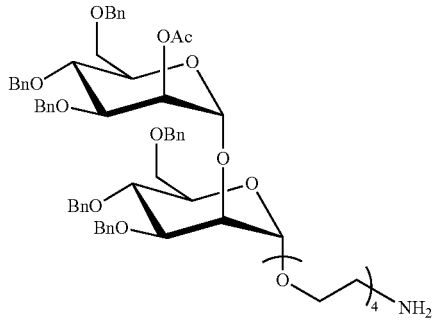

Mannose derivative 29 (63 mg, 0.12 mmol, 1 equiv.) and deprotected mannose 31 (91 mg, 0.14 mmol, 1.1 equiv.) were dissolved in a mixture of 1 mL of anhydrous dichloromethane and 1 mL of anhydrous Et$_2$O. Molecular sieves (3 Å, 0.7 g) were added. The suspension was stirred at room temperature during thirty minutes and NIS (39 mg, 0.17 mmol, 1.4 equiv.) was added in one portion, followed immediately by TMSOTf (2 μL, 11 μmol, 0.09 equiv.). The reaction mixture was stirred at room temperature overnight and then filtered through Celite with Et2O. The filtrate was concentrated under reduced pressure and diluted in 100 mL of Et$_2$O. The organic layer was washed twice with a saturated solution of sodium thiosulfate, dried over Na$_2$SO$_4$, filtered and evaporated under vacuum. The crude was purified by flash chromatography over a silica gel column eluted with Cyclohexane/AcOEt (7/3, v/v) to afford the desired compound 32 (76 mg, 58%) as a colorless oil. R$_f$: 0.15 (Cyclohexane/AcOEt: 7/3, v/v). $^1$H NMR δ (ppm) (CDCl$_3$, 300 MHz) 7.41-7.18 (m, 30H), 5.60-5.58 (m, 1H), 5.14 (d, 1H, J=1.2 Hz), 4.96 (d, 1H, J=1.2 Hz), 4.91 (d, 1H, J=2.4 Hz), 4.88 (d, 1H, J=2.7 Hz), 4.73-4.69 (m, 4H), 4.63-4.43 (m, 5H), 4.11-4.09 (m, 1H), 4.06-3.51 (m, 25H), 3.38 (t, 2H, J=5.1 Hz), 2.16 (s, 3H). $^{13}$C NMR δ (ppm) (CDCl$_3$, 75 MHz) 170.5, 138.9, 138.8, 138.6, 138.4, 128.8, 128.7, 128.6, 128.5, 128.2, 128.1, 128.0, 127.9, 127.8, 100.0, 99.2, 80.1, 78.6, 75.6, 75.4, 75.2, 75.1, 74.8, 73.8, 73.7, 72.4, 72.3, 71.1, 71.0, 70.5, 70.4, 69.7, 69.5, 69.2, 67.0, 51.1, 21.6. IR (neat film, cm$^{-1}$): 2865, 2102, 1743, 1496, 1453, 1363, 1284, 1234, 1137, 1078, 1053, 1027, 978, 910, 844. HRMS (ESI) m/z: Calculated for $C_{64}H_{75}N_3O_{15}$ [M+Na]$^+$: 1143.5542. Found: 1143.5559.

Preparation of Compound 33

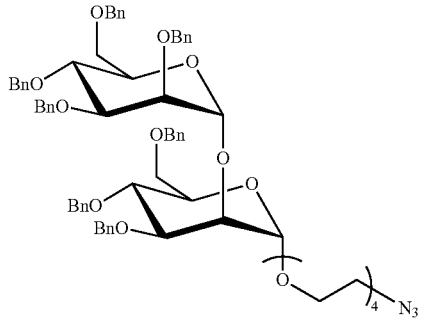

Compound 32 (76 mg, 67 μmol, 1 equiv.) was dissolved in 0.75 mL of tetrahydrofuran. Triphenylphosphine (20 mg, 76 μmol, 1.1 equiv.) and water (2 μL, 111 μmol, 1.5 equiv.) were added. The reaction mixture was allowed to stir overnight at room temperature and was concentrated under reduced pressure to eliminate THF and water. The residue was purified by flash chromatography over a silica gel column eluted first with DCM/MeOH (9/1, v/v) to remove the impurities and then with a mixture DCM/MeOH/NEt3 (80/19/1, v/v/v) to afford compound 33 (45 mg, 61%) as a colorless oil. R$_f$: 0.30 (DCM/MeOH/NEt$_3$: 80/19/1, v/v/v). $^1$H NMR δ (ppm) (CDCl$_3$, 300 MHz) 7.36-7.16 (m, 30H), 5.58-5.55 (m, 1H), 5.12-5.11 (m, 1H), 4.94 (s, 1H), 4.88 (d, 1H, J=2.1 Hz), 4.85 (d, 1H, J=2.1 Hz), 4.71-4.67 (m, 4H), 4.60-4.40 (m, 5H), 4.09-4.07 (m, 1H), 4.03-3.48 (m, 25H), 3.14 (s, 2H, NH$_2$), 2.87 (t, 2H, J=4.5 Hz), 2.14 (s, 3H). $^{13}$C NMR δ (ppm) (CDCl$_3$, 75 MHz) 170.5, 138.9, 138.8, 138.6, 138.4, 128.7, 128.6, 128.5, 128.2, 128.0, 127.9, 127.8, 100.0, 99.2, 80.1, 78.5, 75.6, 75.4, 75.2, 75.0, 74.7, 73.8, 73.7, 72.9, 72.4, 72.3, 72.2, 71.0, 70.6, 70.5, 69.7, 69.4, 69.1, 67.1, 41.8, 21.5. IR (neat film, cm$^{-1}$): 2866, 1743, 1496, 1453, 1364, 1286, 1234, 1137, 1078, 1055, 1028, 980, 912, 843. HRMS (ESI) m/z: Calculated for $C_{64}H_{77}N_1O_{15}$ [M+H]$^+$: 1100.5371. Found: 1100.5395.

Preparation of Compound TriDiMan$_{C24}$ 6.

Tricarboxylic acid 26 (9 mg, 13 μmol, 1 equiv.), amine dimannose 33 (45 mg, 41 μmol, 3.2 equiv.), DIPEA (25 μL, 142 μmol, 10.5 equiv.) and HOBt (7 mg, 50 μmol, 3.5 equiv.) were dissolved in 1 mL of anhydrous tetrahydrofuran. To this solution was added HBTU (18 mg, 50 μmol, 3.5 equiv.). The reaction was left stirring overnight at reflux. According to TLC analysis (DCM/MeOH, 95/5, v/v), the reaction was complete. The mixture was cooled to room temperature and concentrated under reduced pressure. The resulting crude was applied to a silica gel column, using first DCM/Acetone (5/5, v/v) as an eluent to eliminate impurities and then DCM/MeOH (95/5, v/v) to afford the fully protected (benzylated and acetylated) expected product (14 mg, 27%) as a yellow oil. R$_f$: 0.13(DCM/MeOH: 95/5, v/v). $^1$H NMR δ (ppm) (CDCl$_3$, 400 MHz) 7.28-7.06 (m, 90H), 6.56 (s, 3H, NH), 5.93 (s, 1H, NH), 5.46-5.44 (m, 3H), 5.01-5.00 (m, 3H), 4.83 (d, 3H, J=1.6 Hz), 4.78 (d, 3H, J=1.6 Hz), 4.75 (d, 3H, J=1.6 Hz), 4.60-4.56 (m, 12H), 4.49-4.31 (m, 15H), 3.96 (t, 3H, J=2.0 Hz), 3.90 (dd, 4H, J=2.8 Hz, J=9.4 Hz), 3.87-3.82 (m, 5H), 3.76 (dd, 4H, J=2.8 Hz, J=9.4 Hz), 3.73-3.35 (m, 80H), 2.42 (t, 2H, J=6.0 Hz), 2.33 (t, 6H, J=5.2 Hz), 2.04 (s, 9H), 1.27-1.13 (m, 44H), 0.81 (t, 3H, J=6.8 Hz). $^{13}$C NMR δ (ppm) (CDCl$_3$, 100 MHz) 171.5, 170.1, 138.4, 138.3, 138.2, 138.0, 128.4, 128.3, 128.2, 128.1, 127.8, 127.7, 127.6, 127.5, 127.4, 99.6, 98.8, 79.6, 78.1, 75.2, 75.1, 74.9, 74.6, 74.4, 73.4, 73.3, 72.0, 71.9, 71.8, 70.6, 70.4, 70.1, 70.0, 69.9, 69.3, 69.1, 68.7, 67.4, 66.7, 59.6, 39.2, 37.2, 31.9, 29.8, 29.7, 29.6, 29.5, 29.4, 25.7, 22.7, 21.1, 14.1. IR (neat film, cm$^{-1}$): 2922, 2853, 1743, 1454, 1365, 1235, 1099, 1058, 1028, 737, 698. HRMS (ESI) m/z: Calculated for $C_{230}H_{296}N4O_{52}$ [M+H]$^+$: 3946.0641. Found: 3946.0631.

This intermediate (24 mg, 4 μmol) was dissolved in 0.5 mL of anhydrous methanol and catalytic potassium carbonate K$_2$CO$_3$ was added. The reaction mixture was stirred at room temperature until a new product appeared (DCM/MeOH, 95/5, v/v). The solution was then quenched with a resin Amberlite IR 120 hydrogen form (H$^+$) until an acidic pH (about ≃4-5) was reached. The resin was filtered with methanol and the filtrate was concentrated under reduced pressure. The residue was directly engaged in the hydrogenolysis step. Under an argon atmosphere, Pd/C 20% (5 mg) was added to the previous crude dissolved in 0.5 mL of anhydrous methanol. The resulting mixture was degassed for thirty minutes under the argon atmosphere. Then it was submitted to a hydrogen atmosphere, at 1 atm pressure, overnight. The final mixture was filtered through a pad of Celite with methanol and the filtrate was concentrated under reduced pressure. TLC analysis (DCM/MeOH, 9/1, v/v) revealed the appearance of a new product and the disappearance of the starting material into one product. The residue was then quenched with a resin Amberlite IR 120 hydrogen form (H$^+$) until an acidic pH (about ≃4-5) was reached. The resin was filtered with methanol and the filtrate was concentrated under reduced pressure. The residue was purified over a Sephadex G25 column eluted with methanol to afford the compound TriDiMan$_{C24}$ 6 (13 mg, 97% over two steps) as a yellow oil. $^1$H NMR δ (ppm) (MeOD, 400 MHz) 5.04 (s, 3H), 4.90 (s, 3H), 3.78-3.71 (m, 14H), 3.62-3.48 (m, 76H), 3.31 (t, 6H, J=4.8 Hz), 2.37 (t, 6H, J=5.6 Hz), 2.10 (t, 2H, J=7.6 Hz), 1.29-1.14 (m, 44H), 0.82 (t, 3H, J=6.0 Hz). $^{13}$C NMR δ (ppm) (MeOD, 100 MHz) 172.7, 169.1, 101.8, 100.2, 81.0, 80.6, 76.0, 75.7, 75.0, 74.7, 74.4, 72.6, 72.5, 72.1, 71.9, 71.7, 71.6, 71.5, 71.4, 71.3, 71.1, 70.7, 70.5, 70.2, 69.1, 68.9, 68.7, 68.1, 68.0, 63.1, 62.2, 40.5, 37.6, 36.1, 35.7, 33.1, 30.8, 30.7, 30.0, 29.6, 23.7, 14.5. IR (neat film, cm$^{-1}$): 3408, 2924, 2853, 1716, 1647, 1404, 1195, 1128, 1042, 1013, 770, 696, 642, 576. HRMS ESI m/z: Calculated for C$_{98}$H$_{182}$N$_4$O$_{49}$ [M+2H]$^{2+}$: 1102.6069. Found: 1102.5831.

Preparation of Trimannoside 5-AF Labelled with Fluorescent Dye Alexa Fluor 633.

Compound TriMan$_{C24}$ 5 (2 mg, 8.3 10$^{-4}$ mmol, 1 equiv) and NHS-Alexa Fluor 633 (0.1 mg, mmol, 0.1 equiv) were dissolved in 0.1 mL of water. A catalytic amount of DMAP was added to the solution and the reaction mixture was stirred overnight in the dark. The solution was then purified over a Sephadex G25 column with precise volumes of water. The first isolated fractions correspond to Alexa Fluor 633 labeled-trimannoside 5-AF. First, a UV titration was carried out to obtain a calibration curve for the NHS-Alexa 633. The fractions purified by Sephadex were then titrated by UV and the percentage for fixation of the fluorescent dye was determined: a value of 1% was evaluated by this method.

Preparation of Man$_{insatC24}$

Man$_{insatC24}$ was prepared according the same procedure as described for the preparation of Man$_{C11}$ except that lauric acid was replaced by 10,12-pentacosadiynoic acid.

$^1$H NMR δ (ppm) (MeOD, 400 MHz) 4.70 (d, 1H, J=1.2 Hz), 3.90 (s, 2H), 3.75-3.72 (m, 4H), 3.63-3.45 (m, 26H), 3.36-3.25 (m, 4H), 2.16-2.08 (m, 6H), 1.51-1.19 (m, 32H), 0.79 (t, 3H, J=6.8 Hz).

$^{13}$C NMR δ (ppm) (MeOD, 100 MHz) 176.5, 172.8, 101.8, 78.0, 77.9, 74.6, 72.6, 72.2, 72.0, 71.7, 71.6, 71.5, 71.4, 71.3, 71.2, 71.1, 70.7, 70.6, 70.5, 68.7, 67.8, 66.5, 63.0, 40.3, 40.2, 37.1, 33.1, 30.8, 30.7, 30.6, 30.3, 30.2, 30.1, 30.0, 29.9, 29.8, 29.6, 27.0, 23.4, 19.7, 14.5.

IR (neat film, cm$^{-1}$): 3366, 2925, 2855, 1654, 1541, 1507, 1458, 1101, 669, 650.

R$_f$: 0.57 (DCM/MeOH: 7/3, v/v).

MS ESI m/z [M+K]$^+$: 942.

Preparation of TriMan$_{insatC24}$

TriMan$_{insatC24}$ was prepared according the same procedure as described for the preparation of TriMan$_{C24}$ except that pentacosanoic acid was replaced by 10,12 -pentacosadiynoic acid.

$^1$H NMR δ (ppm) (MeOD, 400 MHz) 4.64 (d, 3H, J=1.6 Hz), 3.70-3.64 (m, 12H), 3.57-3.40 (m, 60H), 3.31 (t, 3H, J=8.4 Hz), 3.26 (t, 3H, J=4.4 Hz), 2.37 (t, 6H, J=6.4 Hz), 2.11-2.06 (m, 6H), 1.44-1.09 (m, 32H), 0.74 (t, 3H, J=6.0 Hz).

$^{13}$C NMR δ (ppm) (MeOD, 100 MHz) 174.7, 168.9, 101.8, 78.0, 77.9, 74.6, 72.6, 72.2, 71.6, 71.4, 71.3, 70.4, 70.2, 69.6, 68.7, 68.6, 67.8, 63.0, 62.0, 41.9, 40.9, 37.1, 33.1, 30.8, 30.7, 30.6, 30.5, 30.3, 302, 30.1, 29.9, 29.6, 27.2, 23.8, 19.7, 14.4.

IR (neat film, cm$^{-1}$): 3353, 2924, 1716, 1636, 1350, 1182, 1095, 1035, 1009, 837, 669.

R$_f$: 0.18 (DCM/MeOH: 90/10, v/v).

HRMS ESI m/z: Calculated for C$_{80}$H$_{144}$N$_4$O$_{34}$ [M+H]$^+$: 1705.9735. Found: 1705.9759.

Preparation of TriDiMan$_{insatC24}$

DiMan$_{insatC24}$ was prepared according a procedure similar to that used for the preparation of TriDiMan$_{C24}$ except that:

pentacosanoic acid was replaced by 10,12-pentacosadiynoic acid, and before the coupling with 10,12-pentacosadiynoic acid, the benzyl groups of compound 33 were replaced by acetyl group so as to provide compound 108 (as illustrated in FIG. 3E).

$^1$H NMR δ(ppm) (MeOD, 400 MHz) 4.87 (s, 3H), 4.73 (s, 3H), 3.64-3.50 (m, 14H), 3.46-3.20 (m, 76H), 2.97-2.93 (m, 6H), 2.33 (t, 6H, J=6.8 Hz), 2.09-1.96 (m, 6H), 1.08-1.05 (m, 32H), 0.66 (t, 3H, J=6.8 Hz).

$^{13}$C NMR δ (ppm) (MeOD, 100 MHz) 173.7, 168.8, 104.2, 101.2, 80.6, 80.4, 75.1, 74.7, 72.5, 72.2, 72.1, 71.9, 71.8, 71.7, 71.6, 71.4, 69.4, 69.1, 68.9, 68.7, 68.6, 68.0, 63.2, 63.1, 42.2, 37.0, 34.8, 33.7, 33.1, 30.8, 30.7, 30.6, 30.5, 30.4, 30.2, 29.5, 28.1, 27.0, 26.0, 23.7, 19.7, 14.4.

IR (neat film, cm$^{-1}$): 3353, 2924, 1716, 1636, 1350, 1182, 1095, 1035, 1009, 837, 669.

Determination of critical micelle concentrations (CMCs) and size of particles.

The hydrodynamic diameters of micelles of glycolipids were measured in water using a Zetasizer Nano ZS system (Malvern Instruments). The CMCs were measured using pyrene as an extrinsic fluorescent probe and were carried out as described (Perino et al., 2011). Briefly, a range of glycolipid samples were dissolved in water (1 ml), with concentrations ranging from 1.0 to 0.001 mg/ml. A stock solution of pyrene (1 mM) was prepared in dimethyl sulfoxide and was added to each sample. Fluorescent emission of pyrene was measured at 25° C. using a Fluorolog spectrofluorometer (Jobin Yvon, Horiba).

The intensities of fluorescence emission were determined at 374 nm (I$_{374}$) and at 383 nm (I$_{383}$), with an excitation at a 339 nm wavelength. The ratios I$_{374}$/I$_{383}$ were calculated and plotted against the glycolipid concentration. The CMC value was determined at the intersection of the two straight lines.

Surface Plasmon Resonance (SPR).

SPR experiments were performed using a Biacore 3000. Immobilisation of human DC-SIGN (Lys62-Ala404, from R§D Systems) on a CM5 sensor chip (GE-Healthcare, Uppsala, Sweden) was performed by injecting 70 μL of DC-SIGN (50 μg/ml in formate buffer, pH 4.3) onto the surface activated with N-Ethyl-N'-dimethylaminopropyl carbodiimide (EDC)/ N-hydroxysuccinimide (NHS), which gave a signal of approximately 8000 RU, followed by 20 μL of ethanolamine hydrochloride, pH 8.5, to saturate the free activated sites of the matrix. Biosensor assays were performed with HEPES-buffered saline (10 mM HEPES, 150 mM sodium chloride, pH 7.4) containing 0.005% surfactant P20 and 5 mM CaCl$_2$ as a running buffer. All binding experiments were carried out at 25° C. with a constant flow rate of 20 μl/min. The different compounds dissolved in the running buffer (0.39 to 50 μM) were injected for 3 min, followed by a dissociation phase of 3 min. The sensor chip surface was regenerated after each experiment by injecting 10 µL of EDTA 0.5 M pH 8.0. A simple channel activated by EDC/NHS and deactivated with ethanolamine was used as control. The kinetic parameters were calculated using the BIAeval 4.1 software. Analysis was performed using the simple Langmuir binding model with separate $k_a/k_d$ ($k_{on}/k_{off}$). The specific binding profiles were obtained after subtracting the response signal from the control channel and from blank-buffer injection. The fitting to each model was judged by the chi square value and randomness of residue distribution compared to the theoretical model (Langmuir binding 1:1).

Cell Lines

MAGI-CCR5 cells are HeLa-CD4-LTR-LacZ cells expressing both CXCR4 and CCR5 coreceptors (received from NIH AIDS Research and Reference Program, from Dr. Julie Overbaugh (Chackerian, et al., 1997)). HEK293T cells were used for HIV-1 production. MCF-7 cells were used for viability tests. These cell lines were cultured at 37° C. and 5% $CO_2$ in Dulbecco's modified Eagle's medium (DMEM; Lonza) supplemented with gentamycin and 10% (v/v) heat-inactivated fetal bovine serum (FBS).

BHK-21 hamster kidney cells were cultured at 37° C. in Glasgow MEM (Gibco) with 10% FBS. The C6/36 *Aedes albopictus* cell line was cultured in Leibovitz L15 medium (Gibco) supplemented with 5% FBS and 10% tryptose at 22° C. in the absence of $CO_2$, and was infected at 28° C. in 5% $CO_2$.

Generation of Human Monocyte-Derived Dendritic Cells

Elutriated human monocytes were obtained from the French Blood Bank (Etablissement Francais du Sang, Strasbourg, France). To generate monocyte-derived dendritic cells, monocytes were cultured at 37° C. and 5% $CO_2$ in RPMI 1640 medium (Lonza) supplemented with 10% FBS, gentamycin, 50 ng/ml of recombinant human granulocyte macrophage colony stimulating factor (GM-CSF; Immuno-Tools) and 10 ng/ml of recombinant human interleukin-4 (rhIL-4; ImmunoTools), with readdition of cytokines at day 3. Cells were harvested on day 5 and specific cell marker expression (CD1a, DC-SIGN) was characterized by flow cytometry on a FACSCalibur flow cytometer (Beckton-Dickinson) and analysed with the CellQuest Pro software (BD Biosciences).

Cell Viability Assays

The effect of mannoside glycolipids on cell viability was assessed by monitoring activity of mitochondrial deshydrogenases, using the MTT (3-(4,5-dimethylthiazol-2-yl)-2,5-diphenyltetrazolium bromide) colorimetric procedure, following MTT reduction to MTT formazan. Briefly, confluent MCF-7 cells plated in 96-well culture plates were treated with different concentrations of compounds (in 0.1% DMSO), with either medium alone (positive control), with 0.1% DMSO, or with amytal (30 mM; positive control). After 24 h, MTT solution (300 µg/mL) in cell culture medium was added for 2 hours at 37° C. The medium was then removed and the formazan crystals were dissolved in 100 µL of DMSO. The optical density of the resulting solutions was colorimetrically determined at 595 nm using a microplate reader (BioTek EL808). In this assay, control viable cells had a viability index of 100, while that of cells exposed to cytotoxic compounds would be less than 100. To evaluate the effect of mannoside glycolipids on primary human cells, DCs were treated with compounds at the indicated concentrations, and incubated at 37° C. for 24 h. Cells were resuspended in PBS and Sytox Red dead cell stain for 633 nm excitation (20 nM; Invitrogen) was added prior analysis by flow cytometry.

Flow Cytometric Analyses

Expression of cell markers (CD1a, DC-SIGN) was determined in FACS buffer (1% FBS in PBS) at 4° C. for 20 min, using specific antibodies and their corresponding isotype controls (from BD-Pharmingen): CD1a-allophycocyanin (APC) (HI149), CD209/DC-SIGN -PerCP-Cy5.5 (DCN46).

Competition Assays Between $TriMan_{C24}$ and HIV-1 gp120

Human DCs ($1 \times 10^5$ in 100 µl) were aliquoted in a 96-well microtiter plate in RPMI 1640 medium without FBS. To assess the binding of HIV-1 glycoprotein 120, FITC conjugated recombinant gp120 HIV-1 IIIB (ImmunoDiagnostics Inc, Woburn, Mass. U.S.A.) was added to the cells (final concentration of 5 µg/ml) and incubated for 45 min at 37° C. For competition assays, cells were pretreated with either mannan (100 µg/ml final) or $TriMan_{C24}$ (100 µM) for 30 min at 37° C., followed by incubation with gp120-FITC for 45 min at 37° C. After washing with HBSS buffer (Lonza), expression of fluorescence intensity was analyzed on a FACSCalibur flow cytometer with the CellQuest Pro software Confocal Microscopy Human DCs ($1 \times 10^5$ in 100 µl of RPMI medium) were exposed to Alexa633-labeled $TriMan_{C24}$ (100 µM final) for 10 min at 37° C. When indicated, transferrin-Alexa488 (Invitrogen) was also added for 10 min at 37° C. Cells were then washed and fixed with 4% paraformaldehyde for 15 min at room temperature. Nuclei were labeled with DAPI (1 µg/ml final) for 5 min. Slides were mounted using Prolong-Antifade (Molecular Probes). Samples were imaged with a confocal microscope (Zeiss LSM 700) and images analyzed with Adobe Photoshop.

To visualize the effect on DC-SIGN, cells were either left untreated or exposed to TriMan (100 µM final) for 45 min at 37° C., fixed with 4% paraformaldehyde for 15 min at room temperature, washed, permeabilized with 0.1% Triton X-100 for 3 min at 20° C., washed and labeled with an anti-DC-SIGN primary monoclonal antibody clone 111H2 (Canard, et al., 2011), followed by a secondary FITC-labeled anti-mouse-IgG (Southern Biotech). Nuclei were labeled with DAPI. Slides were mounted and processed as above.

HIV-1 Production

Molecular clones of HIV-1 NL4-3 (X4 strain) and an NL4-3 R5-tropic version (Schaeffer, et al., 2004) were transfected into HEK293T cells and viruses harvested from the supernatants 48 h later. All transfections were performed using calcium phosphate for precipitation of DNA. Viral stocks were normalized based on their p24 Gag content, measured in an enzyme-linked immunosorbent assay (ELISA) using the Innotest HIV antigen mAb kit (Innogenetics). Viral infectivity of the stocks was controlled with the indicator MAGI-CCR5 cell line, and enumerating blue cells by light microscopy.

HIV-1 Trans-Infection Assays $Man_{C1}$, $Man_{C17}$ (comparative) and compounds of the invention ($Man_{C24}$, $Man_{C17}$, $TriMan_{C24}$, $TriDiMan_{C24}$, $TriMan_{insatC24}$ and $Man_{insatC24}$) were serially diluted in water. Human DCs ($1 \times 10^5$ in 200 µl) were pre-treated with different concentrations of compounds, or mannan (Sigma) or culture medium alone, in RPMI 1640 medium containing 10% FBS for 45 min at 37° C., prior infection with HIV-1 (100 ng of p24Gag) for 3 h. Excess free virus and molecules were removed by three washes. DCs were then cocultured with MAGI -CCR5 cells ($1 \times 10^5$) at 37° C. plated in a 48-well plate. After two days, viral infection of MAGI-CCR5 cells was quantitated following beta-galactosidase assays and enumerating blue cells by light microscopy.

$IC_{50}$ Determinations

The $IC_{50}$ were determined by serial dilution of each compound. The trans-infection assays were repeated a minimum of three times, and the $IC_{50}$ determined using Kaleida-Graph.

Dengue Virus (DV2) Production

The plasmid pDV2, strain 16681 (5 µg) (gift of Dr. E. Harris, University of California, Berkeley, U.S.A.) was linearized with XbaI, phenol-chloroform extracted, ethanol and NaCl precipitated, and resuspended in RNase-free water. RNA was produced by in vitro transcription, performed in a 50 µl reaction using the T7 RiboMax Large Scale RNA Production Systems (Promega) with an additional 7 mG(ppp)A RNA Cap Structure Analog (New England BioLabs), according to the manufacturer's instructions. The mixture was incubated for 4 h at 37° C. It was used without further purification to transfect BHK-21 cells ($10^6$ cells/well) in a 6-well plate, using the Lipofectamine RNAiMax kit (Invitrogen). The RNA mixture (50 µl) in Opti-MEM (200 µl) was added to Lipofectamine (50 µl) in Opti-MEM (200 µl), incubated for 20 min and added to $10^6$ cells. After 3 h, the supernatant was removed and cells cultured in complete L15 medium. On days 3, 4 and 5, supernatants were collected, spun down to remove cells and stored in aliquots at −80° C.

DV2 was produced in C6/36 mosquito cells cultured at 28° C., by infection with viral supernatants from BHK cells. C6/36 supernatants were collected every 2 days up to day 16, and stored in aliquots at −80° C.

Effect of Compounds on DV2 Infections

Compounds of the invention ($TriMan_{C24}$, $TriMani_{nsatC24}$) were serially diluted in water. Human DCs ($2.5 \times 10^5$ in 200 µl) in 48-well plates were pre-treated with different concentrations of compounds or culture medium alone, in RPMI 1640 medium without for 30 min at 37° C. They were exposed to DV-2 at a multiplicity of infection of 1.0, for 2 h at 37° C. Cells were washed and cultured in complete RPMI medium (condition 1) or in complete medium containing the tested compounds ($TriMan_{C24}$, $TriMan_{nsatC24}$) (condition 2). After 48 h, supernatants were titered and cells were subjected to intracellular detection of viral antigens. DCs were fixed with 4% (v/v) paraformaldehyde and permeabilized with 0.1% (v/v) Triton X-100 for 3 min at room temperature. After washing, they were labeled with mouse anti-DV type 2 monoclonal antibody (3H5.1, Millipore) and stained with APC -conjugated rat anti-mouse IgG1. Fluorescence intensity of the cells was analyzed by flow cytometry (FACSCalibur, Becton Dickinson), using the Cell Quest Pro software.

DV2 Titration

Virus production in cell supernatants was titered using a flow cytometry-based assay as described (Lambeth et al., 2005). Cells were fixed and permeabilized with 0.1% Triton X-100 for 5 min at room temperature. After washing, they were labeled for intracellular expression of viral envelope protein with mouse anti-DV type 2 monoclonal antibody (3H5.1, Millipore) and stained with APC rat anti-mouse IgG1 (BD Pharmingen).

b. Results

Solubility, Critical Micelle Concentration (CMC) and Cellular Toxicity of the Compounds of the Invention All synthesized compounds of the invention were solubilized in water by simple stirring. These molecules exhibited no cytotoxicity on cells, as shown by viability assays on a human cell line and by dead cell staining of DCs, at concentrations lower than 125 µM for unsaturated compounds, and at least up to 500 µM for saturated compounds.

When compounds were dissolved in water at 0.5 mg/ml, molecules $Man_{C17}$, $Man_{C24}$ and $TriMan_{C24}$ were able to auto-organize in micelles, at a critical micelle concentration (CMC) of respectively 112, 97 and 109 µM (as described in Supplementary data). The hydrodynamic diameter of these micelles was respectively 17, 17 and 39 nm. Noticeably, $TriDiMan_{C24}$ and comparative molecules $Man_{C1}$ and $Man_{C11}$ were unable to form micelles.

Binding Affinity for DC-SIGN CRD

The binding affinity of mannoside derivatives for the carbohydrate recognition domain (CRD) of DC-SIGN was assessed by surface plasmon resonance (SPR).

A CM5 sensor chip was functionalized with the DC-SIGN CRD, and increasing concentrations of the various compounds, mannan as a positive control and octaethyleneglycol (OEG) as a negative control, were injected over the chip surface. The association (kon) and dissociation (koff) rate constants and the resulting dissociation equilibrium constant (Kd=koff/kon) for each assessed compound were determined (see Table 1 hereunder). As expected, mannan bound efficiently to the surface, while OEG was unable to bind. $Man_{C1}$ and $Man_{C11}$ were unable to bind, $Man_{C17}$ bound with a low affinity, while $Man_{C24}$ exhibited an optimal affinity in the sub-micromolar range. These data indicated that the affinity of the synthesized mannoside derivatives for DC-SIGN correlated with the length of the lipid chain, suggesting that the lipid moiety enhanced the binding capacity of the mannose polar head in a cooperative manner. $TriMan_{C24}$ and $TriDiMan_{C24}$ also efficiently bound to DC-SIGN, with Kd in the low micromolar range, although they presented no improvement over $Man_{C24}$. The same results were also observed for compounds $TriMan_{insatC24}$ and $Man_{insatC24}$ which have an alkyl chain of 24 carbon atoms comprising two adjacent triple bonds. Altogether, these in vitro data demonstrated that the mannoside derivatives containing a $C_{24}$-lipid chain covalently linked to one, three or six mannose units bind to the CRD of DC-SIGN with a good affinity.

TABLE 1 kon, koff and Kd of mannose derivatives for DC-SIGN CRD determined by SPR (No = no binding).

| Compound | Kon ($M^{-1} \cdot s^{-1}$) | Koff ($s^{-1}$) | KD (µM) |
|---|---|---|---|
| $Man_{C1}$ | No binding | — | — |
| $Man_{C11}$ | No binding | — | — |
| $Man_{C17}$ | Low binding | — | 769 |
| $Man_{C24}$ | 273 | $0.09 \times 10^{-3}$ | 0.32 |
| $TriMan_{C24}$ | 295 | $0.94 \times 10^{-3}$ | 3.19 |
| $TriDiMan_{C24}$ | 396 | $1.20 \times 10^{-3}$ | 3.25 |
| $Man_{insatC24}$ | 538 | $1.38 \times 10^{-3}$ | 2.57 |
| $TriMan_{insatC24}$ | 2410 | $1.13 \times 10^{-3}$ | 0.47 |

$TriMan_{C24}$ Inhibits the Binding of gp120 to DCs

Figure 1:
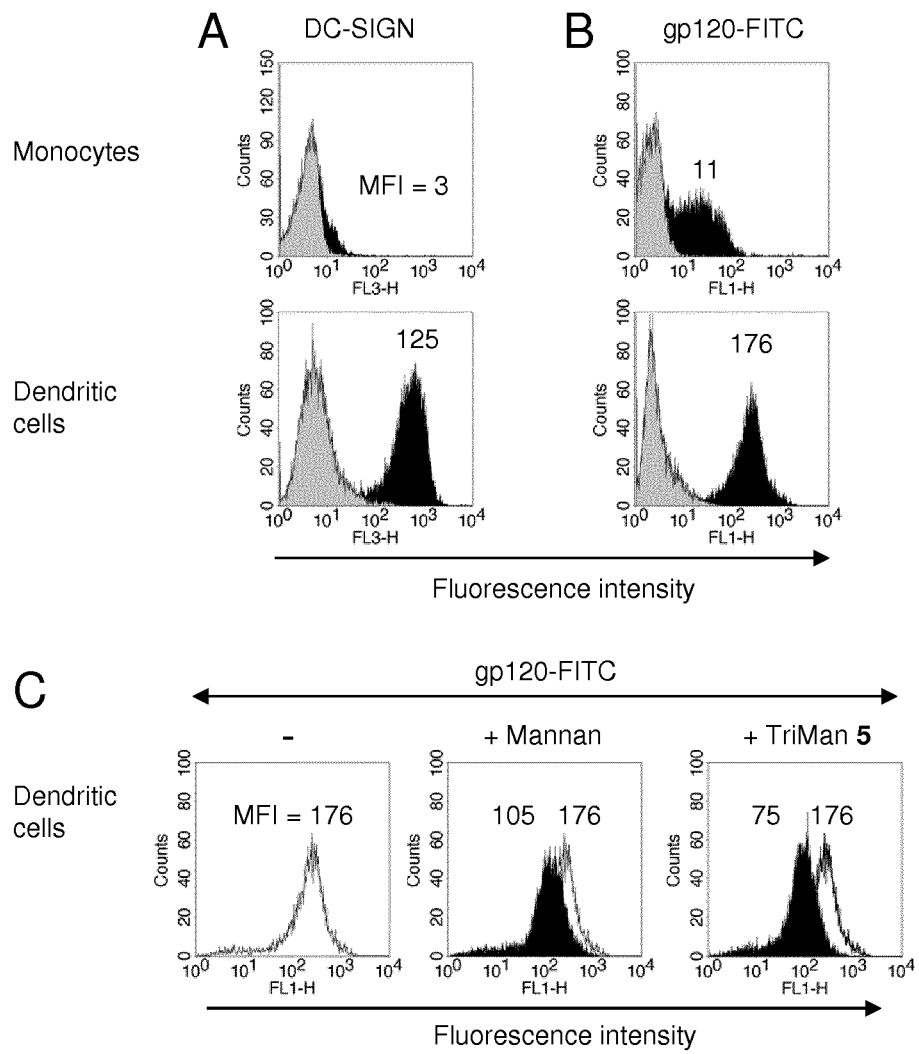
FIG. 1 TriMan$_{C24}$ competes with gp120 binding to DCs

The ability of $TriMan_{C24}$ to inhibit the interactions of HIV-1 gp120 with DC-SIGN was expressed at the surface of DCs. Immature DCs were prepared by differentiation of human monocytes, in the presence of a cocktail of cytokines. The expression levels of DC-SIGN were controlled by flow cytometry. As expected, the results showed a high level of expression on DCs, and no expression on control monocytes (FIG. 1A). When cells were incubated with fluorescently-labeled gp120, a strong binding of gp120 to DCs was observed as compared with a lower interaction with monocytes (FIG. 1B). This showed that gp120 mostly bound to DC-SIGN expressed on DCs, but interaction with other cell surface proteins is also possible (Crublet, et al., 2008; Vives, et al., 2005).

A competition assays were performed by pre-incubating DCs with either TriMan$_{C24}$ or mannan, followed by the addition of gp120-FITC (FIG. 1C). Flow cytometry results indicated that TriMan$_{C24}$ was able to inhibit the binding of gp120-FITC to DCs. Although the competition was not complete, at a 100 µM concentration, these results demonstrated the ability of TriMan$_{C24}$ to interfere, better than mannan, with the binding of gp120 to DCs.

TriMan$_{C24}$ Induces Partial DC-SIGN Internalization

To gain further insight into the interactions of TriMan$_{C24}$ with DC-SIGN expressed by DCs, a fluorescence-labeled TriMan$_{C24}$ was prepared by connecting Alexa Fluor 633 to hydroxyl groups of the mannose units. DCs were exposed to the labeled TriMan$_{C24}$ and visualized by confocal fluorescence microscopy. Images revealed the expected binding of TriMan$_{C24}$ at the cell membrane, and its internalization into the cell cytoplasm (data not shown). Further experiments using labeled transferrin, a specific marker of clathrin-mediated endocytosis (Hansen, et al., 1992), demonstrated a colocalization between TriMan$_{C24}$ and transferrin in early endosomes. Taken together, these data showed that TriMan$_{C24}$ binds to the cell membrane and can be internalized by DCs via clathrin-mediated endocytosis.

Moreover, expression of DC-SIGN was visualized with a fluorescently-labeled antibody by confocal fluorescence microscopy. In untreated cells, DC-SIGN was mostly located at the cell membrane, in agreement with previous reports (Engering, et al., 2002). Upon exposure to TriMan$_{C24}$, DC-SIGN was detected both at the cell membrane and within the cytoplasm. Although the amount of internalized receptor varied depending on the observed cell, images clearly revealed that TriMan$_{C24}$ triggered DC-SIGN internalization (data not shown). The effect of TriMan$_{C24}$ on DC-SIGN cellular localization was assessed by flow cytometry analyses of DCs, in the absence or presence of TriMan$_{C24}$. Results confirmed that DC-SIGN expressed at the cell surface was partially down-regulated in a dose-dependent manner; about 20% of the receptors were internalized at a 100 µM concentration. Together, these data demonstrated TriMan$_{C24}$-induced internalization of DC-SIGN, which may contribute to the inhibition of HIV gp120 binding to DCs.

Compounds of the Invention Inhibit HIV-1 Trans-Infection Mediated by DCs

To investigate the ability of the compounds of the invention to inhibit HIV-1 trans infection, we chose to infect human DCs in order to best mimic in vivo conditions. Human DCs were exposed to different compounds (namely, Mannan (control), Man$_{C1}$ (comparative), Man$_{C11}$ (comparative), Man$_{C17}$, ManC$_{24}$, TriMan$_{C24}$, TriDiMan$_{C24}$, Mani$_{nsatC24}$ and TriMan$_{insatC24}$) for 45 min at 37° C., before inoculation with HIV-1 (strains R5 and X4) for 3 hours. After extensive washings to remove unbound virions and mannosides, DCs were then co-cultured with MAGI-CCR5 cells. This procedure allows precise quantification of HIV-1 replication in reporter MAGI-CCR5 cells by detection of beta-galactosidase activity. These cells express an integrated copy of the HIV long terminal repeat (LTR) fused to the beta-galactosidase reporter gene, and express the CD4 receptor and the CCR5 and CXCR4 co-receptors, required for entry of HIV-1 R5 and X4 respectively. Upon viral entry leading to viral Tat expression and activation of the LTR, these cells permit quantification of HIV trans-infection after two days.

DCs were first exposed to the HIV R5 strain, mostly involved in mucosal infections (David, et al., 2001; Grivel, et al., 2011; Yamamoto, et al., 2009), in the presence of each compound to be assessed. While molecules Man$_{C1}$ and Man$_{C11}$ did not present a better inhibitory activity than mannan, both Man$_{C17}$ and Man$_{C24}$ reduced trans-infection in a dose-dependent manner (see FIG. 2A). This inhibition was in the high micromolar range, with an IC$_{50}$ of 120 µM. Dose-response experiments were further performed to compare the inhibitory capacity of Man$_{C24}$, TriMan$_{C24}$ and TriDiMan$_{C24}$. When compared with Man$_{C24}$, TriMan$_{C24}$ displayed the highest inhibitory activity in the sub-micromolar range (IC$_{50}$ of 0.5 µM). With the highest concentrations, trans-infection was drastically reduced, down to a residual level of 20% (FIG. 2B). Interestingly, these findings revealed a better ability of TriMan$_{C24}$ to inhibit viral transmission than to compete with gp120 in the previous in vitro assays (see hereabove). TriDiMan$_{C24}$ exhibited a powerful inhibitory activity in the nanomolar range (IC$_{50}$ of 38 nM), although surprisingly infection levelled off at 40% (FIG. 2C).

Unsaturated compounds—namely Man$_{insatC24}$ and TriMan$_{insatC24}$—were also able to inhibit HIV-1 R5 trans-infection of DCs: Man$_{insatC24}$ and TriMan$_{insatC24}$ blocked HIV-1 R5 trans-infection down to a residual level of 15% and 2% with an IC$_{50}$ of 61 µM and 0.305 µM, respectively. Noticeably, TriMan$_{insatC24}$ almost fully blocked HIV trans-infection at the highest concentrations (see FIG. 2E).

The effect of TriMan$_{C24}$ on the HIV-1 X4 strain was also assessed (see FIG. 2D) TriMan$_{C24}$ also induced inhibition of HIV-1 X4 trans-infection down to a residual level of 15% with a IC$_{50}$ of 7 µM. These findings demonstrated that TriMan$_{C24}$ was able to inhibit trans-infection mediated by DCs for both HIV strains R5 and X4.

Compounds of the Invention Inhibit Dengue Virus Infection of DCs

The dengue virus (DV) is a flavivirus transmitted via Aedes mosquitoes, and introduced into the skin following a mosquito bite. Dendritic cells (DCs) are highly permissive for DV replication, since DV infects DCs following binding to DC-SIGN (Navarro-Sanchez et al., 2003; Tassaneetrithep et al., 2003). Thus, this virus infects DCs by cis-infection.

There are four different dengue serotypes (1-4), and we have used DV type 2 (DV2) to further investigate the ability of the compounds of the invention (TriMan$_{C24}$ and TriMan$_{insatC24}$) to inhibit the infection of human DCs. These cells were pre-treated with different concentrations of compounds or culture medium alone, for 30 min at 37° C. They were then exposed to DV2 for 2 hours at 37° C. Cells were washed to remove excess virions and compounds, and further cultured either in the absence (condition 1) or in the presence (condition 2) of the tested compounds. After 48 hours, cells were subjected to intracellular detection of viral antigens, and supernatants were titrated (not shown). Both compounds were able to inhibit Dengue infection of DCs. FIG. 3A and FIG. 3B show the percentage of infected DCs when incubated with distinct concentrations of TriMan$_{insatC24}$ in condition 1 and in condition 2, respectively. The histograms clearly show the protecting effects of TriMan$_{insatC24}$, in particular in condition 2 wherein TriMan$_{insatC24}$ at 10, 50 and 100 µM enabled the percentage of infected DCs to be reduced down to 40%, 20% and 2% respectively.

Compounds of the Invention Inhibit HIV-1 Cis-Infection and Replication in DCs

Human monocyte-derived dendritic cells (2×10$^5$; 300 µL) in RPMI 1640 medium containing 10% FBS were pre-treated with either anti-DC-SIGN antibodies (clone AZND1, Beckman-Coulter; 10 µg/mL) or compounds TriMan$_{C24}$ and TriMan$_{C24}$insat (10 and 100 µM) for 30 min at 37° C., before inoculation with HIV-1 (R5 strain; 100 ng of p24Gag). After 3 h, cells were pelleted and extensively washed to remove excess virus and compounds. On day 2, 4 and 7 after infection, cells were pelleted, an aliquot of the supernatant was removed and kept at −20° C., and half of the supernatant was replaced with fresh medium. Viral replication was monitored by measuring p24Gag levels in the culture supernatant by an enzyme-linked immunosorbent assay (ELISA, Innogenetics). The results are shown in FIG. 5. It clearly appears that the pre-incubation of DCs with $TriMan_{C24}$ and $TriMan_{C24insat}$ decreases the amount of HIV R5 replication. As shown in the case of Dengue virus, the compounds of the invention may also interfere with HIV cis-infection. The Applicant further showed that the compounds of the invention are able to prevent the infection of cell lines other than DCs by HIV (data not shown).

c. Discussion

Nowadays, there are 32 antiretroviral drugs approved for therapy, since the beginning of the AIDS pandemic. They all target viral sites, such as entry, reverse transcription, integration, and maturation (De Clercq, 2007; Flexner, 2007). Their drawbacks are virus-induced drug resistance and drug-induced side effects. A complementary approach is now dedicated to the search of inhibitors able to prevent mucosal infection and transmission. In addition, the strategy of targeting host cells should also prevent virus mutations and drug resistance. In the case of dengue virus infection, which may lead to dengue fever, dengue hemorrhagic fever (DHF) or dengue shock syndrome, no specific antiviral drugs or vaccines are currently available. Only adequate supportive care and treatment control its morbidity. The worldwide incidence is estimated to be 50 to 100 million cases of dengue fever and several hundred thousand cases of DHF per year, with a fatality rate of about 5% for DHF.

In this respect, the present invention provides new mannoside derivatives comprising a lipid tail able to interact with the extracellular domain of DC-SIGN, as demonstrated by surface plasmon resonance (SPR) analysis. One mannose unit, such as in $Man_{C24}$, was sufficient for an effective interaction with DC-SIGN CRD, with a Kd in the sub-micromolar range. The correlation between the length of the lipid chain and the binding affinity of the molecules highlighted the role of the lipid moiety, in assisting the mannose polar head for optimal binding. In vitro SPR data correlated with HIV-1 trans -infection results, since molecules with a short lipid chain ($Man_{C1}$ and $Man_{C11}$) were unable to bind DC-SIGN and to act as inhibitors. A $C_{17}$-chain appeared as the minimum length for activity. Although $Man_{C17}$ and $Man_{C24}$ displayed distinct in vitro affinities, they were both able to inhibit trans-infection to a similar extent.

It was also shown that the compounds of the invention—$TriMan_{C24}$ and $TriMan_{insatC24}$—were able to inhibit the direct infection of DCs by Dengue virus. In particular, when $TriMan_{insatC24}$ was used before and during the infection of DCs, it was able to inhibit DCs infection after 2 days, with IC50 in the low micromolar range (below 10 μM) (see FIG. 3B).

The results obtained for the compounds of the invention were surprising in view of previous studies suggesting that high mannose structures, such as that of dendrimers, were required for obtaining a high affinity for DC-SIGN Some compounds of the invention ($Man_{C17}$, $Man_{C24}$ and $TriMan_{C24}$) possess the property to self-organize into micelles in aqueous medium with a CMC of about 100 μM. However, it was shown that the compounds of the invention were able to inhibit viral trans -infection at concentrations lower than their CMC. In this respect, it should be noticed that $TriDiMan_{C24}$ failed to form micelles.

Such results strongly suggest that the compounds of the invention are able to exert their biological activities as single molecules without being self-assembled in micelles. In other words, the biological activity of the compounds of the invention—namely, their affinity for DC-SIGN, their ability to compete for gp120 DC-SIGN binding, and their ability to inhibit HIV-1 trans-infection and dengue cis-infection of DCs—may result from a synergism between their lipid chain and their mannose moiety rather than their structuration into micelles.

Noticeably, the compounds of the invention were synthesized in easy and efficient steps. They are water-soluble, and present no in vitro cytotoxicity.

In view of the above-described experimental assays, the compounds of the invention—and in particular $TriMan_{C24}$—may affect HIV trans-infection by distinct complementary mechanisms. The most likely hypothesis relies on the shield strategy, in which the binding of $TriMan_{C24}$ to DC-SIGN at the DCs cell membrane prevents the attachment of HIV-1 via gp120 to this receptor. Moreover, partial down-regulation of DC -SIGN from the cell surface may enhance the $TriMan_{C24}$ protective effect. One could also hypothesize a direct effect of $TriMan_{C24}$ on the virus particle. The precise inhibitory mechanisms remain to be investigated.

REFERENCES

Alvarez et al. (2002),. *J. Virol.* 76, 6841-6844.
Baleux, et al. (2009). *Nat. Chem. Biol.* 5, 743-748.
Banchereau et al., (2000) *Annu. Rev. Immunol.,* 18, 767-811
Banoub et al. 1986, *Tet. Lett.* 27, 4145-4148
Canard, et al. (2011). *Immunol. Lett.* 135, 165-172.
Cavrois, et al. (2007). *PLoS Pathog.* 3, e4.
Chackerian, et al. (1997). *J. Virol.* 71, 3932-3939.
Crublet, et al.; (2008). *J. Biol. Chem.* 283, 15193-15200.
David, et al.; (2001). *AIDS Res. Hum. Retroviruses* 17, 59-68.
De Clercq, E. (2007). *Nat. Rev. Drug Discov.* 6, 1001-1018.
Duffels, A., et al. D. (2000). *Chem. Eur. J.* 6, 1416-1430.
Engering, A., et al. (2002). *J. Immunol.* 168, 2118-2126.
Feinberg, H., et al. (2001),. *Science* 294, 2163-2166.
Flexner, C. (2007). *Nat. Rev. Drug Discov.* 6, 959-966.
Frison et al. (2003), *Journal of Biological Chemistry,* 278, 23922-23929
Geijtenbeek, T. B., et al. (2000). *Cell* 100, 587-597.
Geijtenbeek, and van Kooyk (2003). *Curr. Top. Microbiol. Immunol.* 276, 31-54.
Geijtenbeek and van Kooyk (2003). *APMIS* 111, 698-714.
Geijtenbeek et al. (2003), *J. Exp. Med.* 197, 7-17.
Grivel, et al. (2011), *J. Transl. Med.* 9 Suppl 1, S6.
Gurney, K. B., et al. (2005), *J. Virol.* 79, 5762-5773.
Hansen, et al. (1992). *Exp. Cell Res.* 199, 19-28.
Hatch, et al. (2008). *ChemBioChem.* 9, 2433-2442.
Hu, J., et al. (2000) *J. Virol.* 74, 6087-6095.
Kikkeri, et al. (2009). *Chem. Com.* 235-237.
Khiar, et al. (2009). *Chem. Corn.* 4121-4123.
Kooyk and Geijtenbeek, (2003), *Nat Rev Immunol.,* 3, 697-709
Kooyk, and Geijtenbeek, (2004). *J. Virol.* 78, 8322-8332.
Lambeth, C. R., et al., (2005), *J. Clin. Microbiol.* 43:3267-3272.
Martinez-Avila, et al. (2009). *Chemistry* 15, 9874-9888.
Mitchell, et al. (2001). *J. Biol. Chem.* 276, 28939-28945.
Navarro-Sanchez, et al. (2003), *EMBO Rep.* 4:723-728.

Oversteegen et al. (2007) *Nat. Rev. Drug Discov.* 2007, 951-952
Perino, et al. (2011). *Macromol. Chem. Phys.* 212 (2), 111-117.
Piguet, and Steinman, (2007). *Trends Immunol.* 28, 503-510.
Sattin, et al. (2010). *ACS Chem. Biol.* 5, 301-312.
Schaeffer, et al. (2004) *J. Virol.* 78, 1375-1383.
Shen et al. (2010). *J. Leukoc. Biol.* 87, 663-670.
Sidobre, et al. (2002). *Biochem J* 365, 89-97.
Su, et al. (2010). *Eur. J. Med. Chem.* 45, 2713-2718.
Tabarani, et al. (2006). *FEBS Lett.* 580, 2402-2408.
Tassaneetrithep, et al. (2003). *J. Exp. Med.* 197, 823-829.
Tilton and Doms, (2010), *Antiviral Res.*, 85, 91-100.
Wang, et al. (2004). *Chin. Med. J. (Engl)* 117, 1395-1400.
Wang, (2008). *Biochem. Biophys. Res. Commun.* 373, 561-566.
Wang, et al. (2008). *Proc. Natl. Acad. Sci. U.S.A.* 105, 3690-3695.
Wiley, and Gummuluru, (2006). *Proc. Natl. Acad. Sci. USA* 103, 738-743.
Wilkinson, and Cunningham,. (2006). *Curr. Drug Targets* 7, 1563-1569.
Wu, and KewalRamani, (2006). *Nat. Rev. Immunol.* 6, 859-868.
Yamamoto, et al. (2009). *PLoS Pathog.* 5, e1000279.

The invention claimed is:
1. A compound of formula (III):

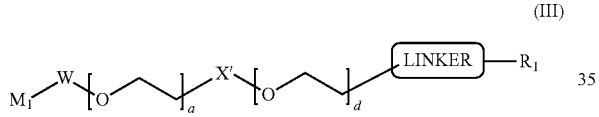

(III)

wherein:
LINKER is a bifunctional linker selected from the group consisting of:
 i) an amino acid residue,
 ii) peptides having from 2 to 10 amino acid residues,
 iii) $X_1$—$(CH_2)n$-Y, wherein n is an integer from 1 to 10 and $X_1$ and $Y_1$ are independently selected from —NH—, —S—, —C(=O)—, —O—, —NH—C(=O)—, —C(=O)—NH—, —O—C(=O)—, —C(=O)—O—, —NH—(C=NH)—NH, —NH—(C=O)—NH— and (C=O)—O—(C=O), and
 iv) —NH—, —S—, —O—, —C(=O)—, —NH—C(=O)—, —C(=O)—NH—, —O—C(=O)—, —C(=O)—O—, NH—(C=NH)—NH—, —NH—(C=O)—NH—and —(C=O)—O—(C=O)—,
$R_1$ is a $C_{17}$-$C_{30}$ saturated or unsaturated linear hydrocarbon chain, optionally substituted by one or more $C_1$-$C_3$ alkyl radicals,
$M_1$ is mannosyl, dimannosyl or trimannosyl,
W is selected from —NH—$(CH_2)_f$—, —O—$(CH_2)_f$— and —S—$(CH_2)_f$— wherein f is an integer from 1 to 5,
X' is —NH—C(O)—$(CH_2)_e$— or —O—C(O)—$(CH_2)_e$— wherein e is an integer from 1 to 4,
a is an integer from 2 to 10, and
d is an integer from 2 to 10,
or a pharmaceutically acceptable salt or solvate thereof.
2. The compound of claim 1, wherein said compound is of formula (IIIa)

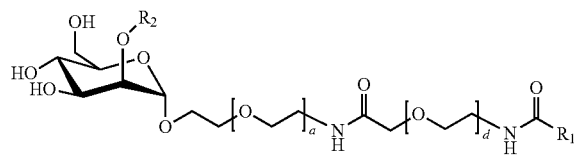

(IIIa)

wherein:
$R_2$ is H or α-mannosyl residue,
$R_1$ is the $C_{17}$-$C_{30}$ saturated or unsaturated linear hydrocarbon chain, optionally substituted by one or more $C_1$-$C_3$ alkyl radicals,
a is an integer from 2 to 10, and
d is an integer from 2 to 10.
3. The compound of claim 2, wherein said compound is selected from the group consisting of:
a compound of formula (IIIa), wherein $R_2$ is H, $R_1$ is —$(CH_2)_{16}CH_3$, a is 3 and b is 4;
a compound of formula (IIIa), wherein $R_2$ is H, $R_1$ is —$(CH_2)_{23}CH_3$, a is 3 and b is 4; and
a compound of formula (IIIa), wherein $R_1$ is —$(CH_2)_8$—C≡C—C≡C—$(CH_2)_{11}$—$CH_3$, $R_2$ is H, a is 3, and b is 4.
4. A compound of formula (Ic):

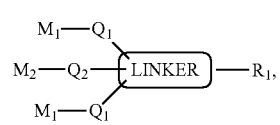

(I)

wherein:
$M_1$ is selected from the group consisting of mannosyl, dimannosyl, and trimannosyl,
$M_2$ and $M_3$ are independently selected from the group consisting of mannosyl, dimannosyl, trimannosyl, and therapeutic agent moieties having a molecular weight of at most 800 g/mol$^{-1}$,
$Q_1$, $Q_2$ and $Q_3$ are independently selected from the group of oligoether-based spacers comprising at least one —$(R_8O)_n$— moiety wherein $R_8$ is a linear or branched $C_1$-$C_4$ alkyl, and n is an integer from 2 to 10,
$R_1$ is a $C_{17}$-$C_{30}$ saturated or unsaturated linear hydrocarbon chain optionally substituted by one or more $C_1$-$C_3$ alkyl radicals, and
LINKER is a radical of formula (VI)

(VI)

wherein:
$R_6$ is —NH—C(O)— or —O—C(O)—, and
$R_3$, $R_4$ and $R_5$ are independently selected from —NH—C(=O)—$(CH_2)_n$—O— and —O—C(=O)$(CH_2)_n$—O— wherein n is an integer from 1 to 10. or a pharmaceutically acceptable salt or solvate thereof.

5. The compound of claim 4, wherein said compound is of formula (V):

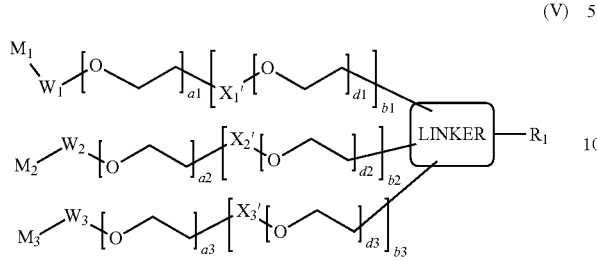

wherein:
$R_1$ is a $C_{17}$-$C_{30}$ saturated or unsaturated linear hydrocarbon chain, optionally substituted by one or more $C_1$-$C_3$ alkyl radicals,
$M_1$ is mannosyl or dimannosyl,
$M_2$ and $M_3$ are independently selected from the group consisting of mannosyl, dimannosyl, and therapeutic agent moieties, having a molecular weight of at most 800 g/mol$^{-1}$,
$W_1$, $W_2$ and $W_3$ are independently selected from —NH—$(CH_2)_f$—, —O—$(CH_2)_f$— and —S—$(CH_2)_f$— wherein f is an integer from 1 to 5,
$X'_1$, $X'_2$ and $X'_3$ are independently selected from —NH—C(O)—$(CH_2)_e$— and —O—C(O)—$(CH_2)_e$— wherein e is an integer from 1 to 4,
a1, a2, a3, d1, d2 and d3 are integers independently selected from integers ranging from 2 to 10, and
1 b1, b2 and b3 are independently selected from 0 and 1, or a pharmaceutically acceptable salt or solvate thereof.

6. The compound of claim 4, wherein the compound is of formula (Va):

7. The compound of claim 6, wherein the compound is selected from the group consisting of:
a compound of formula (Va), wherein, $R_1$ is —$(CH_2)_{23}CH_3$, $R_2$ is H, and a is 3;
a compound of formula (Va), wherein, $R_1$ is —$(CH_2)_{23}CH_3$, $R_2$ is α-mannosyl, and a is 3;
a compound of formula (Va), wherein, $R_1$ is —$(CH_2)_8$—C≡C—C≡C—$(CH_2)_{11}$—$CH_3$, $R_2$ is H, and a is 3; and
a compound of formula (Va), wherein, $R_1$ is —$(CH_2)_8$—C≡C—C≡C—$(CH_2)_{11}$—$CH_3$, $R_2$ is α-mannosyl and a is 3.

8. A condom coated with a compound according to claim 1.

9. A pharmaceutical composition comprising (i) a compound according to claim 1, (ii) at least one pharmaceutically acceptable excipient and (iii) optionally an additional therapeutic agent.

10. The compound of claim 1, wherein $R_1$ is selected from the group consisting of:
(i) —$(CH_2)_p CH_3$ wherein p is an integer from 16 to 29;
(ii) —$(CH_2)_p$-M—$(CH_2)_q$—$CH_3$ wherein M is CH=CH or C≡C and p and q are integers from 0 to 27 with the proviso that $14 \leq p+q < 27$;
(iii) —$(CH_2)_p$—K—$(CH_2)_q$-M—$(CH_2)_r$—$CH_3$ wherein K and M are independently selected from CH=CH and C≡C, and p, q and r are integers from 0 to 25 with the proviso that $12 \leq p+q+r \leq 25$;
(iv) —$(CH_2)_p$—K—$(CH_2)_q$-M—$(CH_2)_r$—P—$(CH_2)_s$—$CH_3$ wherein K, M and P are independently selected from CH=CH and C≡C, and p, q, r and s are integers from 0 to 23 with the proviso that $10 \leq p+q+r+s \leq 23$; and
(v) —$(CH_2)_p$—C=C=C—$(CH_2)_q$—$CH_3$ wherein p and q are integers from 0 to 26 with the proviso that $13 \leq p+q \leq 26$.

11. The compound of claim 10, wherein $R_1$ is —$(CH_2)_p$—K—$(CH_2)_q$-M—$(CH_2)_r$—$CH_3$ and wherein:

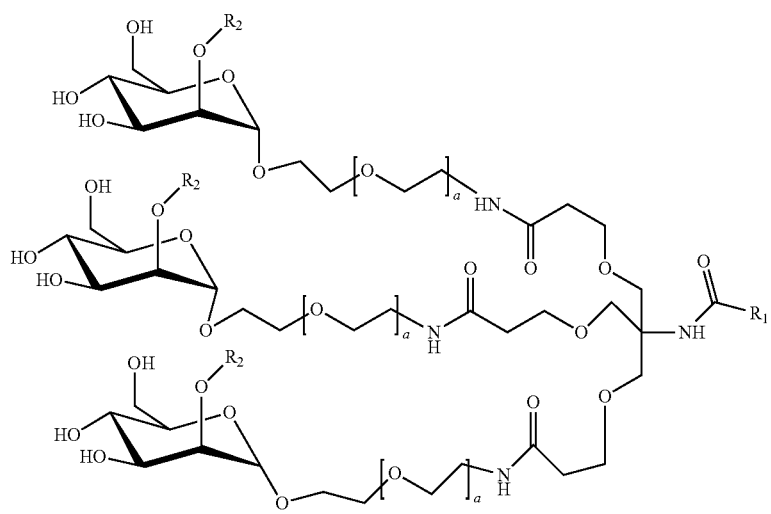

wherein:
—$R_2$ is H or α-mannosyl residue,
$R_1$ is $C_{17}$-$C_{30}$ saturated or unsaturated linear hydrocarbon chain, optionally substituted by one or more $C_1$-$C_3$ alkyl radicals, and
a is an integer from 1 to 10.

K and M are C≡C, and p, q and r are integers from 0 to 25 with q is 0 and with the proviso that $12 \leq p+q+r \leq 25$.

12. The compound of claim 1, wherein $M_1$ is selected from the group consisting of Man α, Man α(1->2)Man α, Man α(1->3)Man α, Man α(1->4)Man α, and Man α(1->6)Man α.

13. The compound of claim 1, wherein LINKER is selected from the group consisting of O—C(=O)—, —C(=O)—O—, —NHC(=O)— and —C(=O)NH—.

14. The compound of claim 4, wherein $R_1$ is selected from the group consisting of:
   (i) —$(CH_2)_p CH_3$ wherein p is an integer from 16 to 29;
   (ii) —$(CH_2)_p$—M—$(CH_2)_q$—$CH_3$ wherein M is CH=CH or C≡C and p and q are integers from 0 to 27 with the proviso that 14≤p+q≤27;
   (iii) —$(CH_2)_p$—K—$(CH_2)_q$-M—$(CH_2)_r$—$CH_3$ wherein K and M are independently selected from CH=CH and C≡C, and p, q and r are integers from 0 to 25 with the proviso that 12≤p+q+r≤25;
   (iv) —$(CH_2)_p$—K—$(CH_2)_q$-M—$(CH_2)_r$—P—$(CH_2)_s$—$CH_3$ wherein K, M and P are independently selected from CH=CH and C≡C, and p, q, r and s are integers from 0 to 23 with the proviso that 10≤p+q+r+s≤23; and
   (v) —$(CH_2)_p$—C≡C—C≡C—$(CH_2)_q$—$CH_3$ wherein p and q are integers from 0 to 26 with the proviso that 13≤p+q≤26.

15. The compound of claim 14, wherein $R_1$ is —$(CH_2)_p$—K—$(CH_2)_q$-M—$(CH_2)_r$—$CH_3$ wherein K and M are C≡C, and p, q and r are integers from 0 to 25 with q is 0 and with the proviso that 12≤p+q+r≤25.

16. The compound of claim 4, wherein $M_1$, $M_2$ and $M_3$ are independently selected from the group consisting of Man α, Man α(1->2)Man α, Man α(1->3)Man α, Man α(1->4) Man α, and Man α(1->6)Man α.

17. A compound of formula (Ib)

wherein:
   LINKER is a trifunctional linker selected from the group of amino acid residues selected from arginine, lysine, aspartate, glutamine, asparagine, serine and threonine and peptides having from 2 to 10 amino acid residues,
   $M_1$ is selected from the group consisting of mannosyl, dimannosyl, and trimannosyl,
   $M_2$ is selected from the group consisting of mannosyl, dimannosyl, trimannosyl, and therapeutic agent moieties having a molecular weight of at most 800 g/mol-1,
   $Q_1$, and $Q_2$ are independently selected from the group of oligoether-based spacers comprising at least one —$(R_8O)_n$— moiety wherein $R_8$ is a linear or branched $C_1$-$C_4$ alkyl, and n is an integer from 2 to 10, and
   $R_1$ is a $C_{17}$-$C_{30}$ saturated or unsaturated linear hydrocarbon chain optionally substituted by one or more $C_1$-$C_3$ alkyl radicals and a pharmaceutically acceptable salt or solvate thereof.

18. The compound of claim 17, wherein $Q_1$ and $Q_1$ are independently —W—(O—$CH_2$—$CH_2$)$_a$—(X'—(O—$CH_2$—$CH_2$)$_d$)$_b$— (II) wherein:
   W is selected from —NH—$(CH_2)_f$—, —O—$(CH_2)_f$— and —S—$CH_2)_f$— wherein f is an integer from 1 to 5.
   a is an integer from 2 to 10,
   b is 0 or 1,
   d is an integer from 2 to 10, and
   X' is —NH—C(O)—$(CH_2)_e$— or —O—C(O)—$(CH_2)_e$— wherein e is an integer from 1 to 4.

19. A condom coated with a compound according to claim 4.

20. A pharmaceutical composition comprising (i) a compound according to claim 4, (ii) at least one pharmaceutically acceptable excipient and (iii) optionally an additional therapeutic agent.

* * * * *

UNITED STATES PATENT AND TRADEMARK OFFICE
CERTIFICATE OF CORRECTION

PATENT NO. : 9,522,928 B2
APPLICATION NO. : 14/358157
DATED : December 20, 2016
INVENTOR(S) : Rachid Baati et al.

It is certified that error appears in the above-identified patent and that said Letters Patent is hereby corrected as shown below:

In the Specification

Column 3,
Line 31, "—(OR$_8$)$_n$-moiety," should read -- —(OR$_8$)$_n$- moiety,--.

Column 4,
Lines 44-45, "—NH—(CH$_2$)$_r$, —O—(CH$_2$)$_r$— and —S—(CH$_2$)$_r$—," should read
-- —NH—(CH$_2$)$_r$—, —O—(CH$_2$)$_r$— and —S—(CH$_2$)$_r$—,--.
Line 47, "—O—(O)—(CH$_2$)$_e$—," should read -- —O—C(O)—(CH$_2$)$_e$—,--.

Column 5,
Lines 12-13, "—NH—(CH$_2$)$_r$, —O—(CH$_2$)$_r$— and —S—(CH$_2$)$_r$—," should read
-- —NH—(CH$_2$)$_r$—, —O—(CH$_2$)$_r$— and —S—(CH$_2$)$_r$—,--.

Column 6,
Lines 7-8, "—(CH$_2$)$_8$—C≡C≡C—(CH$_2$)$_{11}$—CH$_3$," should read
-- —(CH$_2$)$_8$—C≡C—C≡C—(CH$_2$)$_{11}$—CH$_3$,--.
Line 12, "and is H, a is 3, and b is 4;" should read --and a is 3;--.
Lines 15-16, "—(CH$_2$)$_8$—C≡C—C≡C—CH$_2$)$_{11}$—CH$_3$," should read
-- —CH$_2$)$_8$—C≡C—C≡C—(CH$_2$)$_{11}$—CH$_3$,--.

Column 8,
Line 30, "DCM/Et20," should read --DCM/Et2O,--.
Line 49, "Net3," should read --NEt$_3$,--.

Column 10,
Line 38, "—(OR$_8$)$_n$-moiety," should read -- —(OR$_8$)$_n$— moiety,--.

<div style="text-align:center">
Signed and Sealed this
First Day of August, 2017
</div>

<div style="text-align:center">
Joseph Matal
*Performing the Functions and Duties of the
Under Secretary of Commerce for Intellectual Property and
Director of the United States Patent and Trademark Office*
</div>

Column 11,
Line 44, "—C(=O)—0—," should read -- —C(=O)—O—,--.

Column 14,
Line 63, "—CH$_2$)$_p$—C=C=C—Ch$_2$)$_q$—CH$_3$," should read -- —(CH$_2$)$_p$—C=C=C—(CH$_2$)$_q$—CH$_3$,--.

Column 15,
Line 36, "—(CH$_2$)$_p$—K—(CH$_2$)$_q$-M-(CH$_2$)$_r$P—(CH$_2$)$_s$—CH$_3$" should read
-- —(CH$_2$)$_p$—K—(CH$_2$)$_q$-M-(CH$_2$)$_r$—P—(CH$_2$)$_s$—CH$_3$--.

Column 17,
Lines 5-6, "—W—(O—CH$_2$—CH$_2$)$_a$—(X'(O—CH$_2$—CH$_2$)$_d$)$_b$—," should read
-- —W—(O—CH$_2$—CH$_2$)$_a$—(X'—(O—CH$_2$—CH$_2$)$_d$)$_b$—,--.
Line 65, "—NHC(50 O)—." should read -- —NHC(=O)—.--.

Column 18,
Line 41, "—S—(CH$_2$)$_r$," should read -- —S—(CH$_2$)$_r$—,--.

Column 19,
Line 30, "—S—(CH$_2$)$_r$," should read -- —S—(CH$_2$)$_r$—,--.

Column 25,
Lines 63-64, "—CH$_2$)$_8$C≡C—C≡C—(CH$_2$)$_{11}$—CH$_3$," should read
-- —(CH$_2$)$_8$—C≡C—C≡C—(CH$_2$)$_{11}$—CH$_3$,--.

Column 33,
Line 18, "(Via)" should read --(VIa)--.

Column 34,
Line 52, "R$_i$COOH" should read --R$_1$COOH--.

Column 35,

Lines 37-59,
" 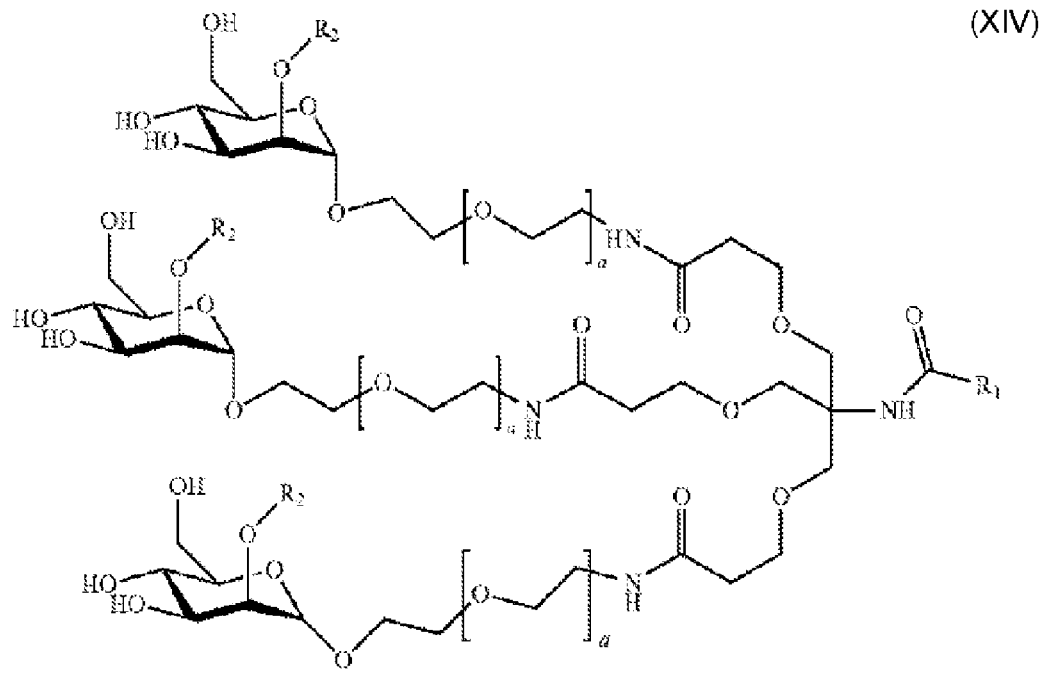 " should
read -- 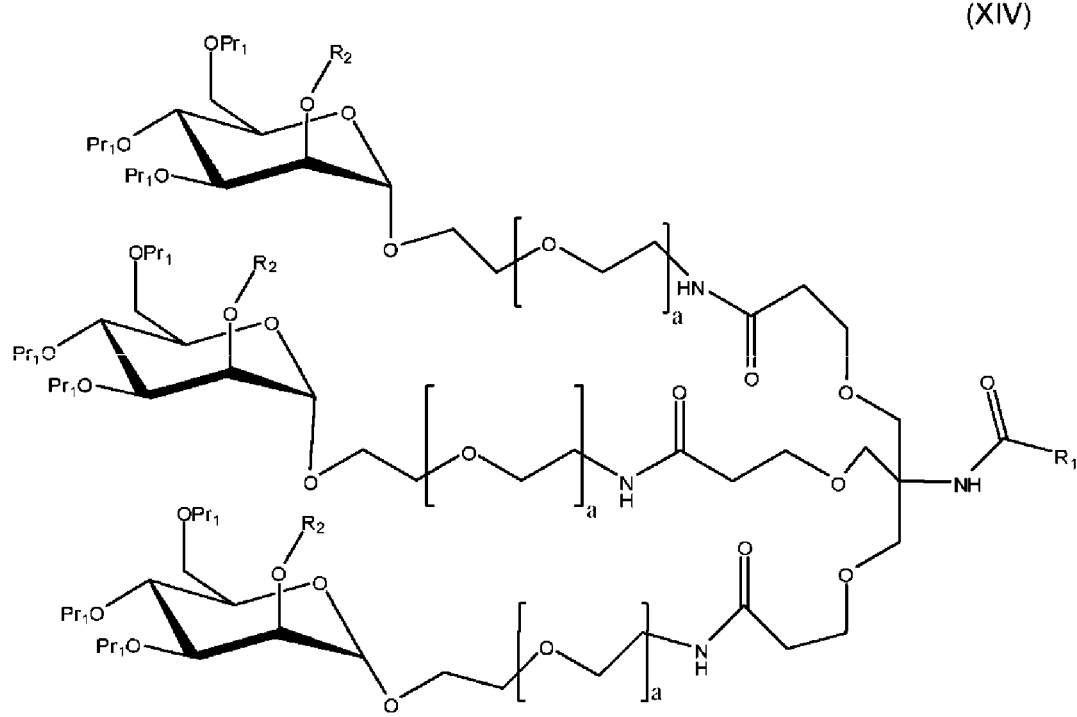 --.
Column 37,

CERTIFICATE OF CORRECTION (continued)
U.S. Pat. No. 9,522,928 B2

Line 2, "APCl/ESI," should read --APCI/ESI,--.
Line 7, "APCl/ESI" should read --APCI/ESI--.
Line 56, "NH2)," should read --NH$_2$),--.

Column 39,
Line 51, "[M+]$^+$:" should read --[M+H]$^+$:--.

Column 40,
Line 2, "[M+H]$^+$" should read --[M+H]$^+$:--.
Line 18, "Man$_{C24}$ (Invention)" should read --Man$_{C24}$ 4 (Invention)--.
Line 28, "2(14" should read --2 (14--.
Line 50, "13C" should read --$^{13}$C--.

Column 43,
Line 12, "NaHCO3" should read --NaHCO$_3$--.

Column 45,
Lines 7-19,

" 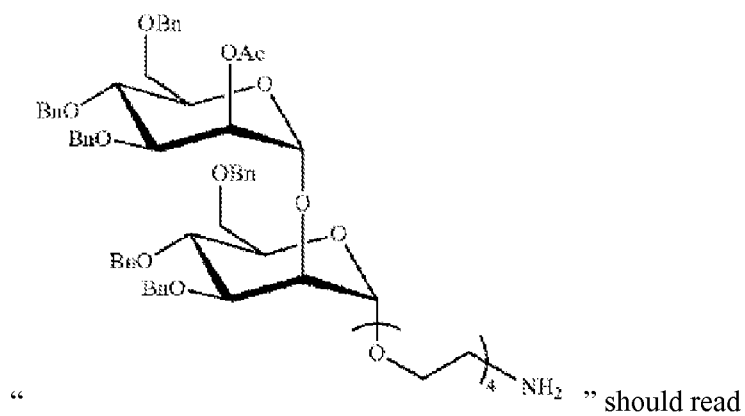 " should read

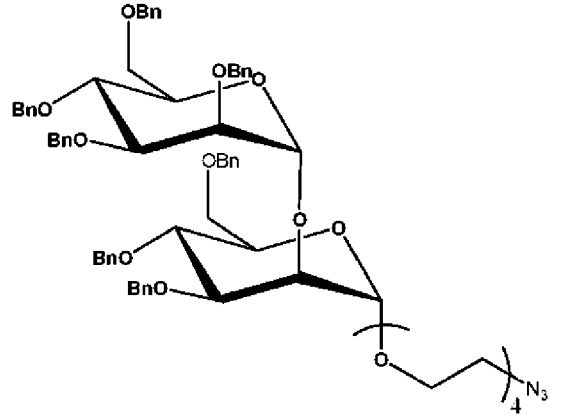

--                                   --.

Line 29, "Et2O." should read --Et$_2$O.--.
Column 46,

CERTIFICATE OF CORRECTION (continued)
U.S. Pat. No. 9,522,928 B2

Line 7, "DCM/MeOH/NEt3" should read --DCM/MeOH/NEt$_3$--.
Line 37, "0.13(DCM/MeOH:" should read --0.13 (DCM/MeOH:--.
Line 54, "C$_{230}$H$_{296}$N4O$_{52}$" should read --C$_{230}$H$_{296}$N$_4$O$_{52}$--.

Column 48,
Line 20, "δ(ppm)" should read --δ (ppm)--.

Column 51,
Line 14, "7 mG(ppp)A" should read --7mG(ppp)A--.
Line 39, "TriMan$_{insatC24}$)" should read --TriMan$_{insatC24}$)--.

Column 54,
Line 67, "TriMan$_{C24}$insat" should read --TriMan$_{C24insat}$--.